US009122777B2

(12) United States Patent
Rosenberg et al.

(10) Patent No.: US 9,122,777 B2
(45) Date of Patent: Sep. 1, 2015

(54) METHOD FOR DETERMINING CORONARY ARTERY DISEASE RISK

(75) Inventors: Steven Rosenberg, Oakland, CA (US); Michael R. Elashoff, Redwood City, CA (US); Philip Beineke, Mountain View, CA (US); James A. Wingrove, Sunnyvale, CA (US); Whittemore G. Tingley, San Francisco, CA (US); Susan E. Daniels, Mountain View, CA (US)

(73) Assignee: CardioDx, Inc., Redwood City, CA (US)

( * ) Notice: Subject to any disclaimer, the term of this patent is extended or adjusted under 35 U.S.C. 154(b) by 268 days.

(21) Appl. No.: 12/816,232

(22) Filed: Jun. 15, 2010

(65) Prior Publication Data

US 2011/0015865 A1   Jan. 20, 2011

Related U.S. Application Data

(60) Provisional application No. 61/187,203, filed on Jun. 15, 2009, provisional application No. 61/245,190, filed on Sep. 23, 2009.

(51) Int. Cl.
| | | |
|---|---|---|
| *G01N 33/48* | (2006.01) | |
| *G06F 19/00* | (2011.01) | |
| *C12Q 1/68* | (2006.01) | |
| *G06F 19/20* | (2011.01) | |
| *G06F 19/24* | (2011.01) | |

(52) U.S. Cl.
CPC .............. *G06F 19/34* (2013.01); *C12Q 1/6883* (2013.01); *C12Q 2600/158* (2013.01); *G06F 19/20* (2013.01); *G06F 19/24* (2013.01)

(58) Field of Classification Search
None
See application file for complete search history.

(56) References Cited

U.S. PATENT DOCUMENTS

| | | | |
|---|---|---|---|
| 7,695,916 B2 | 4/2010 | Iakoubova et al. | |
| 2003/0039993 A1 | 2/2003 | Rosen et al. | |
| 2005/0032066 A1 | 2/2005 | Heng et al. | |
| 2007/0015170 A1 | 1/2007 | Salonen et al. | |
| 2007/0031890 A1 | 2/2007 | Wohlgemuth et al. | |
| 2007/0238124 A1 | 10/2007 | Chibout et al. | |
| 2008/0057590 A1* | 3/2008 | Urdea et al. ................... 436/71 |
| 2008/0300797 A1 | 12/2008 | Tabibiazar et al. | |
| 2011/0183866 A1* | 7/2011 | Clarke et al. .................. 506/9 |

FOREIGN PATENT DOCUMENTS

| | | |
|---|---|---|
| CN | 102239412 A | 11/2011 |
| JP | 2007-515155 A | 6/2007 |
| WO | WO 03/020118 A2 | 3/2003 |
| WO | WO 2005/040422 A2 | 5/2005 |
| WO | WO 2005/103720 A1 | 11/2005 |
| WO | WO 2007/029249 A2 | 3/2007 |
| WO | WO 2008/102380 A1 | 8/2008 |
| WO | WO 2008/132763 A2 | 11/2008 |
| WO | WO 2009/049257 A2 | 4/2009 |
| WO | WO 2010/148017 A1 | 12/2010 |

OTHER PUBLICATIONS

Dent et al. (Atherosclerosis, 2010, 213:352-362).*
Arnett et al. (Ann Intern Med., Oct. 2010;153(7):473-474).*
Rosenberg et al. (Ann Intern Med., 2010;153:425-434).*
Vogt et al. (Clinical Chem., 1992, 38/2, 182-196).*
PCT International Search Report and Written Opinion, PCT Application No. PCT/US10/38712, Aug. 20, 2010, 8 pages.
Brunet, J.P. et al., "Metagenes and Molecular Pattern Discovery Using Matrix Factorization," Proc Natl Acad Sci USA, Mar. 23, 2004; pp. 4164-4169, vol. 101, No. 12.
Chaitman, B.R. et al., "Angiographic Prevalence of High Risk Coronary Artery Disease in Patient Subsets (CASS)," Circulation, 1981, pp. 360-367, vol. 64, No. 2.
Chung, C.P. et al., "Increased Coronary-Artery Atherosclerosis in Rheumatoid Arthritis: Relationship to Disease Duration and Cardiovascular Risk Factors," Arthritis & Rheumatism, Oct. 2005, pp. 3045-3053, vol. 52, No. 10.
Cook, N. R. et al., "The Use and Magnitude of Reclassification Measures for Individual Predictors of Global Cardiovascular Risk," Ann Intern Med., Jun. 2, 2009, pp. 795-802, vol. 150, No. 11.
Cruz-Munoz, M.E. et al., "Influence of CRACC, a SLAM Family Receptor Coupled to the Adaptor EAT-2, on Natural Killer Cell Function," Nature Immunology, Mar. 2009, pp. 297-305, vol. 10, No. 3.
Diamond G.A. et al., "Analysis of Probability as an Aid in the Clinical Diagnosis of Coronary-Artery Disease," The New England Journal of Medicine, Jun. 14, 1979, pp. 1350-1358, vol. 300, No. 24.
Elashoff, M.R. et al., "Development of a Blood-Based Gene Expression Algorithm for Assessment of Obstructive Coronary Artery Disease in Non-Diabetic Patients," BMC Medical Genomics, 2011, 14 pages, vol. 4, No. 26.
Ellegren, H. et al., "The Evolution of Sex-Biased Genes and Sex-Biased Gene Expression," Nature Reviews Genetics, Sep. 2007, pp. 689-698, vol. 8, No. 9.
Gibbons, R.J. et al., ACC/AHA 2002 Guideline Update for the Management of Patients with Chronic Stable Angina—Summary Article: a Report of the American College of Cardiology/American Heart Association Task Force on Practice Guidelines (Committee on the Management of Patients With Chronic Stable angina). J Am Coll Cardiol, Jan. 1, 2003, pp. 159-168, vol. 41, No. 1.
Hamblin, M. et al., "PPARs and the Cardiovascular System," Antioxidants & Redox Signaling, Jun. 2009, pp. 1415-1452, vol. 11, No. 6.
Hansson, G.K. et al., "Innate and Adaptive Immunity in the Pathogenesis of Atherosclerosis," Circulation Research, 2002, pp. 281-291, vol. 91, No. 4.
Hasegawa, H. et al., "Restricted Expression of Tumor Necrosis Factorrelated Apoptosis-Inducing Ligand Receptor 4 in Human Peripheral Blood Lymphocytes," Cell Immunology, 2004, pp. 1-7, vol. 231, No. 1-2.

(Continued)

*Primary Examiner* — Pablo S Whaley
(74) *Attorney, Agent, or Firm* — Fenwick & West LLP

(57) ABSTRACT

Markers and methods useful for assessing coronary artery disease in a subject are provided, along with kits for measuring their expression. Also provided are predictive models, based on the markers, as well as computer systems, and software embodiments of the models for scoring and optionally classifying samples.

20 Claims, 10 Drawing Sheets

(56) References Cited

OTHER PUBLICATIONS

Hong, M.G. et al., "Transcriptome-Wide Assessment of Human Brain and Lymphocyte Senescence," *PLoS* One, Aug. 2008, e3024, pp. 1-13, vol. 3, Issue 8.

Horne, B.D. et al., "Which White Blood Cell Subtypes Predict Increased Cardiovascular Risk?" Journal of the American College of Cardiology, 2005, pp. 1638-1643, vol. 45, No. 10.

Kim, D.K. et al., "Human NKG2F is Expressed and Can Associate with DAP12," Molecular Immunology, 2004, pp. 53-62, vol. 41, No. 1.

Libby, P. et al., "Inflammation and Atherosclerosis," Circulation, Mar. 5, 2002, pp. 1135-1143, vol. 105, No. 9.

Lim, S.Y. et al., "Oxidative Modifications of S100 Proteins: Functional Regulation by Redox," Journal of Leukocyte Biology, Sep. 2009, pp. 577-587, vol. 86.

Major, A.S. et al., "B-Lymphocyte Deficiency Increases Atherosclerosis in LDL Receptor-Null Mice," Arteriosclerosis Thrombosis, and Vascular Biology, 2002, pp. 1892-1898, vol. 22, No. 11.

Newson, R., "Confidence Intervals for Rank Statistics: Somers' D and Extensions," The Stata Journal, 2006, pp. 309-334, vol. 6, No. 3.

Park, M.Y. et al., "Averaged Gene Expressions for Regression," Biostatistics, 2007, pp. 212-227, vol. 8, No. 2.

Patel, M.R. et al., "Low Diagnostic Yield of Elective Coronary Angiography," N Eng/ J Med., Mar. 11, 2010, pp. 886-895, vol. 362, No. 10.

Pencina, M.J. et al., "Evaluating the Added Predictive Ability of a New Marker: from Area Under the ROC Curve to Reclassification and Beyond," Statistics in Medicine, 2008, pp. 157-172, vol. 27, No. 2.

Rana, J.S. et al., "Differential Leucocyte Count and the Risk of Future Coronary Artery Disease in Healthy Men and Women: the EPIC-Norfolk Prospective Population Study," Journal of Internal Medicine, 2007, pp. 678-689, vol. 262, No. 6.

Ridker, P.M. et al., "Development and Validation of Improved Algorithms for the Assessment of Global Cardiovascular Risk in Women: the Reynolds Risk Score," JAMA, Feb. 14, 2007, pp. 611-619, vol. 297, No. 6.

Robertson, A.K. et al., "T Cells in Atherogenesis: For Better or for Worse?" Arteriosclerosis, Thrombosi, and Vascular Biology, 2006, pp. 2421-2432, vol. 26, No. 11.

Rosenberg, S. et al., "Whole Blood Gene Expression Testing for Coronary Artery Disease in Nondiabetic Patients: Major Adverse Cardiovascular Events and Interventions in the PREDICT Trial," J. of Cardiovasc. Trans. Res., 2012, 9 pages.

Rosenberg, S. et al., "Multicenter Validation of the Diagnostic Accuracy of a Blood-based Gene Expression Test for Assessing Obstructive Coronary Artery Disease in Nondiabetic Patients," Annals of Internal Medicine, Oct. 5, 2010, pp. 425-434, W154-W158, vol. 153, No. 7.

Sinnaeve, P.R. et al., "Gene Expression Patterns in Peripheral Blood Correlate with the Extent of Coronary Artery Disease," PLoS One, Sep. 2009, e7037, pp. 1-14, vol. 4, Issue 9.

Su, A.I. et al., "A Gene Atlas of the Mouse and Human Protein-Encoding Transcriptomes," Proc Natl Acad Sci USA, Apr. 20, 2004, pp. 6062-6067, vol. 101, No. 16.

Teixeira, V.H. et al., Transcriptome Analysis Describing New Immunity and Defense Genes in Peripheral Blood Mononuclear Cells of Rheumatoid Arthritis Patients, PLoS One, Aug. 2009, e6803, pp. 1-10, vol. 4, No. 8.

Tibshirani, R., "Regression Shrinkage and Selection via the Lasso," Journal of the Royal Statistical Society B, 1996, pp. 267-288, vol. 58, No. 1.

Wang, L. et al., "Peakwide Mapping on Chromosome 3q13 Identifies the Kalirin Gene as a Novel Candidate Gene for Coronary Artery Disease," The American Journal Human Genetics, Apr. 2007, pp. 650-663, vol. 80, No. 4.

Whitman, S.C. et al., "Depletion of Natural Killer Cell Runction Decreases Atherosclerosis in Low-Density Lipoprotein Receptor Null Mice," Arteriosclerosis, Thrombosis, and Vascular Biology, Feb. 26, 2004, pp. 1049-1054, vol. 24, No. 6.

Wingrove, J.A. et al., "Correlation of Peripheral-Blood Gene Expression With the Extent of Coronary Artery Stenosis," Circulation: Cardiovascular Genetics. 2008, pp. 31-38, vol. 1, No. 1.

Yamasaki, S. et al., "Mincle is an ITAM-Coupled Activating Receptor That Senses Damaged Cells," Nature Immunology, Oct. 2008, pp. 1179-1188, vol. 9, No. 10.

Zheng, Q. et al., "GOEAST: a Web-Based Software Toolkit for Gene Ontology Enrichment Analysis," Nucleic Acids Research, 2008,(Web Server issue), pp. W358-W363, vol. 36.

European Extended Search Report, European Application No. 10790073.0, Nov. 23, 2012, 5 pages.

Ma, J. et al., "Gene Profiling Identifies Secreted Protein Transcripts from Peripheral Blood Cells in Coronary Artery Disease," Journal of Molecular and Cellular Cardiology, Aug. 2003, pp. 993-998, vol. 35, No. 8.

Australian First Office Action, Australian Application No. 2010260152, Sep. 2, 2013, 4 pages.

Eurasian Office Action, Eurasian Application No. 201270020/13, Nov. 1, 2013, 3 pages.

Singapore Office Action, Singapore Application No. 2011090107, Apr. 17, 2014, 10 pages.

Wingrove, J.A. et al., "Correlation of Peripheral-Blood Gene Expression with the Extent of Coronary Artery Stenosis," Circulation Cardiovascular Genetics, pp. 31-38, vol. 1.

Chinese First Office Action, Chinese Application No. 201080036171.X, Mar. 5, 2014, 65 pages.

Eurasian Second Office Action, Eurasian Application No. 201270020/13, Mar. 7, 2014, 2 pages.

United States Office Action, U.S. Appl. No. 14/157,196, Mar. 12, 2014, 9 pages.

European Examination Report, European Application No. 10790073.0, Jul. 22, 2014, 4 pages.

European Examination Report, European Application No. 10790073.0, Jan. 27, 2015, 3 pages.

Japanese Office Action, Japanese Application No. 2012-516212, Oct. 23, 2014, 12 pages.

Wingrove, J.A. et al., "Correlation of Peripheral-Blood Gene Expression with the Extent of Coronary Artery Stenosis," Circulation Cardiovascular Genetics, 2008, pp. 31-38, vol. 1.

* cited by examiner

Figure 5

Algorithm Terms and Genes

Males

1) Neutrophil Activation - Apoptosis
Innate Immunity (IL18RAP+TNFAIP6+CASP5) -
(IL8RB+TNFRSF10C+TLR4+KCNE3)

2) Neutrophil Activation/Lymphocytes
Innate Immunity/Cell Necrosis (S100A8+S100A12+CLEC4E) - RPL28

3) NK Activation/T cells
Innate Immunity (SLAMF7+KLRC4) - (TMC8+CD3D)

4) B/T Ratio - Adaptive Immune Response (SPIB+CD79B) - (TMC8,CD3D)

5) AF2 - (TFCP2+HNRPF)

6M) TSPAN - (TFCP2+HNRPF)

Females

1) Neutrophil Activation - Apoptosis
Innate Immunity (IL18RAP+TNFAIP6+CASP5) -
(IL8RB+TNFRSF10C+TLR4+KCNE3)

2) Normalized Neutrophil Activation
Innate Immunity/Cell Necrosis (S100A8+S100A12+CLEC4E) -
(NCF4+AQP9)

3) NK Activation/T cells
Innate Immunity (SLAMF7+KLRC4) - (TMC8+CD3D)

4) B/T Ratio - Adaptive Immune Response (SPIB+CD79B) - (TMC8,CD3D)

5) AF2 - (TFCP2+HNRPF)

SEQUENCE LISTING

<160> NUMBER OF SEQ ID NOS: 66

<210> SEQ ID NO 1
<211> LENGTH: 18
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 1
acaggaggga gggatgca                                                    18

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gccaatcacc tgcctaatgc                                                  20

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
tcaggcagcc ccccagag                                                    18

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
acctgagtcc cagactttc act                                               23

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccactacagg aatccaccag aag                                              23

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
cttcagagct ggaaacaa                                                    18

<210> SEQ ID NO 7
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 7
cgagcaacct tgacaagaga tttc                                          24

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggtaaatgtg ctctttgatg ttgaca                                        26

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
cctgtggttt cattttc                                                  17

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cagacgctgc tgatcatcct                                               20

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tcgtaggtgt gatcttcctc cat                                           23

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
ccttgctgtc atccttgtc                                                19

<210> SEQ ID NO 13
<211> LENGTH: 19
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 13
ggacggcaca cctttgaca                                                    19

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cctccagggt agctatgttg ttg                                               23

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
cccagaagct cagagact                                                     18

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
agcctgtgtt tgcttgaaag agat                                              24

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tcttctgctt ctcttaataa tgctcacaa                                         29

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
tcttctgcat acactcctcc                                                   20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
ccccattgtg gtcacaggaa                                                  20

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ccagggcaag ctttctaaac cat                                              23

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
acgttcttac tagtttccc                                                   19

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
tctctaaggc tctatcagtt ctgacat                                          27

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gctggaacca tatatgaaac tacgatact                                        29

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
cctacaaaca cagtgattac a                                                21

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
tgtattggag tactggagca gaaca                            25

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ctgttggaat atgtaatcca ctcctca                          27

<210> SEQ ID NO 27
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
caatgacgtg ctttctg                                     17

<210> SEQ ID NO 28
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ctcccagaag cgcctctt                                    18

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gggacaccgt cagctcatg                                   19

<210> SEQ ID NO 30
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
cacgcagaag gacaact                                     17

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      primer -continued

```
<400> SEQUENCE: 31
tctctaaggg tgagctgaag ca                                              22

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ccaggccttg gaatatttca tcaatg                                          26

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33
caaacaccat caagaatat                                                  19

<210> SEQ ID NO 34
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gaagaaattg ctagagaccg agtgt                                           25

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gcaccatcag tgttgatatc caact                                           25

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36
cacccttttt cctgatatac t                                               21

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
```
agcaaatacg gtttactcca ctgt                                          24

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ggcatcgtga gcagtgagt                                                19

<210> SEQ ID NO 39
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 39
ttttccatct ttttcggtat ttc                                           23

<210> SEQ ID NO 40
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gaggccctcg tggct                                                    15

<210> SEQ ID NO 41
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tggtacaggc gcagctt                                                  17

<210> SEQ ID NO 42
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 42
cttgcgagtc cctgcctc                                                 18

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43 acagaactttcaggaagaagcatgt  25

<210> SEQ ID NO 44
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ccgcactcct acttcagtat gat  23

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 45
acaatgaaag cagaaacc  18

<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gggaagagtg gatgttatca ttgagaa  27

<210> SEQ ID NO 47
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ggatgaacat tcttttctgg gaacct  26

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 48
atgtgtctgg aattaatg  18

<210> SEQ ID NO 49
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
cacaggctcc ggaagca  17

<210> SEQ ID NO 50
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cgcgacaggt cctccac                                                    17

<210> SEQ ID NO 51
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 51
ctggtgtggc aggttc                                                     16

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ggagatgagc ttccagatga cat                                             23

<210> SEQ ID NO 53
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
agctgtcact gaagcatcac ttag                                            24

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 54
catcagtaca ggaaatgtc                                                  19

<210> SEQ ID NO 55
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ggaatgaaaa ctcccccagag atgtg                                          25

<210> SEQ ID NO 56
<211> LENGTH: 25
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 56
caggacgtac aattactgac ttgga                                    25

<210> SEQ ID NO 57
<211> LENGTH: 18
<212> TYPE: DNA
<213> ORGANISM: Artificial Sequence
<220> FEATURE:
<223> OTHER INFORMATION: Description of Artificial Sequence: Synthetic
    probe

<400> SEQUENCE: 57
ctagggcacc tgctacac                                            18

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 58
gccttggaac acaccttcgt                                          20

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 59
caggacacac ttccgatgga ttta                                     24

<210> SEQ ID NO 60
<211> LENGTH: 15
<212> TYPE: DNA
<213> ORGANISM: Artificial Sequence
<220> FEATURE:
<223> OTHER INFORMATION: Description of Artificial Sequence: Synthetic
    probe

<400> SEQUENCE: 60
ccccaggagt tgctg                                               15

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 61
ccagaagtgt ctcccactga ag                                       22

```
<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
ggtgatcttg ggtgtggctt t                                              21

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 63
tttgtggctt aaaaacaacc                                                20

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cggaccacca tcaacaagaa tg                                             22

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
ttcttgcgga tcatgtgtct ga                                             22

<210> SEQ ID NO 66
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 66
ctcgcgccac gctca                                                     15
```

METHOD FOR DETERMINING CORONARY ARTERY DISEASE RISK

CROSS REFERENCE TO RELATED APPLICATIONS

This application claims the benefit of U.S. Provisional Application No. 61/187,203, filed Jun. 15, 2009, and U.S. Provisional Application No. 61/245,190, filed Sep. 23, 2009, the entire disclosures of which are hereby incorporated by reference in their entirety for all purposes.

BACKGROUND

1. Field of the Invention

The invention relates to predictive models for determining the extent of coronary artery disease (CAD) risk based on marker expression measurements, to their methods of use, and to computer systems and software for their implementation.

2. Description of the Related Art

Mortality and morbidity from CAD and myocardial infarction (MI) are a major global health burden. Major determinants of current CAD likelihood are sex, age, and chest-pain type.[1,2] Other risk factors such as diabetes, smoking, dyslipidemia, and family history have been associated with future cardiovascular event risk.[3] In addition, atherosclerosis has a systemic inflammatory component including activation and migration of immune cells into the vessel wall.[4,5] In fact, since such cells are derived from and have interactions with circulating blood, quantitative measurements of circulating blood cell gene expression reflects the extent of CAD.[6,7] These observations likely reflect both changes in cell type distributions, which have prognostic value for cardiovascular events[8] and gene expression changes within a specific cell type or lineage.

The "gold standard" for detecting CAD is invasive coronary angiography; however, this is costly, and can pose risk to the patient. Prior to angiography, non-invasive diagnostic modalities such as myocardial perfusion imaging (MPI) and CT-angiography may be used, however these have complications including radiation exposure, contrast agent sensitivity, and only add moderately to obstructive CAD identification.[9,10]

Unmet Clinical and Scientific Need

A non-invasive blood test that could reliably identify patients with CAD would have significant clinical utility. As such, a major advancement in the fight against atherosclerosis would be the development of non-invasive diagnostic tests that can aid in the diagnosis and assessment of the extent of CAD in patients. Herein the development and validation of an algorithm using marker expression and clinical factors (e.g., age and gender) for such a purpose is described.

SUMMARY

Disclosed herein is a computer-implemented method for scoring a first sample obtained from a subject, including: obtaining a first dataset associated with the first sample, wherein the first dataset includes quantitative expression data for at least one marker set selected from the group consisting of the marker sets in term 1, term 2, term 3, term 4, term 5, term 6, and term 7; wherein term 1 includes marker 1, marker 2, and marker 3, wherein marker 1 includes AF161365, wherein marker 2 includes HNRPF or ACBD5, and wherein marker 3 includes TFCP2 or DDX18; wherein term 2 includes marker 4, marker 5, and marker 6, wherein marker 4 includes AF289562 or CD248, wherein marker 5 includes HNRPF or ACBD5, and wherein marker 6 includes TFCP2 or DDX18; wherein term 3 includes marker 7, marker 8, marker 9, and marker 10 wherein marker 7 includes CD79B or CD19, wherein marker 8 includes SPIB or BLK, wherein marker 9 includes CD3D or LCK, and wherein marker 10 includes TMC8 or CCT2; wherein term 4 includes marker 11, marker 12, marker 13, and marker 14, wherein marker 11 includes S100A12 or MMP9, wherein marker 12 includes CLEC4E or ALOX5AP, wherein marker 13 includes S100A8 or NAMPT, and wherein marker 14 includes RPL28 or SSRP1; wherein term 5 includes marker 15, marker 16, marker 17, marker 18, and marker 19, wherein marker 15 includes S100A12 or MMP9, wherein marker 16 includes CLEC4E or ALOX5AP, wherein marker 17 includes S100A8 or NAMPT, wherein marker 18 includes AQP9 or GLT1D1, and wherein marker 19 includes NCF4 or NCF2; wherein term 6 includes marker 20, marker 21, marker 22, marker 23, marker 24, marker 25, and marker 26, wherein marker 20 includes CASP5 or H3F3B, wherein marker 21 includes IL18RAP or TXN, wherein marker 22 includes TNFAIP6 or PLAUR, wherein marker 23 includes IL8RB or BCL2A1, wherein marker 24 includes TNFRSF10C or PTAFR, wherein marker 25 includes KCNE3 or LAMP2, and wherein marker 26 includes TLR4 or TYROBP; and wherein term 7 includes marker 27, marker 28, marker 29, and marker 30, wherein marker 27 includes SLAMF7 or CX3CR1, wherein marker 28 includes KLRC4 or CD8A, wherein marker 29 includes CD3D or LCK, and wherein marker 30 includes TMC8 or CCT2; and determining, by a computer processor, a first score from the first dataset using an interpretation function, wherein the first score is predictive of CAD in the subject.

In an embodiment, the first dataset includes quantitative expression data for at least two marker sets selected from the group consisting of the marker sets in term 1, term 2, term 3, term 4, term 5, term 6, and term 7. In an embodiment, the first dataset includes quantitative expression data for at least three marker sets selected from the group consisting of the marker sets in term 1, term 2, term 3, term 4, term 5, term 6, and term 7. In an embodiment, the first dataset includes quantitative expression data for at least four marker sets selected from the group consisting of the marker sets in term 1, term 2, term 3, term 4, term 5, term 6, and term 7. In an embodiment, the first dataset includes quantitative expression data for at least five marker sets selected from the group consisting of the marker sets in term 1, term 2, term 3, term 4, term 5, term 6, and term 7. In an embodiment, the first dataset includes quantitative expression data for at least six marker sets selected from the group consisting of the marker sets in term 1, term 2, term 3, term 4, term 5, term 6, and term 7. In an embodiment, the first dataset includes quantitative expression data for the marker sets in term 1, term 2, term 3, term 4, term 5, term 6, and term 7.

In an embodiment, the interpretation function is based on a predictive model. In an embodiment, the predictive model is selected from the group consisting of a partial least squares model, a logistic regression model, a linear regression model, a linear discriminant analysis model, a ridge regression model, and a tree-based recursive partitioning model. In an embodiment, the predictive model performance is characterized by an area under the curve (AUC) ranging from 0.68 to 0.70. In an embodiment, the predictive model performance is characterized by an AUC ranging from 0.70 to 0.79. In an embodiment, the predictive model performance is characterized by an AUC ranging from 0.80 to 0.89. In an embodiment, the predictive model performance is characterized by an AUC ranging from 0.90 to 0.99.

In an embodiment, the first dataset further includes a clinical factor. In an embodiment, the clinical factor is selected from the group consisting of: age, gender, chest pain type, neutrophil count, ethnicity, disease duration, diastolic blood pressure, systolic blood pressure, a family history parameter, a medical history parameter, a medical symptom parameter, height, weight, a body-mass index, resting heart rate, and smoker/non-smoker status.

In an embodiment, the obtaining the first dataset associated with the first sample includes obtaining the first sample and processing the first sample to experimentally determine the first dataset. In an embodiment, the obtaining the first dataset associated with the first sample includes receiving the first dataset from a third party that has processed the first sample to experimentally determine the first dataset.

In an embodiment, the method includes classifying the first sample according to the first score. In an embodiment, the classifying is predictive of the presence or absence of CAD in the subject. In an embodiment, the classifying is predictive of the extent of CAD in the subject. In an embodiment, the classifying is predictive of the risk of CAD in the subject. In an embodiment, the method includes rating CAD risk based on the first score.

In an embodiment, the first sample includes peripheral blood cells. In an embodiment, the peripheral blood cells include leukocytes. In an embodiment, the first sample includes RNA extracted from peripheral blood cells.

In an embodiment, the quantitative expression data are derived from hybridization data. In an embodiment, the quantitative expression data are derived from polymerase chain reaction data. In an embodiment, the quantitative expression data are derived from an antibody binding assay. In an embodiment, the first dataset is obtained stored on a storage memory.

In an embodiment, the subject is a human. In an embodiment, the subject has stable chest pain. In an embodiment, the subject has typical angina or atypical angina or an anginal equivalent. In an embodiment, the subject has no previous diagnosis of myocardial infarction (MI). In an embodiment, the subject has not had a revascularization procedure. In an embodiment, the subject does not have diabetes. In an embodiment, the subject does not have an inflammatory condition or an infectious condition. In an embodiment, the subject is not currently taking a steroid, an immunosuppressive agent, or a chemotherapeutic agent.

Also described herein is a computer-implemented method for scoring a first sample obtained from a subject, including: obtaining a first dataset associated with the first sample, wherein the first dataset includes quantitative expression data for at least two markers selected from the group consisting of AF161365, HNRPF, ACBD5, TFCP2, DDX18, AF289562, CD248, CD79B, CD19, SPIB, BLK, CD3D, LCK, TMC8, CCT2, S100A12, MMP9, CLEC4E, ALOX5AP, S100A8, NAMPT, RPL28, SSRP1, AQP9, GLT1D1, NCF4, NCF2, CASP5, H3F3B, IL18RAP, TXN, TNFAIP6, PLAUR, IL8RB, BCL2A1, TNFRSF10C, PTAFR, KCNE3, LAMP2, TLR4, TYROBP, SLAMF7, CX3CR1, KLRC4, and CD8A; and determining, by a computer processor, a first score from the first dataset using an interpretation function, wherein the first score is predictive of CAD in the subject.

In an embodiment, the first dataset includes a clinical factor. In an embodiment, the clinical factor is age and/or gender. In an embodiment, the clinical factor is selected from the group consisting of: age, gender, chest pain type, neutrophil count, ethnicity, disease duration, diastolic blood pressure, systolic blood pressure, a family history parameter, a medical history parameter, a medical symptom parameter, height, weight, a body-mass index, resting heart rate, and smoker/non-smoker status.

In an embodiment, the first dataset includes quantitative expression data for at least three markers. In an embodiment, the first dataset includes quantitative expression data for at least four markers. In an embodiment, the first dataset includes quantitative expression data for at least five markers. In an embodiment, the first dataset includes quantitative expression data for at least six markers.

In an embodiment, the interpretation function is based on a predictive model. In an embodiment, the predictive model is selected from the group consisting of a partial least squares model, a logistic regression model, a linear regression model, a linear discriminant analysis model, a ridge regression model, and a tree-based recursive partitioning model. In an embodiment, the predictive model performance is characterized by an area under the curve (AUC) ranging from 0.68 to 0.70. In an embodiment, the predictive model performance is characterized by an AUC ranging from 0.70 to 0.79. In an embodiment, the predictive model performance is characterized by an AUC ranging from 0.80 to 0.89. In an embodiment, the predictive model performance is characterized by an AUC ranging from 0.90 to 0.99.

In an embodiment, the obtaining the first dataset associated with the first sample includes obtaining the first sample and processing the first sample to experimentally determine the first dataset. In an embodiment, the obtaining the first dataset associated with the first sample includes receiving the first dataset from a third party that has processed the first sample to experimentally determine the first dataset.

In an embodiment, the method includes classifying the first sample according to the first score. In an embodiment, the classifying is predictive of the presence or absence of CAD in the subject. In an embodiment, the classifying is predictive of the extent of CAD in the subject. In an embodiment, the classifying is predictive of the risk of CAD in the subject. In an embodiment, the method includes rating CAD risk based on the first score.

In an embodiment, the first sample includes peripheral blood cells. In an embodiment, the peripheral blood cells include leukocytes. In an embodiment, the first sample includes RNA extracted from peripheral blood cells.

In an embodiment, the quantitative expression data are derived from hybridization data. In an embodiment, the quantitative expression data are derived from polymerase chain reaction data. In an embodiment, the quantitative expression data are derived from an antibody binding assay. In an embodiment, the first dataset is obtained stored on a storage memory.

In an embodiment, the subject is a human. In an embodiment, the subject has stable chest pain. In an embodiment, the subject has typical angina or atypical angina or an anginal equivalent. In an embodiment, the subject has no previous diagnosis of myocardial infarction (MI). In an embodiment, the subject has not had a revascularization procedure. In an embodiment, the subject does not have diabetes. In an embodiment, the subject does not have an inflammatory condition or an infectious condition. In an embodiment, the subject is not currently taking a steroid, an immunosuppressive agent, or a chemotherapeutic agent.

Also described herein is a system for predicting CAD in a subject, the system including: a storage memory for storing a dataset associated with a sample obtained from the subject, wherein the first dataset includes quantitative expression data for at least one marker set selected from the group consisting of the marker sets in term 1, term 2, term 3, term 4, term 5, term 6, and term 7; wherein term 1 includes marker 1, marker 2, and marker 3, wherein marker 1 includes AF161365, wherein marker 2 includes HNRPF or ACBD5, and wherein marker 3 includes TFCP2 or DDX18; wherein term 2 includes marker 4, marker 5, and marker 6, wherein marker 4 includes AF289562 or CD248, wherein marker 5 includes HNRPF or ACBD5, and wherein marker 6 includes TFCP2 or DDX18; wherein term 3 includes marker 7, marker 8, marker 9, and marker 10 wherein marker 7 includes CD79B or CD19, wherein marker 8 includes SPIB or BLK, wherein marker 9 includes CD3D or LCK, and wherein marker 10 includes TMC8 or CCT2; wherein term 4 includes marker 11, marker 12, marker 13, and marker 14, wherein marker 11 includes S100A12 or MMP9, wherein marker 12 includes CLEC4E or ALOX5AP, wherein marker 13 includes S100A8 or NAMPT, and wherein marker 14 includes RPL28 or SSRP1; wherein term 5 includes marker 15, marker 16, marker 17, marker 18, and marker 19, wherein marker 15 includes S100A12 or MMP9, wherein marker 16 includes CLEC4E or ALOX5AP, wherein marker 17 includes S100A8 or NAMPT, wherein marker 18 includes AQP9 or GLT1D1, and wherein marker 19 includes NCF4 or NCF2; wherein term 6 includes marker 20, marker 21, marker 22, marker 23, marker 24, marker 25, and marker 26, wherein marker 20 includes CASP5 or H3F3B, wherein marker 21 includes IL18RAP or TXN, wherein marker 22 includes TNFAIP6 or PLAUR, wherein marker 23 includes IL8RB or BCL2A1, wherein marker 24 includes TNFRSF10C or PTAFR, wherein marker 25 includes KCNE3 or LAMP2, and wherein marker 26 includes TLR4 or TYROBP; and wherein term 7 includes marker 27, marker 28, marker 29, and marker 30, wherein marker 27 includes SLAMF7 or CX3CR1, wherein marker 28 includes KLRC4 or CD8A, wherein marker 29 includes CD3D or LCK, and wherein marker 30 includes TMC8 or CCT2; and a processor communicatively coupled to the storage memory for determining a score with an interpretation function wherein the score is predictive of CAD in the subject.

Also described herein is a computer-readable storage medium storing computer-executable program code, the program code including: program code for storing a dataset associated with a sample obtained from the subject, wherein the first dataset includes quantitative expression data for at least one marker set selected from the group consisting of the marker sets in term 1, term 2, term 3, term 4, term 5, term 6, and term 7; wherein term 1 includes marker 1, marker 2, and marker 3, wherein marker 1 includes AF161365, wherein marker 2 includes HNRPF or ACBD5, and wherein marker 3 includes TFCP2 or DDX18; wherein term 2 includes marker 4, marker 5, and marker 6, wherein marker 4 includes AF289562 or CD248, wherein marker 5 includes HNRPF or ACBD5, and wherein marker 6 includes TFCP2 or DDX18; wherein term 3 includes marker 7, marker 8, marker 9, and marker 10 wherein marker 7 includes CD79B or CD19, wherein marker 8 includes SPIB or BLK, wherein marker 9 includes CD3D or LCK, and wherein marker 10 includes TMC8 or CCT2; wherein term 4 includes marker 11, marker 12, marker 13, and marker 14, wherein marker 11 includes S100A12 or MMP9, wherein marker 12 includes CLEC4E or ALOX5AP, wherein marker 13 includes S100A8 or NAMPT, and wherein marker 14 includes RPL28 or SSRP1; wherein term 5 includes marker 15, marker 16, marker 17, marker 18, and marker 19, wherein marker 15 includes S100A12 or MMP9, wherein marker 16 includes CLEC4E or ALOX5AP, wherein marker 17 includes S100A8 or NAMPT, wherein marker 18 includes AQP9 or GLT1D1, and wherein marker 19 includes NCF4 or NCF2; wherein term 6 includes marker 20, marker 21, marker 22, marker 23, marker 24, marker 25, and marker 26, wherein marker 20 includes CASP5 or H3F3B, wherein marker 21 includes IL18RAP or TXN, wherein marker 22 includes TNFAIP6 or PLAUR, wherein marker 23 includes IL8RB or BCL2A1, wherein marker 24 includes TNFRSF10C or PTAFR, wherein marker 25 includes KCNE3 or LAMP2, and wherein marker 26 includes TLR4 or TYROBP; and wherein term 7 includes marker 27, marker 28, marker 29, and marker 30, wherein marker 27 includes SLAMF7 or CX3CR1, wherein marker 28 includes KLRC4 or CD8A, wherein marker 29 includes CD3D or LCK, and wherein marker 30 includes TMC8 or CCT2; and program code for determining a score with an interpretation function wherein the score is predictive of CAD in the subject.

Also described herein is a method for predicting CAD in a subject, including: obtaining a sample from the subject, wherein the sample includes a plurality of analytes; contacting the sample with a reagent; generating a plurality of complexes between the reagent and the plurality of analytes; detecting the plurality of complexes to obtain a dataset associated with the sample, wherein the first dataset includes quantitative expression data for at least one marker set selected from the group consisting of the marker sets in term 1, term 2, term 3, term 4, term 5, term 6, and term 7; wherein term 1 includes marker 1, marker 2, and marker 3, wherein marker 1 includes AF161365, wherein marker 2 includes HNRPF or ACBD5, and wherein marker 3 includes TFCP2 or DDX18; wherein term 2 includes marker 4, marker 5, and marker 6, wherein marker 4 includes AF289562 or CD248, wherein marker 5 includes HNRPF or ACBD5, and wherein marker 6 includes TFCP2 or DDX18; wherein term 3 includes marker 7, marker 8, marker 9, and marker 10 wherein marker 7 includes CD79B or CD19, wherein marker 8 includes SPIB or BLK, wherein marker 9 includes CD3D or LCK, and wherein marker 10 includes TMC8 or CCT2; wherein term 4 includes marker 11, marker 12, marker 13, and marker 14, wherein marker 11 includes S100A12 or MMP9, wherein marker 12 includes CLEC4E or ALOX5AP, wherein marker 13 includes S100A8 or NAMPT, and wherein marker 14 includes RPL28 or SSRP1; wherein term 5 includes marker 15, marker 16, marker 17, marker 18, and marker 19, wherein marker 15 includes S100A12 or MMP9, wherein marker 16 includes CLEC4E or ALOX5AP, wherein marker 17 includes S100A8 or NAMPT, wherein marker 18 includes AQP9 or GLT1D1, and wherein marker 19 includes NCF4 or NCF2; wherein term 6 includes marker 20, marker 21, marker 22, marker 23, marker 24, marker 25, and marker 26, wherein marker 20 includes CASP5 or H3F3B, wherein marker 21 includes IL18RAP or TXN, wherein marker 22 includes TNFAIP6 or PLAUR, wherein marker 23 includes IL8RB or BCL2A1, wherein marker 24 includes TNFRSF10C or PTAFR, wherein marker 25 includes KCNE3 or LAMP2, and wherein marker 26 includes TLR4 or TYROBP; and wherein term 7 includes marker 27, marker 28, marker 29, and marker 30, wherein marker 27 includes SLAMF7 or CX3CR1, wherein marker 28 includes KLRC4 or CD8A, wherein marker 29 includes CD3D or LCK, and wherein marker 30 includes TMC8 or CCT2; and determining a score from the dataset using an interpretation function, wherein the score is predictive of CAD in the subject.

Also described herein is a kit for predicting CAD in a subject, including: a set of reagents including a plurality of reagents for determining from a sample obtained from the subject quantitative expression data for at least one marker set selected from the group consisting of the marker sets in term 1, term 2, term 3, term 4, term 5, term 6, and term 7; wherein term 1 includes marker 1, marker 2, and marker 3, wherein marker 1 includes AF161365, wherein marker 2 includes HNRPF or ACBD5, and wherein marker 3 includes TFCP2 or DDX18; wherein term 2 includes marker 4, marker 5, and marker 6, wherein marker 4 includes AF289562 or CD248, wherein marker 5 includes HNRPF or ACBD5, and wherein marker 6 includes TFCP2 or DDX18; wherein term 3 includes marker 7, marker 8, marker 9, and marker 10 wherein marker 7 includes CD79B or CD19, wherein marker 8 includes SPIB or BLK, wherein marker 9 includes CD3D or LCK, and wherein marker 10 includes TMC8 or CCT2; wherein term 4 includes marker 11, marker 12, marker 13, and marker 14, wherein marker 11 includes S100A12 or MMP9, wherein marker 12 includes CLEC4E or ALOX5AP, wherein marker 13 includes S100A8 or NAMPT, and wherein marker 14 includes RPL28 or SSRP1; wherein term 5 includes marker 15, marker 16, marker 17, marker 18, and marker 19, wherein marker 15 includes S100A12 or MMP9, wherein marker 16 includes CLEC4E or ALOX5AP, wherein marker 17 includes S100A8 or NAMPT, wherein marker 18 includes AQP9 or GLT1D1, and wherein marker 19 includes NCF4 or NCF2; wherein term 6 includes marker 20, marker 21, marker 22, marker 23, marker 24, marker 25, and marker 26, wherein marker 20 includes CASP5 or H3F3B, wherein marker 21 includes IL18RAP or TXN, wherein marker 22 includes TNFAIP6 or PLAUR, wherein marker 23 includes IL8RB or BCL2A1, wherein marker 24 includes TNFRSF10C or PTAFR, wherein marker 25 includes KCNE3 or LAMP2, and wherein marker 26 includes TLR4 or TYROBP; and wherein term 7 includes marker 27, marker 28, marker 29, and marker 30, wherein marker 27 includes SLAMF7 or CX3CR1, wherein marker 28 includes KLRC4 or CD8A, wherein marker 29 includes CD3D or LCK, and wherein marker 30 includes TMC8 or CCT2; and instructions for using the plurality of reagents to determine quantitative data from the sample, wherein the instructions include instructions for determining a score from the dataset wherein the score is predictive of CAD in the subject.

In an embodiment, the instructions include instructions for conducting a microarray assay. In an embodiment, the instructions include instructions for conducting a polymerase chain reaction assay.

Also described herein is a system for predicting CAD in a subject, the system including: a storage memory for storing a dataset associated with a sample obtained from the subject, wherein the dataset includes quantitative expression data for at least two markers selected from the group consisting of AF161365, HNRPF, ACBD5, TFCP2, DDX18, AF289562, CD248, CD79B, CD19, SPIB, BLK, CD3D, LCK, TMC8, CCT2, S100A12, MMP9, CLEC4E, ALOX5AP, S100A8, NAMPT, RPL28, SSRP1, AQP9, GLT1D1, NCF4, NCF2, CASP5, H3F3B, IL18RAP, TXN, TNFAIP6, PLAUR, IL8RB, BCL2A1, TNFRSF10C, PTAFR, KCNE3, LAMP2, TLR4, TYROBP, SLAMF7, CX3CR1, KLRC4, and CD8A; and a processor communicatively coupled to the storage memory for determining a score with an interpretation function wherein the score is predictive of CAD in the subject.

Also described herein is a computer-readable storage medium storing computer-executable program code, the program code including: program code for storing a dataset associated with a sample obtained from the subject, wherein the dataset includes quantitative expression data for at least two markers selected from the group consisting of AF161365, HNRPF, ACBD5, TFCP2, DDX18, AF289562, CD248, CD79B, CD19, SPIB, BLK, CD3D, LCK, TMC8, CCT2, S100A12, MMP9, CLEC4E, ALOX5AP, S100A8, NAMPT, RPL28, SSRP1, AQP9, GLT1D1, NCF4, NCF2, CASP5, H3F3B, IL18RAP, TXN, TNFAIP6, PLAUR, IL8RB, BCL2A1, TNFRSF10C, PTAFR, KCNE3, LAMP2, TLR4, TYROBP, SLAMF7, CX3CR1, KLRC4, and CD8A; and program code for determining a score with an interpretation function wherein the score is predictive of CAD in the subject.

Also described herein is a method for predicting CAD in a subject, including: obtaining a sample from the subject, wherein the sample includes a plurality of analytes; contacting the sample with a reagent; generating a plurality of complexes between the reagent and the plurality of analytes; detecting the plurality of complexes to obtain a dataset associated with the sample, wherein the dataset includes quantitative expression data for at least two markers selected from the group consisting of AF161365, HNRPF, ACBD5, TFCP2, DDX18, AF289562, CD248, CD79B, CD19, SPIB, BLK, CD3D, LCK, TMC8, CCT2, S100A12, MMP9, CLEC4E, ALOX5AP, S100A8, NAMPT, RPL28, SSRP1, AQP9, GLT1D1, NCF4, NCF2, CASP5, H3F3B, IL18RAP, TXN, TNFAIP6, PLAUR, IL8RB, BCL2A1, TNFRSF10C, PTAFR, KCNE3, LAMP2, TLR4, TYROBP, SLAMF7, CX3CR1, KLRC4, and CD8A; and determining a score from the dataset using an interpretation function, wherein the score is predictive of CAD in the subject.

Also described herein is a kit for predicting CAD in a subject, including: a set of reagents including a plurality of reagents for determining from a sample obtained from the subject quantitative expression data for at least two markers selected from the group consisting of AF161365, HNRPF, ACBD5, TFCP2, DDX18, AF289562, CD248, CD79B, CD19, SPIB, BLK, CD3D, LCK, TMC8, CCT2, S100A12, MMP9, CLEC4E, ALOX5AP, S100A8, NAMPT, RPL28, SSRP1, AQP9, GLT1D1, NCF4, NCF2, CASP5, H3F3B, IL18RAP, TXN, TNFAIP6, PLAUR, IL8RB, BCL2A1, TNFRSF10C, PTAFR, KCNE3, LAMP2, TLR4, TYROBP, SLAMF7, CX3CR1, KLRC4, and CD8A; and instructions for using the plurality of reagents to determine quantitative data from the sample, wherein the instructions include instructions for determining a score from the dataset, wherein the score is predictive of CAD in the subject.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 5—Schematic of the Algorithm Structure and Genes. The algorithm consists of overlapping gene expression functions for males and females with a sex-specific linear age function for the former and a non-linear age function for the latter. For the gene expression components, 16/23 genes in 4 terms are gender independent: Term 1—neutrophil activation and apoptosis, Term 3—NK cell activation to T cell ratio, Term 4, B to T cell ratio, and Term 5—AF289562 expression normalized to TFCP2 and HNRPF. In addition, Term 2 consists of 3 sex-independent neutrophil/innate immunity genes (S100A8, S100A12, CLEC4E) normalized to overall neutrophil gene expression (AQP9, NCF4) for females and to RPL28 (lymphocytes) for males. The final male specific term is the normalized expression of TSPAN16. Algorithm score is defined as $1.821-0.755*\text{Term}1-0.406*\text{Term}3-0.308*\text{Term}2*\text{Sex}-0.137*\text{Term}4-0.548*\text{Term}2*(1-\text{Sex})-0.246*\text{Term}5-0.481*\text{Term}6*\text{Sex}+0.851*\text{Sex}+0.045*\text{Sex}*\text{Age}+0.123*(1-\text{Sex})*\max(0,\text{Age}-55)$, where Sex is a 0/1 indicator of sex (0=female, 1=male) and age is in years, and is calculated as described (Methods Section below).

DETAILED DESCRIPTION

Definitions

Figure 1:
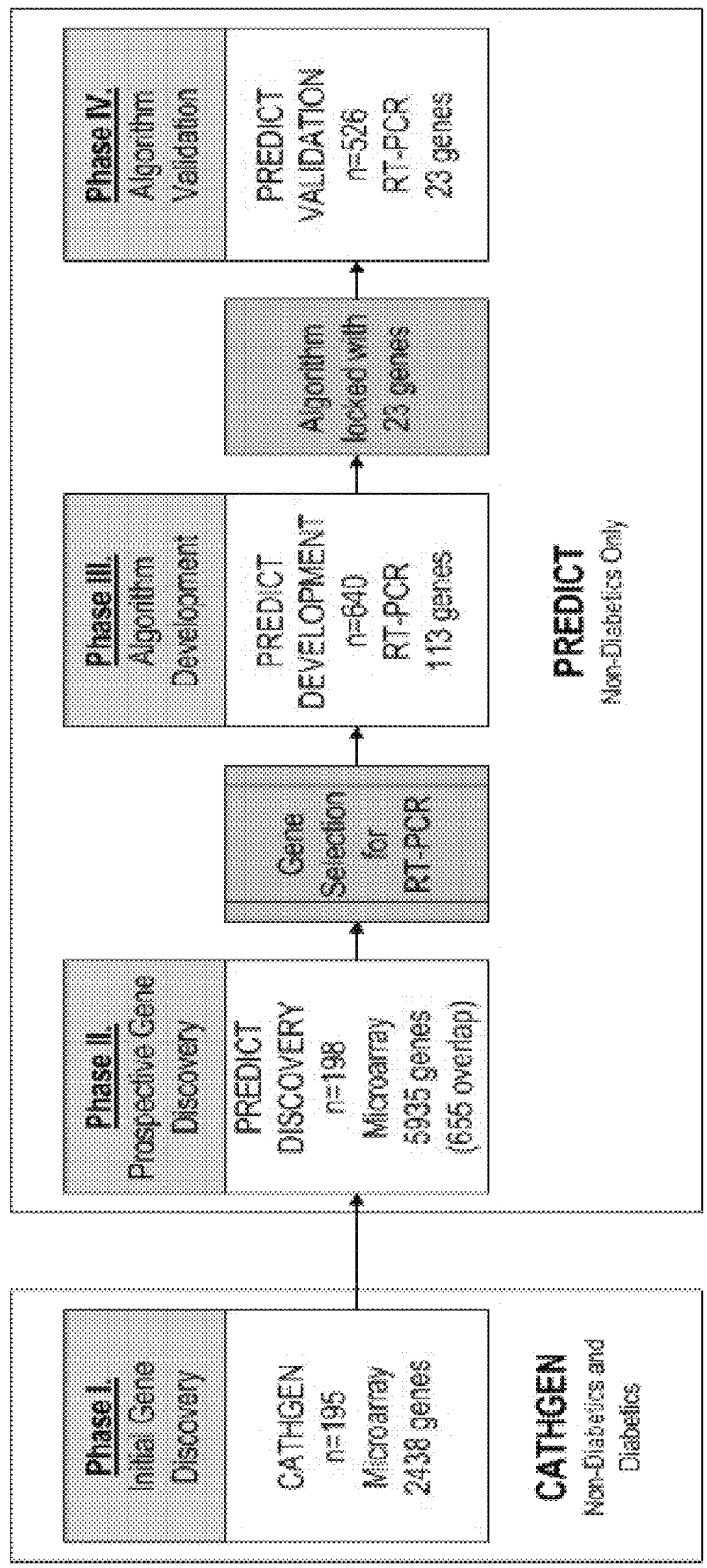
FIG. 1—Gene Discovery, Algorithm Development, and Validation Patient and Logic Flow Schematic. Initial gene discovery (CATHGEN repository) included both diabetic and non-diabetic patients. Gene discovery from Personalized Risk Evaluation and Diagnosis in the Coronary Tree (PREDICT) involved non-diabetic patients in a paired microarray analysis, that yielded 655 significant genes in common with those from the CATHGEN arrays. For RT-PCR 113 genes were selected and tested on 640 PREDICT patient samples, from which the final algorithm was derived and locked, followed by validation in the PREDICT validation cohort (N=526).

In general, terms used in the claims and the specification are intended to be construed as having the plain meaning understood by a person of ordinary skill in the art. Certain terms are defined below to provide additional clarity. In case of conflict between the plain meaning and the provided definitions, the provided definitions are to be used.

The term "acute coronary syndrome" encompasses all forms of unstable coronary artery disease.

The term "coronary artery disease" or "CAD" encompasses all forms of atherosclerotic disease affecting the coronary arteries.

The term "Ct" refers to cycle threshold and is defined as the PCR cycle number where the fluorescent value is above a set threshold. Therefore, a low Ct value corresponds to a high level of expression, and a high Ct value corresponds to a low level of expression.

The term "Cp" refers to the crossing point and is defined as the intersection of the best fit of the log-linear portion of a standard's amplification curve in a real time PCR instrument such as, e.g., a LightCycler, and the noise band (set according to background fluorescence measurements).

The term "FDR" means to false discovery rate. FDR can be estimated by analyzing randomly-permuted datasets and tabulating the average number of genes at a given p-value threshold.

The terms "GL" "GM" and "GU" respectively refer to 1st percentile, median, and 99th percentile of Cp for that gene in the Algorithm Development data set.

The terms "marker" or "markers" encompass, without limitation, lipids, lipoproteins, proteins, cytokines, chemokines, growth factors, peptides, nucleic acids, genes, and oligonucleotides, together with their related complexes, metabolites, mutations, variants, polymorphisms, modifications, fragments, subunits, degradation products, elements, and other analytes or sample-derived measures. A marker can also include mutated proteins, mutated nucleic acids, variations in copy numbers, and/or transcript variants, in circumstances in which such mutations, variations in copy number and/or transcript variants are useful for generating a predictive model, or are useful in predictive models developed using related markers (e.g., non-mutated versions of the proteins or nucleic acids, alternative transcripts, etc.).

The terms "highly correlated gene expression" or "highly correlated marker expression" refer to gene or marker expression values that have a sufficient degree of correlation to allow their interchangeable use in a predictive model of coronary artery disease. For example, if gene x having expression value X is used to construct a predictive model, highly correlated gene y having expression value Y can be substituted into the predictive model in a straightforward way readily apparent to those having ordinary skill in the art and the benefit of the instant disclosure. Assuming an approximately linear relationship between the expression values of genes x and y such that $Y=a+bX$, then X can be substituted into the predictive model with $(Y-a)/b$. For non-linear correlations, similar mathematical transformations can be used that effectively convert the expression value of gene y into the corresponding expression value for gene x. The terms "highly correlated marker" or "highly correlated substitute marker" refer to markers that can be substituted into and/or added to a predictive model based on, e.g., the above criteria. A highly correlated marker can be used in at least two ways: (1) by substitution of the highly correlated marker(s) for the original marker(s) and generation of a new model for predicting CAD risk; or (2) by substitution of the highly correlated marker(s) for the original marker(s) in the existing model for predicting CAD risk.

The term "mammal" encompasses both humans and non-humans and includes but is not limited to humans, non-human primates, canines, felines, murines, bovines, equines, and porcines.

The term "metagene" refers to a set of genes whose expression values are combined to generate a single value that can be used as a component in a predictive model. (Brunet, J. P., et al. Proc. Natl. Acad. Sciences 2004; 101(12):4164-9)

The term "myocardial infarction" refers to an ischemic myocardial necrosis. This is usually the result of abrupt reduction in coronary blood flow to a segment of the myocardium, the muscular tissue of the heart. Myocardial infarction can be classified into ST-elevation and non-ST elevation MI (also referred to as unstable angina). Myocardial necrosis results in either classification. Myocardial infarction, of either ST-elevation or non-ST elevation classification, is an unstable form of atherosclerotic cardiovascular disease.

The term "sample" can include a single cell or multiple cells or fragments of cells or an aliquot of body fluid, taken from a subject, by means including venipuncture, excretion, ejaculation, massage, biopsy, needle aspirate, lavage sample, scraping, surgical incision, or intervention or other means known in the art.

The term "subject" encompasses a cell, tissue, or organism, human or non-human, whether in vivo, ex vivo, or in vitro, male or female.

The term "obtaining a dataset associated with a sample" encompasses obtaining a set of data determined from at least one sample. Obtaining a dataset encompasses obtaining a sample, and processing the sample to experimentally determine the data. The phrase also encompasses receiving a set of data, e.g., from a third party that has processed the sample to experimentally determine the dataset. Additionally, the phrase encompasses mining data from at least one database or at least one publication or a combination of databases and publications. A dataset can be obtained by one of skill in the art via a variety of known ways including stored on a storage memory.

The term "clinical factor" refers to a measure of a condition of a subject, e.g., disease activity or severity. "Clinical factor" encompasses all markers of a subject's health status, including non-sample markers, and/or other characteristics of a subject, such as, without limitation, age and gender. A clinical factor can be a score, a value, or a set of values that can be obtained from evaluation of a sample (or population of samples) from a subject or a subject under a determined condition. A clinical factor can also be predicted by markers and/or other parameters such as gene expression surrogates.

It must be noted that, as used in the specification and the appended claims, the singular forms "a," "an," and "the" include plural referents unless the context clearly dictates otherwise.

Methods

Markers and Clinical Factors

The quantity of one or more markers of the invention can be indicated as a value. A value can be one or more numerical values resulting from evaluation of a sample under a condition. The values can be obtained, for example, by experimentally obtaining measures from a sample by an assay performed in a laboratory, or alternatively, obtaining a dataset from a service provider such as a laboratory, or from a database or a server on which the dataset has been stored, e.g., on a storage memory.

In an embodiment, the quantity of one or more markers can be one or more numerical values associated with expression levels of: AF161365, HNRPF, ACBD5, TFCP2, DDX18, AF289562, CD248, HNRPF, ACBD5, TFCP2, DDX18, CD79B, CD19, SPIB, BLK, CD3D, LCK, TMC8, CCT2, S100A12, MMP9, CLEC4E, ALOX5AP, S100A8, NAMPT, RPL28, SSRP1, S100A12, MMP9, CLEC4E, ALOX5AP, S100A8, NAMPT, AQP9, GLT1D1, NCF4, NCF2, CASP5, H3F3B, IL18RAP, TXN, TNFAIP6, PLAUR, IL8RB, BCL2A1, TNFRSF10C, PTAFR, KCNE3, LAMP2, TLR4, TYROBP, SLAMF7, CX3CR1, KLRC4, CD8A, CD3D, LCK, TMC8, or CCT2; resulting from evaluation of a sample under a condition. This nomenclature is used to refer to human genes in accordance with guidelines provided by the Human Genome Organisation (HUGO) Gene Nomenclature Committee (HGNC). Further information about each human gene, such as accession number(s) and aliases, can be found by entering the gene name into the search page on the HGNC Search genenames.org website. For example, entering the term "CD3D" into the Simple Search field of the HGNC website on Jun. 1, 2010 returns the approved gene name of CD3D (CD3d molecule, delta (CD3-TCR complex)), the sequence accession IDs of CD3D (X01451; NM_000732), and the previous symbols of CD3D (T3D). Further human gene names are provided in the Examples section below.

In an embodiment, a condition can include one clinical factor or a plurality of clinical factors. In an embodiment, a clinical factor can be included within a dataset. A dataset can include one or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty-one or more, twenty-two or more, twenty-three or more, twenty-four or more, twenty-five or more, twenty-six or more, twenty-seven or more, twenty-eight or more, twenty-nine or more, or thirty or more overlapping or distinct clinical factor(s). A clinical factor can be, for example, the condition of a subject in the presence of a disease or in the absence of a disease. Alternatively, or in addition, a clinical factor can be the health status of a subject. Alternatively, or in addition, a clinical factor can be age, gender, chest pain type, neutrophil count, ethnicity, disease duration, diastolic blood pressure, systolic blood pressure, a family history parameter, a medical history parameter, a medical symptom parameter, height, weight, a body-mass index, resting heart rate, and smoker/non-smoker status. Clinical factors can include whether the subject has stable chest pain, whether the subject has typical angina, whether the subject has atypical angina, whether the subject has an anginal equivalent, whether the subject has been previously diagnosed with MI, whether the subject has had a revascularization procedure, whether the subject has diabetes, whether the subject has an inflammatory condition, whether the subject has an infectious condition, whether the subject is taking a steroid, whether the subject is taking an immunosuppressive agent, and/or whether the subject is taking a chemotherapeutic agent. Other examples of clinical factors are listed in the Tables and Figures.

In an embodiment, a marker's associated value can be included in a dataset associated with a sample obtained from a subject. A dataset can include the marker expression value of two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty-one or more, twenty-two or more, twenty-three or more, twenty-four or more, twenty-five or more, twenty-six or more, twenty-seven or more, twenty-eight or more, twenty-nine or more, or thirty or more marker(s). For example, a dataset can include the expression values for AF161365, HNRPF, ACBD5; AF161365, HNRPF; or AF161365, ACBD5. Other combinations are described in more detail in the Examples section below.

In an embodiment, one or more markers can be divided into terms. Terms can include one marker, but generally include three or more markers. Terms can be included in a dataset associated with a sample obtained from a subject. The dataset can include one or more terms, two or more terms, three or more terms, four or more terms, five or more terms, six or more terms, seven or more terms, eight or more terms, nine or more terms, or ten or more terms. In an embodiment, a term can include one or more, two or more, three or more, four or more, five or more, six or more, seven or more, eight or more, nine or more, ten or more, eleven or more, twelve or more, thirteen or more, fourteen or more, fifteen or more, sixteen or more, seventeen or more, eighteen or more, nineteen or more, twenty or more, twenty-one or more, twenty-two or more, twenty-three or more, twenty-four or more, twenty-five or more, twenty-six or more, twenty-seven or more, twenty-eight or more, twenty-nine or more, or thirty or more marker(s). In an embodiment, the markers are divided into seven distinct terms: term 1, term 2, term 3, term 4, term 5, term 6, and term 7. In an embodiment, term 1 can include marker 1, marker 2, and marker 3, where marker 1 includes AF161365, where marker 2 includes HNRPF or ACBD5, and where marker 3 includes TFCP2 or DDX18. In an embodiment, term 2 can include marker 4, marker 5, and marker 6, where marker 4 includes AF289562 or CD248, where marker 5 includes HNRPF or ACBD5, and where marker 6 includes TFCP2 or DDX18. In an embodiment, term 3 can include marker 7, marker 8, marker 9, and marker 10 where marker 7 includes CD79B or CD19, where marker 8 includes SPIB or BLK, where marker 9 includes CD3D or LCK, and where marker 10 includes TMC8 or CCT2. In an embodiment, term 4 can include marker 11, marker 12, marker 13, and marker 14, where marker 11 includes S100A12 or MMP9, where marker 12 includes CLEC4E or ALOX5AP, where marker 13 includes S100A8 or NAMPT, and where marker 14 includes RPL28 or SSRP1. In an embodiment, term 5 can include marker 15, marker 16, marker 17, marker 18, and marker 19, where marker 15 includes S100A12 or MMP9, where marker 16 includes CLEC4E or ALOX5AP, where marker 17 includes S100A8 or NAMPT, where marker 18 includes AQP9 or GLT1D1, and where marker 19 includes NCF4 or NCF2. In an embodiment, term 6 can include marker 20, marker 21, marker 22, marker 23, marker 24, marker 25, and marker 26, where marker 20 includes CASP5 or H3F3B, where marker 21 includes IL18RAP or TXN, where marker 22 includes TNFAIP6 or PLAUR, where marker 23 includes IL8RB or BCL2A1, where marker 24 includes TNERSF10C or PTAFR, where marker 25 includes KCNE3 or LAMP2, and where marker 26 includes TLR4 or TYROBP. In an embodiment, term 7 can include marker 27, marker 28, marker 29, and marker 30, where marker 27 includes SLAMF7 or CX3CR1, where marker 28 includes KLRC4 or CD8A, where marker 29 includes CD3D or LCK, and where marker 30 includes TMC8 or CCT2.

In another embodiment, the invention includes obtaining a sample associated with a subject, where the sample includes one or more markers. The sample can be obtained by the subject or by a third party, e.g., a medical professional. Examples of medical professionals include physicians, emergency medical technicians, nurses, first responders, psychologists, medical physics personnel, nurse practitioners, surgeons, dentists, and any other obvious medical professional as would be known to one skilled in the art. A sample can include peripheral blood cells, isolated leukocytes, or RNA extracted from peripheral blood cells or isolated leukocytes. The sample can be obtained from any bodily fluid, for example, amniotic fluid, aqueous humor, bile, lymph, breast milk, interstitial fluid, blood, blood plasma, cerumen (earwax), Cowper's fluid (pre-ejaculatory fluid), chyle, chyme, female ejaculate, menses, mucus, saliva, urine, vomit, tears, vaginal lubrication, sweat, serum, semen, sebum, pus, pleural fluid, cerebrospinal fluid, synovial fluid, intracellular fluid, and vitreous humour. In an example, the sample is obtained by a blood draw, where the medical professional draws blood from a subject, such as by a syringe. The bodily fluid can then be tested to determine the value of one or more markers using an assay. The value of the one or more markers can then be evaluated by the same party that performed the assay using the methods of the invention or sent to a third party for evaluation using the methods of the invention.

Interpretation Functions

In an embodiment, an interpretation function can be a function produced by a predictive model. An interpretation function can also be produced by a plurality of predictive models. In an embodiment, an interpretation function can include terms $Norm_1$, $Norm_2$, $NK_{up}$, $T_{cell}$, $B_{cell}$, Neut, $N_{up}$, $N_{down}$, $SCA_1$, $AF_2$, TSPAN, SEX, and INTERCEPT. In a related embodiment, $Norm_1$=RPL28, $Norm_2$=(0.5*HNRPF+ 0.5*TFCP2), $NK_{up}$=(0.5*SLAMF7+0.5*KLRC4), $T_{cell}$= (0.5*CD3D+0.5*TMC8), $B_{cell}$=(⅔*CD79B+⅓*SPB3), Neut=(0.5*AQP9+0.5*NCF4), $N_{up}$=(⅓*CASP5+ ⅓*IL18RAP+⅓*TNFAIP6), $N_{down}$=(0.25*IL8RB+ 0.25*TNFRSF10C+0.25*TLR4+0.25*KCNE3), $SCA_1$= (⅓*S100A12+1/3*CLEC4E+⅓*S100A8), $AF_2$=AF289562, TSPAN=1 if (AF161365-$Norm_2$>6.27 or AF161365=NoCall), 0 otherwise, SEX=1 for Males, 0 for Females. In a related embodiment, for Males, INTERCEPT=Intercept+SEX+MAGE*Age, with Age in years, and for Females, INTERCEPT=Intercept+ OFAGE2*max(0,Age-60), with Age in years. In a related embodiment, coefficients Intercept=1.82120871, SEX=0.851181, OFAGE2=0.123283, MAGE=0.044868, TSPAN=−0.48182, AF2=−0.24592, Bcell=−0.13717, SCA1M=−0.30754, NeutF=−0.54778, Nupdown=−0.75514, and NK=−0.40579. In a related embodiment, a score is determined according to INTERCEPT−Nupdown*($N_{up}$−$N_{down}$)− NK*($NK_{up}$−$T_{cell}$)−SCA1M*SEX*($SCA_1$−$Norm_1$)−Bcell* ($B_{cell}$−$T_{cell}$)−NeutF*(1−SEX)*($SCA_1$−Neut)− TSPANcoef*SEX*(TSPAN)−AF2*($AF_2$−$Norm_2$). In an embodiment, an interpretation function can include any linear combination of age, gender (i.e., sex), and one or more terms.

In an embodiment, a predictive model can include a partial least squares model, a logistic regression model, a linear regression model, a linear discriminant analysis model, a ridge regression model, and a tree-based recursive partitioning model. In an embodiment, a predictive model can also include Support Vector Machines, quadratic discriminant analysis, or a LASSO regression model. See Elements of Statistical Learning, Springer 2003, Hastie, Tibshirani, Friedman; which is herein incorporated by reference in its entirety for all purposes. Predictive model performance can be characterized by an area under the curve (AUC). In an embodiment, predictive model performance is characterized by an AUC ranging from 0.68 to 0.70. In an embodiment, predictive model performance is characterized by an AUC ranging from 0.70 to 0.79. In an embodiment, predictive model performance is characterized by an AUC ranging from 0.80 to 0.89. In an embodiment, predictive model performance is characterized by an AUC ranging from 0.90 to 0.99.

Assays

Examples of assays for one or more markers include DNA assays, microarrays, polymerase chain reaction (PCR), RT-PCR, Southern blots, Northern blots, antibody-binding assays, enzyme-linked immunosorbent assays (ELISAs), flow cytometry, protein assays, Western blots, nephelometry, turbidimetry, chromatography, mass spectrometry, immunoassays, including, by way of example, but not limitation, RIA, immunofluorescence, immunochemiluminescence, immunoelectrochemiluminescence, or competitive immunoassays, immunoprecipitation, and the assays described in the Examples section below. The information from the assay can be quantitative and sent to a computer system of the invention. The information can also be qualitative, such as observing patterns or fluorescence, which can be translated into a quantitative measure by a user or automatically by a reader or computer system. In an embodiment, the subject can also provide information other than assay information to a computer system, such as race, height, weight, age, gender, eye color, hair color, family medical history and any other information that may be useful to a user, such as a clinical factor described above.

Informative Marker Groups

In addition to the specific, exemplary markers identified in this application by name, accession number, or sequence, included within the scope of the invention are all operable predictive models of CAD and methods for their use to score and optionally classify samples using expression values of variant sequences having at least 90% or at least 95% or at least 97% or greater identity to the exemplified sequences or that encode proteins having sequences with at least 90% or at least 95% or at least 97% or greater identity to those encoded by the exemplified genes or sequences. The percentage of sequence identity may be determined using algorithms well known to those of ordinary skill in the art, including, e.g., BLASTn, and BLASTp, as described in Stephen F. Altschul et al., J. Mol. Biol. 215:403-410 (1990) and available at the National Center for Biotechnology Information website maintained by the National Institutes of Health. As described below, in accordance with an embodiment of the present invention, are all operable predictive models and methods for their use in scoring and optionally classifying samples that use a marker expression measurement that is now known or later discovered to be highly correlated with the expression of an exemplary marker expression value in addition to or in lieu of that exemplary marker expression value. For the purposes of the present invention, such highly correlated genes are contemplated either to be within the literal scope of the claimed inventions or alternatively encompassed as equivalents to the exemplary markers. Identification of markers having expression values that are highly correlated to those of the exemplary markers, and their use as a component of a predictive model is well within the level of ordinary skill in the art. The Examples section below provides numerous examples of methods for identifying highly correlated markers and substituting them for algorithm markers in predictive models of CAD and methods for their use to score and optionally classify samples.

Computer Implementation

In one embodiment, a computer comprises at least one processor coupled to a chipset. Also coupled to the chipset are a memory, a storage device, a keyboard, a graphics adapter, a pointing device, and a network adapter. A display is coupled to the graphics adapter. In one embodiment, the functionality of the chipset is provided by a memory controller hub and an I/O controller hub. In another embodiment, the memory is coupled directly to the processor instead of the chipset.

The storage device is any device capable of holding data, like a hard drive, compact disk read-only memory (CD-ROM), DVD, or a solid-state memory device. The memory holds instructions and data used by the processor. The pointing device may be a mouse, track ball, or other type of pointing device, and is used in combination with the keyboard to input data into the computer system. The graphics adapter displays images and other information on the display. The network adapter couples the computer system to a local or wide area network.

As is known in the art, a computer can have different and/or other components than those described previously. In addition, the computer can lack certain components. Moreover, the storage device can be local and/or remote from the computer (such as embodied within a storage area network (SAN)).

As is known in the art, the computer is adapted to execute computer program modules for providing functionality described herein. As used herein, the term "module" refers to computer program logic utilized to provide the specified functionality. Thus, a module can be implemented in hardware, firmware, and/or software. In one embodiment, program modules are stored on the storage device, loaded into the memory, and executed by the processor.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information.

Embodiments of the entities described herein can include other and/or different modules than the ones described here. In addition, the functionality attributed to the modules can be performed by other or different modules in other embodiments. Moreover, this description occasionally omits the term "module" for purposes of clarity and convenience.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990); Carey and Sundberg *Advanced Organic Chemistry* $3^{rd}$ Ed. (Plenum Press) Vols A and B (1992).

Materials and Methods

General Study Design

The overall study design is shown in FIG. 1. This study had four distinct, consecutive phases. The PREDICT clinical trial registration information is available on the clinicaltrials.gov website at NCT00500617 on May 28, 2010.

Phase 1—Cathgen Discovery.

Phase 1 was Initial Gene Discovery from the Duke University CATHGEN registry, a retrospective blood repository.[11] Briefly, 198 subjects (88 cases, 110 controls) from this repository were enrolled between August 2004 and November, 2005. Clinical inclusion and exclusion criteria were described previously and included both diabetic and non-diabetic patients.[7] All CATHGEN patients gave written informed consent and the study protocol was approved by the Duke University IRB. Microarrays were performed to identify CAD sensitive genes, and a subset of genes was selected for RT-PCR replication. Given the phase I findings, only non-diabetic subjects were included subsequently.

Phase II—Predict Discovery.

Phase 2 was a prospective gene discovery phase with subjects from the PREDICT study, where 198 patients (99 case: control pairs, matched for age and sex) underwent microarray analysis to identify differentially expressed genes.

Phase III—Predict Development.

Phase 3 was prospective algorithm development with 640 patients (210 cases, 430 controls) to determine the inter-relationships between clinical factors, blood cell counts, gene expression, and CAD.

Phase IV—Predict Validation.

After Phase III was completed the locked algorithm was prospectively validated in an independent cohort of 526 patients (192 cases, 334 controls).

Subjects from PREDICT were eligible if they had a history of chest pain, suspected anginal-equivalent symptoms, or a high risk of CAD with no known prior MI, revascularization, or CAD. Detailed inclusion/exclusion criteria have been described.[12] Diabetic status was defined by clinical identification, blood glucose (non-fasting $\geq 200$ or fasting $\geq 126$), rorhemoglobin A1c, ($\geq 6.5$), or diabetic medication prescription. Complete blood counts with differentials were obtained for all patients. PREDICT patients gave written informed consent, and the study protocol was approved by the Western Institutional Review Board.

Blood Collection, RNA Purification, and RT-PCR

Whole blood samples were collected in PAXgene® tubes prior to coronary angiography, according to the manufacturer's instructions, and then frozen at −20° C. For the CATHGEN samples RNA was purified as described (PreAnalytix, Franklin Lakes, N.J.), followed by quantitative analysis (Ribogreen, Molecular Probes, Eugene, Oreg.). For the PREDICT samples an automated method using the Agencourt RNAdvance system was employed. Microarray samples were labeled and hybridized to 41K Human Whole Genome Arrays (Agilent, PN #G4112A) using the manufacturer's protocol. For PREDICT microarrays all matched pairs were labeled and hybridized together to minimize microarray batch effects. Microarray data sets have been deposited in GEO (GSE 20686).

Amplicon design, cDNA synthesis, and RT-PCR were performed as previously described.[7,12] All PCR reactions were run in triplicate and median values used for analysis. The primers and probes are shown in the Informal Sequence Listing below. The primers and probe for marker CD3D were obtained commercially from Applied Biosystems, Inc. (Assay ID: Hs00174158_m1; Part No. 4331182).

Fractionation of Whole Blood Cells for Cell-type Specific Gene Expression Measurements Cell fractionation was performed on fresh blood collected in EDTA tubes. 120 ml blood pooled from 4 different donors was 1:1 diluted with 1×PBS. 15% of the blood was used for granulocyte isolation by density centrifugation and 85% of the blood was used for PBMC isolation prior to T cells, B cells, NK cells, and monocytes fractionation.

Peripheral Blood Mononuclear Cell (PBMC) isolation

PBMC was isolated by density centrifugation. 20 ml diluted blood was layered on 20 ml Histopaque 1077 (Sigma Cat No. 10771) in 50 ml conical tubes and was centrifuged at room temperature for 30 min at 400×g. The PBMC layer was carefully aspirated into new tubes and washed with 1× phosphate-buffered saline (PBS) twice and centrifuged at 200×g for 10 min. The washed PBMC was re-suspended in cold bufferl (1×PBS, 0.1% BSA and 2 mMEDTA) and stored on ice. 5% of the cells were lysed in RLT buffer (Qiagen RNeasy Mini kit, Cat No. 74104) for pre-selection RNA isolation.

Granulocyte Isolation

Granulocytes (neutrophils, eosinophils, basophils) were purified by density centrifugation using two different density mediums. In 15 ml conical tube, 3 ml Hisopaque 1077 was layered on 3 ml Histopaque 1119 (Sigma Cat No. 11191) and 6 ml of the diluted blood was then layered on Histopaque 1077. The tube was centrifuged at room temperature (RT) for 30 min at 700×g. The granulocyte layer was then aspirated into a new tube and washed twice. The pellet was re-suspended in RLT buffer for granulocyte RNA isolation.

Positive Cell Isolation with Magnetic Beads

The subsequent cell types (T cells, B cells, natural killer (NK) cells, monocytes) were positively selected from PBMC used the following reagents and the recommended procedures.

CD8+ T cells—Dynal® CD8 positive isolation kit (Invitrogen Cat. No. 113.33D)

CD3+ T cells—Dynabeads® CD3 (Invitrogen Cat. No. 111.51D)

CD19+ B cells—Dynabeads® CD19 pan B (Invitrogen Cat. No. 111.43D)

CD14+ Monocytes—Dynabeads® CD14 (monocytes/macrophages) (Invitrogen Cat. No. 111.49D)

CD56+ NK cells—Dynabeads® Pan Mouse IgG (Invitrogen Cat. No. 110.41) cross-linked with mouse anti-human CD56 antibodies (BD bioscience Cat No. 556325)

Briefly, PBMC were incubated with antibody-coupled magnetic beads at 4° C. for 20 min and washed 3 times with buffer 1 on the magnet. The selected cells were then re-suspended in RLT buffer for RNA isolation.

RNA Isolation

The RNA samples in RLT buffer were purified using the Qiagen RNeasy Mini kit following the manufacturer's instructions.

Coronary Angiographic Analysis and Case: Control Definition

All patients were clinically referred for angiography and angiograms were performed based on local, institutional protocols. For CATHGEN patients, clinical angiographic interpretation defined cases as ≥75% maximum stenosis in one major vessel or ≥50% in two vessels and controls as <25% stenosis in all major vessels.

For PREDICT patients, core laboratory QCA reads (Cardiovascular Research Foundation New York) were used for case: control classification. Cases had >50% stenosis in at least one major coronary vessel and controls <50% stenosis in all major vessels.

Correlation between Gene Expression and Cell Type Distributions

Correlations with complete blood counts and database gene expression analysis (SymAtlas) were used to identify highly cell-type selective genes. In addition, whole blood cell fractionation by density centrifugation or through positive antibody selection followed by RT-PCR was performed on specific cell fractions.

Statistical Methods

All statistical methods were performed using the R software package. The statistical methods used are described and referenced in greater detail below.

Array Normalization

Agilent processed signal values for array normalization were scaled to a trimmed mean of 100 and then log 2 transformed. Standard array QC metrics (percent present, pairwise correlation, and signal intensity) were used for quality assessment, resulting in 3 of 198 CATHGEN and 12 of 210 PREDICT samples being excluded.

Array Analysis

For the CATHGEN array, logistic regression (unadjusted and sex/age adjusted) was used to assess gene expression association with case: control status. For the PREDICT array, given the paired design, conditional logistic regression was used. False discovery rates were used to account for multiple comparisons. GOEAST was used to determine over-representation of Gene Ontology (GO) terms.[13]

Gene Selection

Genes for RT-PCR were selected based on significance, fold-change, pathway analysis, and literature support. Hierarchical clustering based on gene: gene correlations ensured that RT-PCR genes represented multiple clusters. Normalization genes were selected based on low variance, moderate to high expression, and no significant association with case: control status, sex, age, or cell counts.

PCR Statistical Analysis

Clinical/demographic factors were assessed for CAD association using univariate and multivariate logistic regression. Gene expression association with CAD and other clinical/demographic factors was assessed by robust logistic regression (unadjusted and sex/age adjusted).[7]

Algorithm Development and Validation

Hierarchical clustering was used to group genes using a correlation cutoff. Clusters were reduced to meta-genes[14] and normalization genes based on correlation structure, known biology, and cell count correlation. For meta-gene pairs with high correlation and opposite disease regulation, ratio terms (differences on the log scale) were defined. Meta-genes independently associated with outcome were selected by the LASSO method, with sex by meta-gene interactions allowed during variable selection.[15]

The final algorithm was fit using Ridge regression[16], where the outcome variable was case:control status and the predictors the LASSO-selected meta-genes and sex-specific age terms. Sex was a binary predictor, and age a linear predictor with separate slopes for males, females >60, and females <60. Gene expression term penalization was based on cross-validation and prior evidence. Model performance was estimated using leave-one-out cross-validation. Algorithm performance was validated in an independent patient cohort with ROC analysis as primary endpoint.

Algorithm Calculation and Transformation
Data Preprocessing and QC Steps
1) Compute median of triplicate wells for each algorithm gene/sample
   a. If one well has a no call, take the median of the two remaining wells
   b. If two or three wells have a no call, the algorithm gene receives a no call for that sample
2) If AF161365 (TSPAN16) receives a no call, impute the value of 38 as the median value for that gene.
3) If any algorithm gene other than AF161365 receives a no call, the sample fails for Missing Gene Cp. None of the 640 samples in Algorithm Development would fail this metric.
4) Compute the median of the algorithm gene SD's, excluding AF161365. If this value is greater than 0.15, the sample fails for High Replicate SD.
5) For each algorithm gene i, floor the Cp value by replacing values less than $GL_i$ with $GL_i$ This value represents the $1^{st}$ percentile of Cp for that gene in the Algorithm Development set.
6) For each algorithm gene i, ceiling the Cp value by replacing values greater than $GU_i$ with $GU_i$. This value represents the $99^{th}$ percentile of Cp for that gene in the Algorithm Development set.
7) For each algorithm gene i, compute the absolute value of the difference between its Cp value and $GM_i$, where $GM_i$ represents the median Cp for that gene in the Algorithm Development set. Sum this value across the algorithm genes (excluding AF161365). If the sum is greater than 27.17, the sample fails for Expression Profile Out of Range. 27.17 represents the largest value of this metric within the Algorithm Development set.

In certain cases, an algorithm score will not be calculated for a subject. Reasons for this include low PAXgene® tube blood volume, lab QC failure, etc. The frequency of occurrence of these failures will be tabulated, though these subjects will not be included in the analysis set. Subjects with missing Diamond Forrester scores will not be included in the analysis set.

Algorithm Calculation
1) Define $Norm_1$=RPL28
2) Define $Norm_2$=(0.5*HNRPF+0.5*TFCP2)
3) Define $NK_{up}$=(0.5*SLAMF7+0.5*KLRC4)
4) Define $T_{cell}$=(0.5*CD3D+0.5*TMC8)
5) Define $B_{cell}$=(⅔*CD79B+⅓*SPB3)
6) Define Neut=(0.5*AQP9+0.5*NCF4)
7) Define $N_{up}$=(⅓*CASP5+⅓*IL18RAP+⅓*TNFAIP6)
8) Define $N_{down}$=(0.25*IL8RB+0.25*TNERSF10C+0.25*TLR4+0.25*KCNE3)
9) Define SCA=(⅓*S100A12+⅓*CLEC4E+⅓*S100A8)
10) Define $AF_2$=AF289562
11) Define TSPAN=1 if (AF161365−$Norm_2$>6.27 or AF161365=NoCall), 0 otherwise
12) Define SEX=1 for Males, 0 for Females
13) Define Intercept
   a. For Males, INTERCEPT=2.672+0.0449*Age
   b. For Females, INTERCEPT=1.821+0.123*(Age−60), if negative set to 0
14) Define Score=INTERCEPT−0.755*($N_{up}$−$N_{down}$)−0.406*($NK_{up}$−$T_{cell}$)−0.308*SEX*($SCA_1$−$Norm_1$)−0.137*($B_{cell}$−$T_{cell}$)−0.548*(1−SEX)*($SCA_1$−Neut)−0.482*SEX*(TSPAN)−0.246*($AF_2$−$Norm_2$)

Score Transformation
The endpoint analyses defined were performed using raw algorithm scores. For clinical reporting purposes, as well as ease of presentation, raw scores may be transformed into a transformed score with a scale designed for ease of clinical use as follows:
   Input is Raw Score
   If Raw Score<−2.95, set RawScore=−2.95
   If Raw Score>1.57, set RawScore=1.57
   Raw Score=2.95+RawScore
   Final Score=RawScore*40/4.52
   Round Final Score up to nearest integer
   If Final Score is greater than 40, set to 40
   If Final Score is less than 1, set to 1
   Value obtained is the Final Transformed Score Estimation of Score Variability
A total of 41 replicate samples were tested from a large PAXgene® blood pool. The standard deviation of the raw score for these replicates was 0.13. The confidence interval around a given raw score was then the raw score plus or minus 1.96*0.13. The upper and lower bounds of this confidence interval were linearly transformed to the 0 to 40 scale, and then transformed to a confidence interval around the likelihood using the score to likelihood function described above.

Example 1

Demographic Data

Baseline demographic characteristics of the CATHGEN registry and PREDICT study patient cohorts are shown in Table 1. In general, CAD cases were more frequently men, older, had higher SBP, and more dyslipidemia.

Example 2

Phase I: Initial Gene Discovery (CATHGEN)

Figure 2:
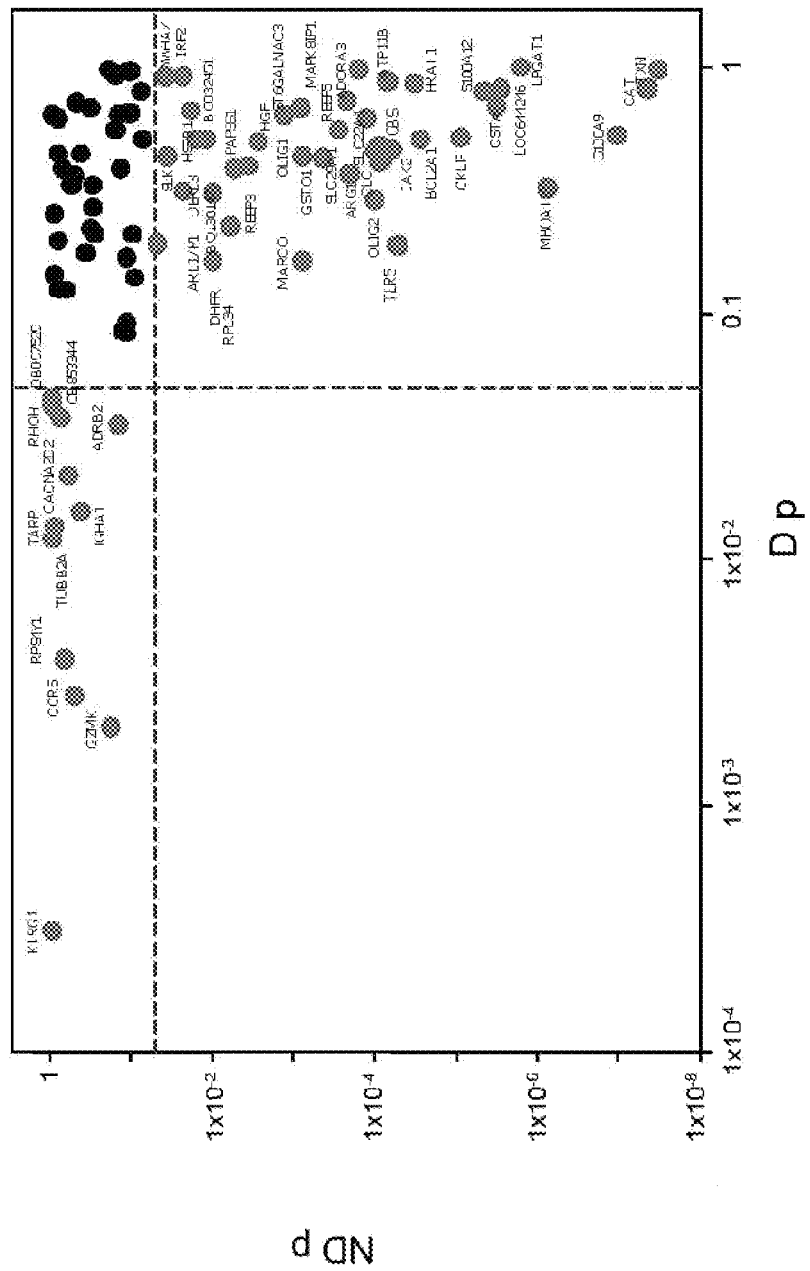
FIG. 2—RT-PCR Analysis of Diabetics vs Non-diabetic Significant Genes from CATHGEN Microarray analysis. Significance of individual genes selected from the CATHGEN microarray cohort in non-diabetic (ND) and diabetic (D) patients is shown. The sex/age adjusted p values from a CAD logistic regression analysis in each subset are plotted (log scale). Significant p values (<0.05) are indicated in red with gene symbols (upper left quadrant and lower right quadrant), non-significant ones in black (upper right quadrant).

A total of 2438 genes showed significant CAD association (p<0.05) in a 195 subject case:control analysis (FIG. 1). Clinical and demographic factor analysis of gene expression showed diabetes as the most significant (p=0.0006, Table 3). Based on statistical significance and biological relevance, 88 genes (Table 4) were selected for RT-PCR analysis on these same samples. CAD-gene expression analysis in non-diabetic and diabetic subsets (N=124 and 71, respectively), showed 42 and 12 significant genes, respectively (p<0.05), with no intersection (FIG. 2). Further work was thus limited to non-diabetics.

We observed a strong diabetes-gene expression interaction effect on CAD risk in the CATHGEN cohort, and thus restricted algorithm development to PREDICT non-diabetics. The CATHGEN diabetic subjects encompassed a range of disease severity and a variety of medications, some of which modulate gene expression and affect cardiovascular disease.[17]

Example 3

Phase II: Non-Diabetic Gene Discovery (PREDICT)

Figure 3:
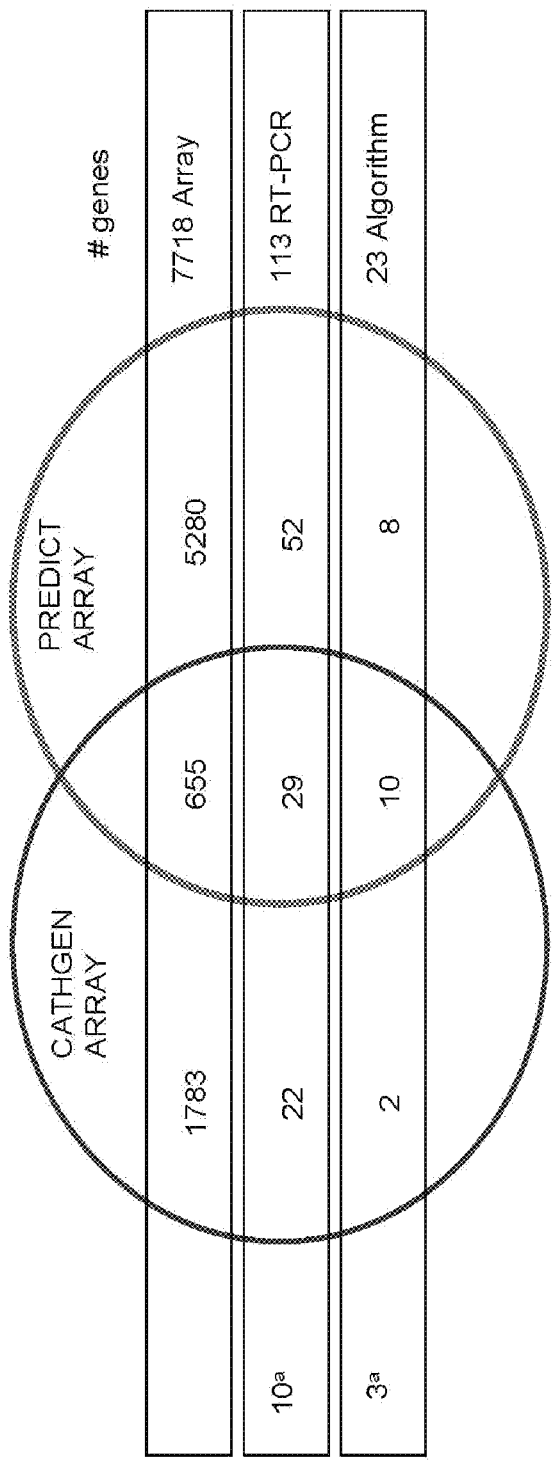
FIG. 3—Venn Diagram of microarray, RT-PCR, and algorithm gene sources. A total of 7718 genes were identified, 2438 and 5935, respectively, from the CATHGEN and PREDICT microarray analyses, with an intersection of 655 genes. For the 113 RT-PCR genes, 52 were from PREDICT, 22 from CATHGEN, and 29 from both; 10 were either normalization genes or from previous studies.[7] The final algorithm contained 20 informative genes: 10 from both microarray studies, 8 PREDICT alone, and 2 CATHGEN alone.

Microarray CAD gene discovery on 210 PREDICT patient samples used a paired case:control experimental design, to reduce confounding effects of age, sex, and microarray batch processing. CAD analysis on the 99 case:control pairs after QC exclusions yielded 5935 significant genes (p<0.05) with 655 genes in common with the CATHGEN results (FIG. 3, Table 5).

Pathway Analysis of Discovery Genes

Gene Ontology (GO) analysis of these 655 genes identified 189 significant biological process terms (p<0.05, Table 6), largely reflecting inflammation, cellular and stress response, cell death, and apoptosis. The cellular and molecular ontologies showed enrichment of 32 and 49 terms respectively, including mitochondrial function, apoptotic protease activator activity, and antigen binding.

Gene Selection

A total of 113 genes (Table 2) were selected by statistical significance, biological relevance, and prior association with CAD and gene expression measured by RT-PCR in the PREDICT development cohort. Known cell-type specific markers, those correlated with cell counts in PREDICT, and candidate normalization genes, were also represented.

Example 4

Phase III: Prospective Algorithm Development (PREDICT)

Figure 4:
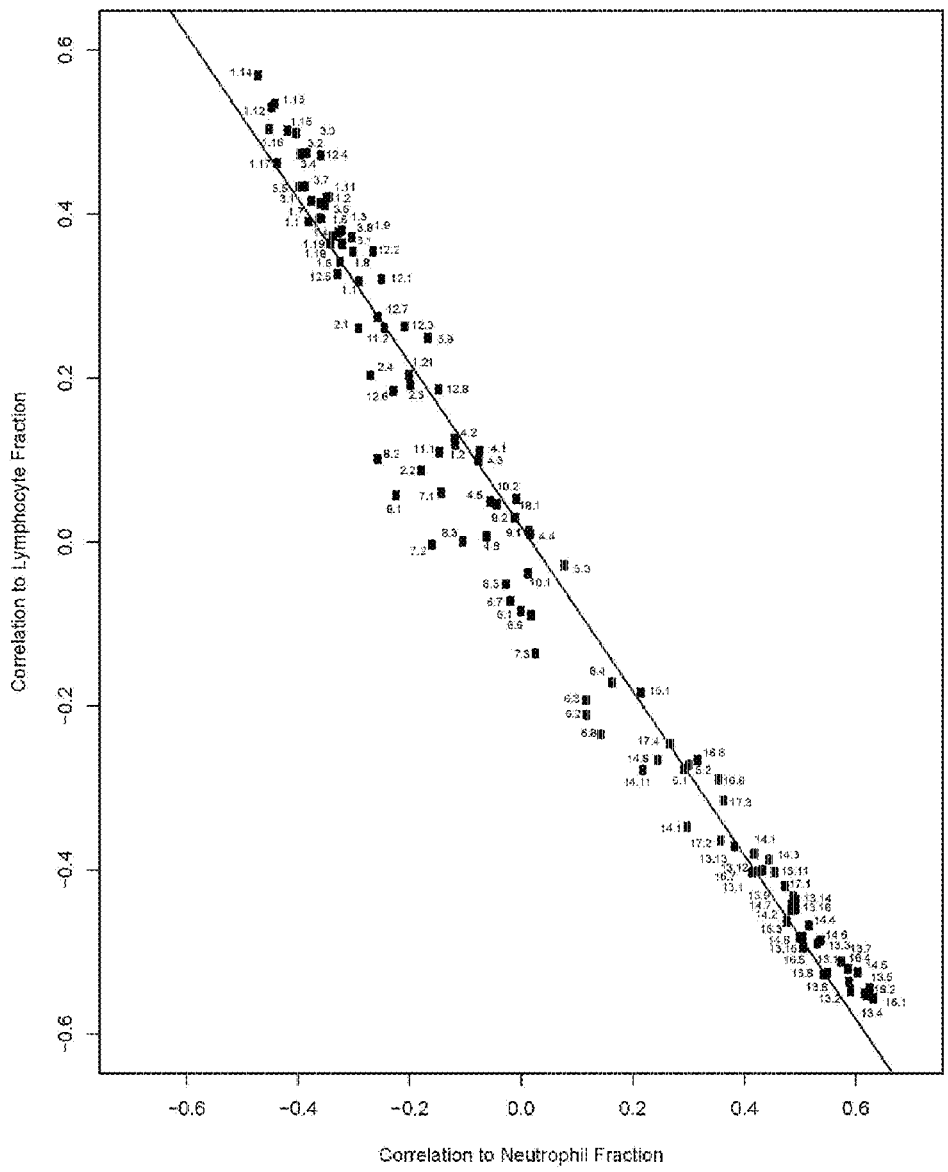
FIG. 4—Correlation of PCR gene expression to lymphocyte fraction (y-axis) and neutrophil fraction (x-axis) for the 113 PCR genes measured in the PREDICT algorithm development cohort. The range of correlation is up to 0.6 and a total of 42 genes were correlated with neutrophil fraction at >0.2 whereas 39 genes were correlated with lymphocyte count at the same threshold. Genes are identified using the numbering scheme in Table 2.

The algorithm was derived using the RT-PCR and clinical data from the PREDICT development cohort. The most significant clinical factors for CAD:gene expression association were age, sex, chest pain type, and neutrophil count. Age and sex were independent risk factors for CAD (Table 1) and showed significant gene expression correlation. Chest pain type was also a significant independent risk factor (p=0.005), but was gene expression independent. Neutrophil count was significantly correlated (positively or negatively) to expression of 93 of 113 RT-PCR genes, and was significantly associated with CAD in males (p=0.049), but not females (p=0.77). Gene expression correlations for all genes to neutrophil and lymphocyte fraction were computed (FIG. 4). A correlation cut-off of >0.2 yielded 39 genes as lymphocyte-associated and 42 genes as neutrophil-associated. Neutrophil-associated genes showed both up and down regulation with CAD status, whereas lymphocyte-associated genes were generally down-regulated. There was significant gender-specific regulation of neutrophil correlated genes (males 40/42 genes up-regulated, females, 41/42 down-regulated) whereas lymphocyte gene down-regulation was gender independent.

Hierarchical clustering of the 113 PCR genes resulted in 18 correlated clusters (Table 2), with finer correlation substructure within the lymphocyte and neutrophil associated genes. There were 3 lymphocyte subgroups representing T-cells (clusters 1,2,3), B-cells (cluster 3), and NK cells (cluster 12). Three neutrophil subgroups were also identified: previously described neutrophil genes (IL8RB, S100A8, S100A12, TXN, BCL2A1; cluster 13, 16); newly identified up-regulated neutrophil genes (CLEC4E, CASP5, TNFAIP6; cluster 16) and down-regulated neutrophil genes (KCNE3, TLR4, TNFRSF10C; clusters 13, 14).[7] The 29 genes in clusters 4-11 did not have clear cell-type association.

Algorithm Derivation

Based on the correlation and cell-type analyses, 15 meta-genes and 3 normalization genes were defined as inputs for model variable selection. Selection by the LASSO method, and weight penalization by Ridge regression resulted in the final, locked algorithm, comprising 20 CAD-associated genes and 3 normalization genes in 6 meta-genes (FIG. 5). The algorithm score was defined as the predicted regression model value.

Summary

The PCR algorithm development set was sufficiently powered to investigate the relationship between CAD, clinical factors, and gene expression. The most significant independent clinical risk factors for CAD were age, gender, and chest pain type, the components of the Diamond-Forrester risk model for CAD likelihood,[1] supporting its use as a reference to assess algorithm performance.[12]

The relationships between age, gender, CAD, and gene expression are complex. Increasing age and male gender are well-known risk-factors for CAD which affects gene expression in circulating cells.[18,19] The majority of genes measured by RT-PCR in this study correlated with lymphocyte or neutrophil fraction (FIG. 4; r>0.2 for 39 and 42 genes respectively). Genes in the neutrophil-associated group include many we previously identified (clusters 6,13,14; Table 2).[7] Lymphocyte group genes include those known to be expressed in T-cells (CD3, TMC8), B-cells (SPIB, CD79B), and NK-cells (SLAMF7, KLRC4) (Clusters 1,3, and 12, respectively). Lymphocyte-associated gene expression decreases with CAD in a gender-independent fashion, consistent with decreased lymphocyte counts being correlated with increased cardiovascular risk.[8] In contrast, neutrophil-associated genes display significant sex-specific expression differences with CAD: in males 95% of the neutrophil genes were up-regulated whereas 98% were down-regulated in females, consistent with increased granulocyte counts in males being associated with higher CAD risk, with smaller effects in females.[20]

Biological Significance of Algorithm Terms

The use of correlated meta-genes as building blocks for the algorithm is significantly reflective of gene expression cell-type specificity. The algorithm genes are expressed selectively in multiple types of circulating cells including neutrophils, NK cells, B and T-lymphocytes[21], supporting roles for both adaptive and innate immune responses in atherosclerosis.[4]

Algorithm term 1 genes (FIG. 5) preferentially expressed in neutrophils, may reflect neutrophil apoptosis, as caspase-5 is increased with CAD, whereas TNFRSF10C, an anti-apoptotic decoy receptor of TRAIL, is decreased.[22] Term 2 genes up-regulated with CAD likely reflect both innate immune activation (S100A8 and S100A12),[23] and a cellular necrosis response (CLEC4E).[24] S100A8 and S100A12 are up-regulated in chronic inflammatory conditions, perhaps reflecting a more general pathophysiological signal, consistent with increased CAD in disorders such as rheumatoid arthritis.[25,26]

Term 2 is normalized in a gender specific manner. In males normalization to RPL28, which is strongly expressed in lymphocytes, reflects the neutrophil to lymphocyte ratio, which is prognostic for death or MI in a CAD population.[8] In females normalization to AQP9 and NCF4, two CAD insensitive neutrophil genes, permits assessment of neutrophil up-regulation of the S100s and CLEC4E.

Term 3 consists of 2 NK cell receptors, SLAMF7 and KLRC4, normalized to T-cell specific genes (TMC8 and CD3D). SLAMF7 may specifically activate NK cell function, while inhibiting B and T cells.[27] KLRC4 is also likely involved in NK cell activation.[28] NK cells have been associated with atherosclerosis in both mouse models and humans, and reduced lymphocyte counts associated with cardiac events.[8,29]

Term 4 is a gene expression based measure of the B/T-cell ratio. The role of T cells is complex, whereas B cells have been shown in mouse models to be athero-protective.[30,31] In this study apparent up-regulation of B-cell specific genes is correlated with CAD, perhaps indicating an immunological response to disease. The last two terms, based on AF289562 (AF2) and TSPAN16 are genes of unknown function.

Example 5

Phase IV: Prospective Algorithm Validation (PREDICT)

Figure 6:
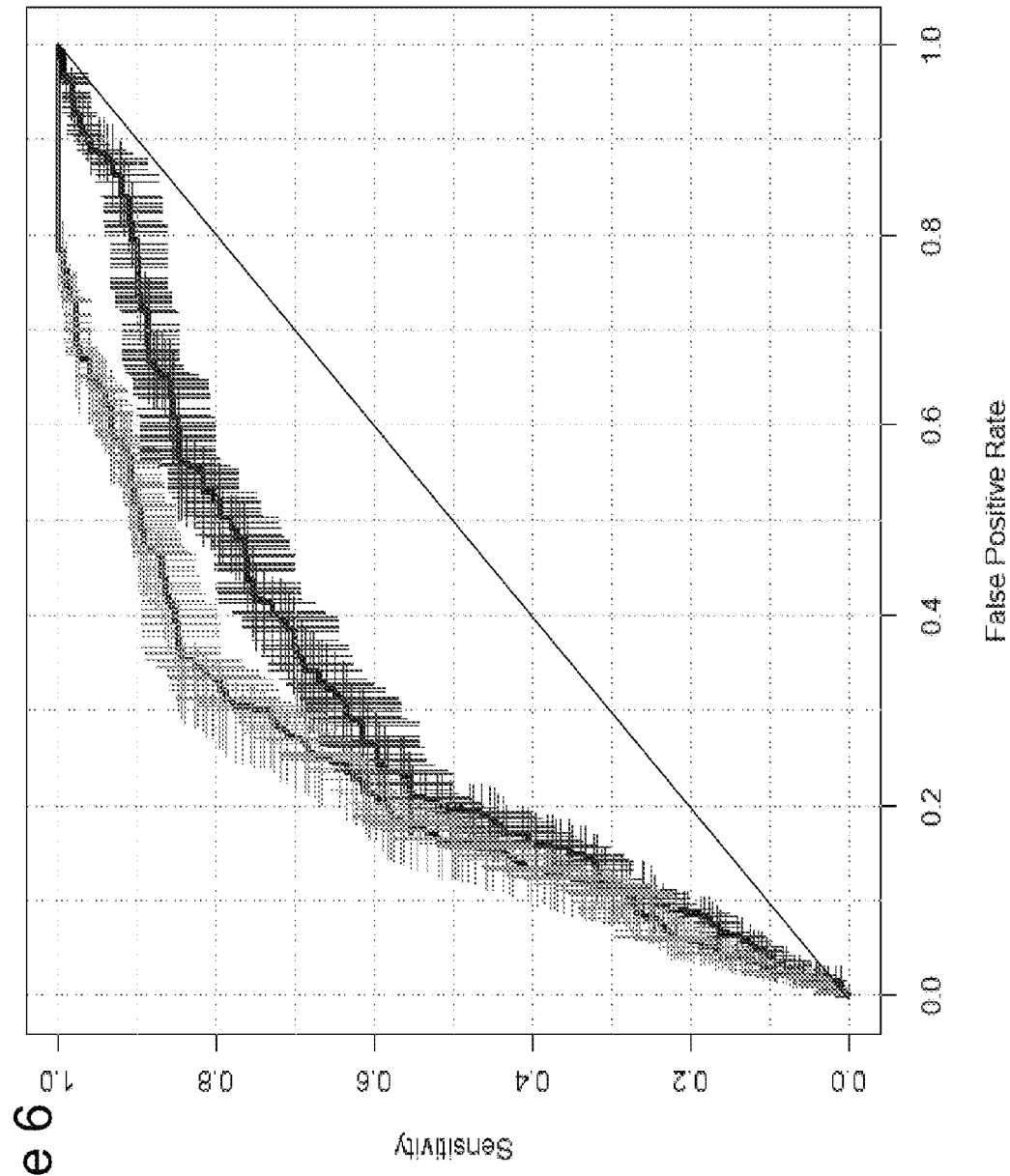
FIG. 6—Comparison of Algorithm Performance between Cross-Validation Estimate and Independent Validation. ROC curves of the cross-validation (dashed line) and independent validation (solid line) of the algorithm is shown relative to an AUC of 0.50 (dotted line). The 95% confidence intervals are indicated by the solid areas. The AUC values are: for cross-validation 0.77 (95% CI, 0.73-0.81) and for the independent validation cohort 0.70 (95% CI, 0.65-0.75, $p=10^{-16}$).

The estimated cross-validated algorithm AUC in ROC analysis in the PREDICT development set was 0.77 (95% CI 0.73 to 0.81); prospective validation in the independent PREDICT validation set of 526 patients (192 cases, 334 controls) yielded an AUC of 0.70 (95% CI=0.65 to 0.75) (FIG. 6).

For algorithm development in Phases III and IV, we used a robust approach, which minimized the effect of any single gene, by using meta-genes as building blocks.[14,32] Penalized stepwise logistic regression (LASSO) selected significant meta-genes from a 640 patient data set which greatly exceeded the number of candidate variables (15 meta-genes), reducing the likelihood of over-fitting. Further, in order to minimize over-weighting of individual terms, meta-gene coefficients were penalized using Ridge regression.

The cross-validated model AUC was 0.77 (95% CI 0.73 to 0.81), suggesting the algorithm score was a significant CAD predictor, and the validation cohort AUC was 0.70, with overlapping confidence intervals (95% CI=0.65 to 0.75). This modest decrease may reflect an over-optimistic cross-validation estimate, as we did not re-select terms during each iteration.

Thus, using a series of microarray and RT-PCR data sets, comprising more than 1,500 patients, we have derived and validated an algorithm, consisting of the expression levels of 23 genes, sex, and age, which assesses the likelihood of obstructive CAD in non-diabetic patients.

Example 6

Summary of Above Examples

This study presents the development and validation of a whole blood derived RT-PCR based gene-expression algorithm for assessment of obstructive CAD likelihood in non-diabetic patients, and includes several key findings. First, gene expression patterns that differentiate diabetic patients with and without CAD were very different from those for study patients without diabetes. In the initial Gene Discovery Cohort, 2438 genes were differentially expressed in cases versus controls. In the second, PREDICT gene discovery cohort in non-diabetic patients, 5935 genes were differentially expressed and 655 overlapped with the initial gene discovery genes. Based on overall correlations and biological significance, 113 of these 655 genes, were selected for RT-PCR analysis in the independent algorithm development cohort (Phase III), which also identified relationships between clinical factors, cell counts, and gene expression. The algorithm, including 23 gene expression levels, age, and sex, was derived from these data and locked. It was then prospectively shown to have significant diagnostic accuracy in Phase IV, the prospective PREDICT validation cohort, with an AUC of 0.70 (95% CI=0.65 to 0.75; p=$10^{-16}$).

We consider our results robust, due to at least two factors. First, we used a carefully designed, serial, four-phase study comprising >1,500 patients, with initial microarray-based gene discovery confirmed by quantitative RT-PCR measurements in independent patients. Second, we used QCA to define CAD cases and controls, yielding a more accurate gold standard.

Example 7

Removal of One Term from the Algorithm

In the following series of examples (7-47), we examined the sensitivity of the algorithm and the algorithm development process to differences in terms, markers, and statistical methods. Each example follows the same general procedure: 1) identify a plausible alternative model approach (e.g., fewer terms, alternate markers, etc.); 2) rebuild the algorithm based on that alternative approach, including re-weighting the terms and/or markers as appropriate; and 3) assess whether the new model retains significant predictive accuracy.

The ability of the algorithm to determine the likelihood of CAD in the absence of one out of the seven terms was assessed. A single term was removed sequentially from the algorithm while maintaining the other terms and the clinical factors of age and gender. For example, term 1 was removed from the algorithm while terms 2-7 and the clinical factors (age and gender) remained in the algorithm. The markers in terms 1-7 are shown in the table below. Two statistical methods were used for the assessment: logistic regression and ridge regression. For all analyses, the area under the ROC curve (AUC) was the primary accuracy metric used. AUC was computed using cross validation. For example, when term 1 was removed from the algorithm the altered algorithm was as follows:

Algorithm Calculation (Ridke Regression; removal of Term 1)
1) Define $Norm_1$=RPL28
2) Define $Norm_2$=(0.5*HNRPF+0.5*TFCP2)
3) Define $NK_{up}$=(0.5*SLAMF7+0.5*KLRC4)
4) Define $T_{cell}$=(0.5*CD3D+0.5*TMC8)
5) Define $B_{cell}$=(⅔*CD79B+⅓*SPIB)
6) Define Neut=(0.5*AQP9+0.5*NCF4)
7) Define $N_{up}$=(⅓*CASP5+⅓*IL18RAP+⅓*TNFAIP6)
8) Define $N_{down}$=(0.25*IL8RB+0.25*TNFRSF10C+0.25*TLR4+0.25*KCNE3)
9) Define $SCA_1$=(⅓*MMP9+⅓*CLEC4E+⅓*S100A8)
10) Define $AF_2$=AF289562
11) Define SEX=1 for Males, 0 for Females
12) Define Intercept
   a. For Males, INTERCEPT=0.70+0.044*Age
   b. For Females, INTERCEPT=0.38+0.126*(Age-60), if negative set to 0
13) Define Score=INTERCEPT−0.39*($N_{up}$−$N_{down}$)−0.26*(NK−$T_{cell}$)−0.33*SEX*($SCA_1$−$Norm_1$)−0.06*($B_{cell}$−$T_{cell}$)−0.07*(1−SEX)*($SCA_1$−Neut)−0.26*($AF_2$−$Norm_2$)

A similar algorithm development procedure was used for the sequential removal of the other terms in this example as well as examples below. Summary statistics for each of the calculations as well as the mean and standard deviation of the results are shown in Table 7. AUC's greater than the upper bound of the confidence interval for the AUC of Diamond Forrester (DF) were considered significantly better than the DF model. See Table 8. All six-term sets tested were significantly better than the DF model indicating that the algorithm remains predictive of the likelihood of CAD even after removal of one term.

| Term | Markers |
| --- | --- |
| Term 1 | AF161365, HNRPF, TFCP2 |
| Term 2 | AF289562, HNRPF, TFCP2 |
| Term 3 | CD79B, SPIB, CD3D, TMC8 |

| Term | Markers |
|---|---|
| Term 4 | S100A12, CLEC4E, S100A8, RPL28 |
| Term 5 | S100A12, CLEC4E, S100A8, AQP9, NCF4 |
| Term 6 | CASP5, IL18RAP, TNFAIP6, IL8RB, TNFRSF10C, KCNE3, TLR4 |
| Term 7 | SLAMF7, KLRC4, CD3D, TMC8 |

Example 8

Removal of Two Terms from the Algorithm

The ability of the algorithm to determine the likelihood of CAD in the absence of two out of the seven terms was assessed. Two distinct terms were removed from the algorithm while maintaining the other terms and the clinical factors of age and gender. For example, terms 6-7 were removed from the algorithm while terms 1-5 and the clinical factors remained in the algorithm. All possible five term combinations were assessed. Two statistical methods were used for the assessment: logistic regression and ridge regression. For all analyses, the area under the ROC curve (AUC) was the primary accuracy metric used. AUC was computed using cross validation. Summary statistics for each of the calculations as well as the mean and standard deviation of the results are shown in Table 9. AUC's greater than the upper bound of the confidence interval for the AUC of Diamond Forrester (DF) were considered significantly better than the DF model. See Table 8. All five-term sets tested were significantly better than the DF model indicating that the algorithm remains predictive of the likelihood of CAD even after removal of two terms.

Example 9

Removal of Three Terms from the Algorithm

The ability of the algorithm to determine the likelihood of CAD in the absence of three out of the seven terms was assessed. Three distinct terms were removed from the algorithm while maintaining the other terms and the clinical factors of age and gender. For example, terms 5-7 were removed from the algorithm while terms 1-4 and the clinical factors remained in the algorithm. All possible four term combinations were assessed. Two statistical methods were used for the assessment: logistic regression and ridge regression. For all analyses, the area under the ROC curve (AUC) was the primary accuracy metric used. AUC was computed using cross validation. Summary statistics for each of the calculations as well as the mean and standard deviation of the results are shown in Table 10. AUC's greater than the upper bound of the confidence interval for the AUC of Diamond Forrester (DF) were considered significantly better than the DF model. See Table 8. All four-term sets tested were significantly better than the DF model indicating that the algorithm remains predictive of the likelihood of CAD even after removal of three terms.

Example 10

Removal of Four Terms from the Algorithm

The ability of the algorithm to determine the likelihood of CAD in the absence of four out of the seven terms was assessed. Four distinct terms were removed from the algorithm while maintaining the other terms and the clinical factors of age and gender. For example, terms 4-7 were removed from the algorithm while terms 1-3 and the clinical factors remained in the algorithm. All possible three term combinations were assessed. Two statistical methods were used for the assessment: logistic regression and ridge regression. For all analyses, the area under the ROC curve (AUC) was the primary accuracy metric used. AUC was computed using cross validation. Summary statistics for each of the calculations as well as the mean and standard deviation of the results are shown in Table 11. AUC's greater than the upper bound of the confidence interval for the AUC of Diamond Forrester (DF) were considered significantly better than the DF model. See Table 8. All three-term sets tested were significantly better than the DF model indicating that the algorithm remains predictive of the likelihood of CAD even after removal of four terms.

Example 11

Removal of Five Terms from the Algorithm

The ability of the algorithm to determine the likelihood of CAD in the absence of five out of the seven terms was assessed. Five distinct terms were removed from the algorithm while maintaining the other terms and the clinical factors of age and gender. For example, terms 3-7 were removed from the algorithm while terms 1-2 and the clinical factors remained in the algorithm. All possible two term combinations were assessed. Two statistical methods were used for the assessment: logistic regression and ridge regression. For all analyses, the area under the ROC curve (AUC) was the primary accuracy metric used. AUC was computed using cross validation. Summary statistics for each of the calculations as well as the mean and standard deviation of the results are shown in Table 12. AUC's greater than the upper bound of the confidence interval for the AUC of Diamond Forrester (DF) were considered significantly better than the DF model. See Table 8. All two-term sets tested were significantly better than the DF model indicating that the algorithm remains predictive of the likelihood of CAD even after removal of five terms.

Example 12

Removal of Six Terms from the Algorithm

The ability of the algorithm to determine the likelihood of CAD in the absence of six out of the seven terms was assessed. Six distinct terms were removed from the algorithm while maintaining the other terms and the clinical factors of age and gender. For example, terms 2-7 were removed from the algorithm while term 1 and the clinical factors remained in the algorithm. Two statistical methods were used for the assessment: logistic regression and ridge regression. For all analyses, the area under the ROC curve (AUC) was the primary accuracy metric used. AUC was computed using cross validation. Summary statistics for each of the calculations as well as the mean and standard deviation of the results are shown in Table 13. AUC's greater than the upper bound of the confidence interval for the AUC of Diamond Forrester (DF) were considered significantly better than the DF model. See Table 8. All one-term sets tested were significantly better than the DF model indicating that the algorithm remains predictive of the likelihood of CAD even after removal of six terms.

Example 13

Removal of all Seven Terms from the Algorithm

The ability of the algorithm to determine the likelihood of CAD in the absence of seven out of the seven marker expression terms was assessed. Seven distinct terms were removed from the algorithm while maintaining the clinical factors of age and gender. Two statistical methods were used for the assessment: logistic regression and ridge regression. For the analysis, the area under the ROC curve (AUC) was the primary accuracy metric used. AUC was computed using cross validation. Summary statistics for the calculations are shown in Table 14. AUC's greater than the upper bound of the confidence interval for the AUC of Diamond Forrester (DF) were considered significantly better than the DF model. See Table 8. The age plus gender plus zero-marker expression term set tested was significantly better than the DF model indicating that the algorithm remains predictive of the likelihood of CAD even after removal of all seven marker expression terms. This indicates that the algorithm weighting of gender and age is superior to the weighting of clinical factors in the DF model.

Example 14

Replacement of S100A12 with a Highly Correlated Substitute Marker

For each algorithm marker, a highly correlated, non-algorithm substitute marker was identified from the Phase III PCR data set described above (See Table 1b and Table 2). For each marker, a Pearson correlation value between that marker and all other markers was computed and then we picked the substitute marker with maximal correlation to the algorithm marker of interest. This substitute was the marker with the highest correlation to the algorithm marker, subject to the restriction that a substitute marker was not used more than once in the terms of the algorithm. The correlation value for this particular replacement is shown in Table 15. Two statistical methods were used for the analysis: logistic regression and ridge regression. For the analysis, the area under the ROC curve (AUC) was the primary accuracy metric. AUC was computed using cross validation. Accuracy was computed for models that substituted one gene at a time. In this example, MMP9 was substituted for S100A12 in all relevant terms of the algorithm, here MMP9 was substituted for S100A12 in terms 4 and 5. For example, when S100A12 was replaced in the algorithm with MMP9, the altered algorithm was as follows:

Algorithm Calculation (Logistic Regression, Substitution of MMP9 for S100A12

1) Define $Norm_1$=RPL28
2) Define $Norm_2$=(0.5*HNRPF+0.5*TFCP2)
3) Define $NK_{up}$=(0.5*SLAMF7+0.5*KLRC4)
4) Define $T_{cell}$=(0.5*CD3D+0.5*TMC8)
5) Define $B_{cell}$=(⅔*CD79B+⅓*SPB3)
6) Define Neut=(0.5*AQP9+0.5*NCF4)
7) Define $N_{up}$=(⅓*CASP5+⅓*IL18RAP+⅓*TNFAIP6)
8) Define $N_{down}$=(0.25*IL8RB+0.25*TNFRSF10C+0.25*TLR4+0.25*KCNE3)
9) Define $SCA_1$=(⅓*MMP9+⅓*CLEC4E+⅓*S100A8)
10) Define $AF_2$=AF289562
11) Define TSPAN=1 if (AF161365-Norm2>6.27 or AF161365=NoCall), 0 otherwise
12) Define SEX=1 for Males, 0 for Females
13) Define Intercept
   a. For Males, INTERCEPT=5.28+0.047*Age
   b. For Females, INTERCEPT=4.44+0.120*(Age-60), if negative set to 0
14) Define Score=INTERCEPT−1.05*($N_{up}$−$N_{down}$)−0.56*($N_{up}$−$T_{cell}$)−0.35*SEX*($SCA_1$−$Norm_1$)−0.30*($B_{cell}$−$T_{cell}$)−0.89*(1−SEX)*($SCA_1$−Neut)−0.87*SEX*(TSPAN)−0.38*($AF_2$−$Norm_2$)

A similar algorithm development procedure was used in examples below. Summary statistics for the calculations are shown in Table 15. AUC's greater than the upper bound of the confidence interval for the AUC of Diamond Forrester (DF) were considered significantly better than the DF model. See Table 16 for DF AUC. The algorithm with the substitute marker remained significantly better than the DF model indicating that the algorithm remains predictive of the likelihood of CAD even after replacement of the algorithm marker with the highly correlated substitute marker.

Example 15

Replacement of CLEC4E with a Highly Correlated Substitute Marker

For each algorithm marker, a highly correlated, non-algorithm substitute marker was identified from the Phase III PCR data set described above. For each marker, a Pearson correlation value between that marker and all other markers was computed and then we picked the substitute marker with maximal correlation to the algorithm marker of interest. This substitute was the marker with the highest correlation to the algorithm marker, subject to the restriction that a substitute marker was not used more than once in the terms of the algorithm. The correlation value for this particular replacement is shown in Table 15. Two statistical methods were used for the analysis: logistic regression and ridge regression. For the analysis, the area under the ROC curve (AUC) was the primary accuracy metric. AUC was computed using cross validation. Accuracy was computed for models that substituted one gene at a time. In this example, ALOX5AP was substituted for CLEC4E in all relevant terms of the algorithm. Summary statistics for the calculations are shown in Table 15. AUC's greater than the upper bound of the confidence interval for the AUC of Diamond Forrester (DF) were considered significantly better than the DF model. See Table 16 for DF AUC. The algorithm with the substitute marker remained significantly better than the DF model indicating that the algorithm remains predictive of the likelihood of CAD even after replacement of the algorithm marker with the highly correlated substitute marker.

Example 16

Replacement of S100A8 with a Highly Correlated Substitute Marker

For each algorithm marker, a highly correlated, non-algorithm substitute marker was identified from the Phase III PCR data set described above. For each marker, a Pearson correlation value between that marker and all other markers was computed and then we picked the substitute marker with maximal correlation to the algorithm marker of interest. This substitute was the marker with the highest correlation to the algorithm marker, subject to the restriction that a substitute marker was not used more than once in the terms of the algorithm. The correlation value for this particular replacement is shown in Table 15. Two statistical methods were used for the analysis: logistic regression and ridge regression. For the analysis, the area under the ROC curve (AUC) was the primary accuracy metric. AUC was computed using cross validation. Accuracy was computed for models that substituted one gene at a time. In this example, NAMPT was substituted for S100A8 in all relevant terms of the algorithm.

Summary statistics for the calculations are shown in Table 15. AUC's greater than the upper bound of the confidence interval for the AUC of Diamond Forrester (DF) were considered significantly better than the DF model. See Table 16 for DF AUC. The algorithm with the substitute marker remained significantly better than the DF model indicating that the algorithm remains predictive of the likelihood of CAD even after replacement of the algorithm marker with the highly correlated substitute marker.

Example 17

Replacement of CASP5 with a Highly Correlated Substitute Marker

For each algorithm marker, a highly correlated, non-algorithm substitute marker was identified from the Phase III PCR data set described above. For each marker, a Pearson correlation value between that marker and all other markers was computed and then we picked the substitute marker with maximal correlation to the algorithm marker of interest. This substitute was the marker with the highest correlation to the algorithm marker, subject to the restriction that a substitute marker was not used more than once in the terms of the algorithm. The correlation value for this particular replacement is shown in Table 15. Two statistical methods were used for the analysis: logistic regression and ridge regression. For the analysis, the area under the ROC curve (AUC) was the primary accuracy metric. AUC was computed using cross validation. Accuracy was computed for models that substituted one gene at a time. In this example, H3F3B was substituted for CASP5 in all relevant terms of the algorithm. Summary statistics for the calculations are shown in Table 15. AUC's greater than the upper bound of the confidence interval for the AUC of Diamond Forrester (DF) were considered significantly better than the DF model. See Table 16 for DF AUC. The algorithm with the substitute marker remained significantly better than the DF model indicating that the algorithm remains predictive of the likelihood of CAD even after replacement of the algorithm marker with the highly correlated substitute marker.

Example 18

Replacement of IL18RAP with a Highly Correlated Substitute Marker

For each algorithm marker, a highly correlated, non-algorithm substitute marker was identified from the Phase III PCR data set described above. For each marker, a Pearson correlation value between that marker and all other markers was computed and then we picked the substitute marker with maximal correlation to the algorithm marker of interest. This substitute was the marker with the highest correlation to the algorithm marker, subject to the restriction that a substitute marker was not used more than once in the terms of the algorithm. The correlation value for this particular replacement is shown in Table 15. Two statistical methods were used for the analysis: logistic regression and ridge regression. For the analysis, the area under the ROC curve (AUC) was the primary accuracy metric. AUC was computed using cross validation. Accuracy was computed for models that substituted one gene at a time. In this example, TXN was substituted for IL18RAP in all relevant terms of the algorithm. Summary statistics for the calculations are shown in Table 15. AUC's greater than the upper bound of the confidence interval for the AUC of Diamond Forrester (DF) were considered significantly better than the DF model. See Table 16 for DF AUC. The algorithm with the substitute marker remained significantly better than the DF model indicating that the algorithm remains predictive of the likelihood of CAD even after replacement of the algorithm marker with the highly correlated substitute marker.

Example 19

Replacement of TNFAIP6 with a Highly Correlated Substitute Marker

For each algorithm marker, a highly correlated, non-algorithm substitute marker was identified from the Phase III PCR data set described above. For each marker, a Pearson correlation value between that marker and all other markers was computed and then we picked the substitute marker with maximal correlation to the algorithm marker of interest. This substitute was the marker with the highest correlation to the algorithm marker, subject to the restriction that a substitute marker was not used more than once in the terms of the algorithm. The correlation value for this particular replacement is shown in Table 15. Two statistical methods were used for the analysis: logistic regression and ridge regression. For the analysis, the area under the ROC curve (AUC) was the primary accuracy metric. AUC was computed using cross validation. Accuracy was computed for models that substituted one gene at a time. In this example, PLAUR was substituted for TNFAIP6 in all relevant terms of the algorithm. Summary statistics for the calculations are shown in Table 15. AUC's greater than the upper bound of the confidence interval for the AUC of Diamond Forrester (DF) were considered significantly better than the DF model. See Table 16 for DF AUC. The algorithm with the substitute marker remained significantly better than the DF model indicating that the algorithm remains predictive of the likelihood of CAD even after replacement of the algorithm marker with the highly correlated substitute marker.

Example 20

Replacement of AQP9 with a Highly Correlated Substitute Marker

For each algorithm marker, a highly correlated, non-algorithm substitute marker was identified from the Phase III PCR data set described above. For each marker, a Pearson correlation value between that marker and all other markers was computed and then we picked the substitute marker with maximal correlation to the algorithm marker of interest. This substitute was the marker with the highest correlation to the algorithm marker, subject to the restriction that a substitute marker was not used more than once in the terms of the algorithm. The correlation value for this particular replacement is shown in Table 15. Two statistical methods were used for the analysis: logistic regression and ridge regression. For the analysis, the area under the ROC curve (AUC) was the primary accuracy metric. AUC was computed using cross validation. Accuracy was computed for models that substituted one gene at a time. In this example, GLT1D1 was substituted for AQP9 in all relevant terms of the algorithm. Summary statistics for the calculations are shown in Table 15. AUC's greater than the upper bound of the confidence interval for the AUC of Diamond Forrester (DF) were considered significantly better than the DF model. See Table 16 for DF AUC. The algorithm with the substitute marker remained significantly better than the DF model indicating that the

Example 21

Replacement of NCF4 with a Highly Correlated Substitute Marker

For each algorithm marker, a highly correlated, non-algorithm substitute marker was identified from the Phase III PCR data set described above. For each marker, a Pearson correlation value between that marker and all other markers was computed and then we picked the substitute marker with maximal correlation to the algorithm marker of interest. This substitute was the marker with the highest correlation to the algorithm marker, subject to the restriction that a substitute marker was not used more than once in the terms of the algorithm. The correlation value for this particular replacement is shown in Table 15. Two statistical methods were used for the analysis: logistic regression and ridge regression. For the analysis, the area under the ROC curve (AUC) was the primary accuracy metric. AUC was computed using cross validation. Accuracy was computed for models that substituted one gene at a time. In this example, NCF2 was substituted for NCF4 in all relevant terms of the algorithm. Summary statistics for the calculations are shown in Table 15. AUC's greater than the upper bound of the confidence interval for the AUC of Diamond Forrester (DF) were considered significantly better than the DF model. See Table 16 for DF AUC. The algorithm with the substitute marker remained significantly better than the DF model indicating that the algorithm remains predictive of the likelihood of CAD even after replacement of the algorithm marker with the highly correlated substitute marker.

Example 22

Replacement of CD3D with a Highly Correlated Substitute Marker

For each algorithm marker, a highly correlated, non-algorithm substitute marker was identified from the Phase III PCR data set described above. For each marker, a Pearson correlation value between that marker and all other markers was computed and then we picked the substitute marker with maximal correlation to the algorithm marker of interest. This substitute was the marker with the highest correlation to the algorithm marker, subject to the restriction that a substitute marker was not used more than once in the terms of the algorithm. The correlation value for this particular replacement is shown in Table 15. Two statistical methods were used for the analysis: logistic regression and ridge regression. For the analysis, the area under the ROC curve (AUC) was the primary accuracy metric. AUC was computed using cross validation. Accuracy was computed for models that substituted one gene at a time. In this example, LCK was substituted for CD3D in all relevant terms of the algorithm. Summary statistics for the calculations are shown in Table 15. AUC's greater than the upper bound of the confidence interval for the AUC of Diamond Forrester (DF) were considered significantly better than the DF model. See Table 16 for DF AUC. The algorithm with the substitute marker remained significantly better than the DF model indicating that the algorithm remains predictive of the likelihood of CAD even after replacement of the algorithm marker with the highly correlated substitute marker.

Example 23

Replacement of TMC8 with a Highly Correlated Substitute Marker

For each algorithm marker, a highly correlated, non-algorithm substitute marker was identified from the Phase III PCR data set described above. For each marker, a Pearson correlation value between that marker and all other markers was computed and then we picked the substitute marker with maximal correlation to the algorithm marker of interest. This substitute was the marker with the highest correlation to the algorithm marker, subject to the restriction that a substitute marker was not used more than once in the terms of the algorithm. The correlation value for this particular replacement is shown in Table 15. Two statistical methods were used for the analysis: logistic regression and ridge regression. For the analysis, the area under the ROC curve (AUC) was the primary accuracy metric. AUC was computed using cross validation. Accuracy was computed for models that substituted one gene at a time. In this example, CCT2 was substituted for TMC8 in all relevant terms of the algorithm. Summary statistics for the calculations are shown in Table 15. AUC's greater than the upper bound of the confidence interval for the AUC of Diamond Forrester (DF) were considered significantly better than the DF model. See Table 16 for DF AUC. The algorithm with the substitute marker remained significantly better than the DF model indicating that the algorithm remains predictive of the likelihood of CAD even after replacement of the algorithm marker with the highly correlated substitute marker.

Example 24

Replacement of CD79B with a Highly Correlated Substitute Marker

For each algorithm marker, a highly correlated, non-algorithm substitute marker was identified from the Phase III PCR data set described above. For each marker, a Pearson correlation value between that marker and all other markers was computed and then we picked the substitute marker with maximal correlation to the algorithm marker of interest. This substitute was the marker with the highest correlation to the algorithm marker, subject to the restriction that a substitute marker was not used more than once in the terms of the algorithm. The correlation value for this particular replacement is shown in Table 15. Two statistical methods were used for the analysis: logistic regression and ridge regression. For the analysis, the area under the ROC curve (AUC) was the primary accuracy metric. AUC was computed using cross validation. Accuracy was computed for models that substituted one gene at a time. In this example, CD19 was substituted for CD79B in all relevant terms of the algorithm. Summary statistics for the calculations are shown in Table 15. AUC's greater than the upper bound of the confidence interval for the AUC of Diamond Forrester (DF) were considered significantly better than the DF model. See Table 16 for DF AUC. The algorithm with the substitute marker remained significantly better than the DF model indicating that the algorithm remains predictive of the likelihood of CAD even after replacement of the algorithm marker with the highly correlated substitute marker.

Example 25

Replacement of SPIB with a Highly Correlated Substitute Marker

For each algorithm marker, a highly correlated, non-algorithm substitute marker was identified from the Phase III PCR data set described above. For each marker, a Pearson correlation value between that marker and all other markers was computed and then we picked the substitute marker with maximal correlation to the algorithm marker of interest. This substitute was the marker with the highest correlation to the algorithm marker, subject to the restriction that a substitute marker was not used more than once in the terms of the algorithm. The correlation value for this particular replacement is shown in Table 15. Two statistical methods were used for the analysis: logistic regression and ridge regression. For the analysis, the area under the ROC curve (AUC) was the primary accuracy metric. AUC was computed using cross validation. Accuracy was computed for models that substituted one gene at a time. In this example, BLK was substituted for SPIB in all relevant terms of the algorithm. Summary statistics for the calculations are shown in Table 15. AUC's greater than the upper bound of the confidence interval for the AUC of Diamond Forrester (DF) were considered significantly better than the DF model. See Table 16 for DF AUC. The algorithm with the substitute marker remained significantly better than the DF model indicating that the algorithm remains predictive of the likelihood of CAD even after replacement of the algorithm marker with the highly correlated substitute marker.

Example 26

Replacement of HNRPF with a Highly Correlated Substitute Marker

For each algorithm marker, a highly correlated, non-algorithm substitute marker was identified from the Phase III PCR data set described above. For each marker, a Pearson correlation value between that marker and all other markers was computed and then we picked the substitute marker with maximal correlation to the algorithm marker of interest. This substitute was the marker with the highest correlation to the algorithm marker, subject to the restriction that a substitute marker was not used more than once in the terms of the algorithm. The correlation value for this particular replacement is shown in Table 15. Two statistical methods were used for the analysis: logistic regression and ridge regression. For the analysis, the area under the ROC curve (AUC) was the primary accuracy metric. AUC was computed using cross validation. Accuracy was computed for models that substituted one gene at a time. In this example, ACBD5 was substituted for HNRPF in all relevant terms of the algorithm. Summary statistics for the calculations are shown in Table 15. AUC's greater than the upper bound of the confidence interval for the AUC of Diamond Forrester (DF) were considered significantly better than the DF model. See Table 16 for DF AUC. The algorithm with the substitute marker remained significantly better than the DF model indicating that the algorithm remains predictive of the likelihood of CAD even after replacement of the algorithm marker with the highly correlated substitute marker.

Example 27

Replacement of TFCP2 with a Highly Correlated Substitute Marker

For each algorithm marker, a highly correlated, non-algorithm substitute marker was identified from the Phase III PCR data set described above. For each marker, a Pearson correlation value between that marker and all other markers was computed and then we picked the substitute marker with maximal correlation to the algorithm marker of interest. This substitute was the marker with the highest correlation to the algorithm marker, subject to the restriction that a substitute marker was not used more than once in the terms of the algorithm. The correlation value for this particular replacement is shown in Table 15. Two statistical methods were used for the analysis: logistic regression and ridge regression. For the analysis, the area under the ROC curve (AUC) was the primary accuracy metric. AUC was computed using cross validation. Accuracy was computed for models that substituted one gene at a time. In this example, DDX18 was substituted for TFCP2 in all relevant terms of the algorithm. Summary statistics for the calculations are shown in Table 15. AUC's greater than the upper bound of the confidence interval for the AUC of Diamond Forrester (DF) were considered significantly better than the DF model. See Table 16 for DF AUC. The algorithm with the substitute marker remained significantly better than the DF model indicating that the algorithm remains predictive of the likelihood of CAD even after replacement of the algorithm marker with the highly correlated substitute marker.

Example 28

Replacement of RPL28 with a Highly Correlated Substitute Marker

For each algorithm marker, a highly correlated, non-algorithm substitute marker was identified from the Phase III PCR data set described above. For each marker, a Pearson correlation value between that marker and all other markers was computed and then we picked the substitute marker with maximal correlation to the algorithm marker of interest. This substitute was the marker with the highest correlation to the algorithm marker, subject to the restriction that a substitute marker was not used more than once in the terms of the algorithm. The correlation value for this particular replacement is shown in Table 15. Two statistical methods were used for the analysis: logistic regression and ridge regression. For the analysis, the area under the ROC curve (AUC) was the primary accuracy metric. AUC was computed using cross validation. Accuracy was computed for models that substituted one gene at a time. In this example, SSRP1 was substituted for RPL28 in all relevant terms of the algorithm. Summary statistics for the calculations are shown in Table 15. AUC's greater than the upper bound of the confidence interval for the AUC of Diamond Forrester (DF) were considered significantly better than the DF model. See Table 16 for DF AUC. The algorithm with the substitute marker remained significantly better than the DF model indicating that the algorithm remains predictive of the likelihood of CAD even after replacement of the algorithm marker with the highly correlated substitute marker.

Example 29

Replacement of AF289562 with a Highly Correlated Substitute Marker

For each algorithm marker, a highly correlated, non-algorithm substitute marker was identified from the Phase III PCR data set described above. For each marker, a Pearson correlation value between that marker and all other markers was computed and then we picked the substitute marker with maximal correlation to the algorithm marker of interest. This substitute was the marker with the highest correlation to the algorithm marker, subject to the restriction that a substitute marker was not used more than once in the terms of the algorithm. The correlation value for this particular replacement is shown in Table 15. Two statistical methods were used for the analysis: logistic regression and ridge regression. For the analysis, the area under the ROC curve (AUC) was the primary accuracy metric. AUC was computed using cross validation. Accuracy was computed for models that substituted one gene at a time. In this example, CD248 was substituted for AF289562 in all relevant terms of the algorithm. Summary statistics for the calculations are shown in Table 15. AUC's greater than the upper bound of the confidence interval for the AUC of Diamond Forrester (DF) were considered significantly better than the DF model. See Table 16 for DF AUC. The algorithm with the substitute marker remained significantly better than the DF model indicating that the algorithm remains predictive of the likelihood of CAD even after replacement of the algorithm marker with the highly correlated substitute marker.

Example 30

Replacement of SLAMF7 with a Highly Correlated Substitute Marker

For each algorithm marker, a highly correlated, non-algorithm substitute marker was identified from the Phase III PCR data set described above. For each marker, a Pearson correlation value between that marker and all other markers was computed and then we picked the substitute marker with maximal correlation to the algorithm marker of interest. This substitute was the marker with the highest correlation to the algorithm marker, subject to the restriction that a substitute marker was not used more than once in the terms of the algorithm. The correlation value for this particular replacement is shown in Table 15. Two statistical methods were used for the analysis: logistic regression and ridge regression. For the analysis, the area under the ROC curve (AUC) was the primary accuracy metric. AUC was computed using cross validation. Accuracy was computed for models that substituted one gene at a time. In this example, CX3CR1 was substituted for SLAMF7 in all relevant terms of the algorithm. Summary statistics for the calculations are shown in Table 15. AUC's greater than the upper bound of the confidence interval for the AUC of Diamond Forrester (DF) were considered significantly better than the DF model. See Table 16 for DF AUC. The algorithm with the substitute marker remained significantly better than the DF model indicating that the algorithm remains predictive of the likelihood of CAD even after replacement of the algorithm marker with the highly correlated substitute marker.

Example 31

Replacement of KLRC4 with a Highly Correlated Substitute Marker

For each algorithm marker, a highly correlated, non-algorithm substitute marker was identified from the Phase III PCR data set described above. For each marker, a Pearson correlation value between that marker and all other markers was computed and then we picked the substitute marker with maximal correlation to the algorithm marker of interest. This substitute was the marker with the highest correlation to the algorithm marker, subject to the restriction that a substitute marker was not used more than once in the terms of the algorithm. The correlation value for this particular replacement is shown in Table 15. Two statistical methods were used for the analysis: logistic regression and ridge regression. For the analysis, the area under the ROC curve (AUC) was the primary accuracy metric. AUC was computed using cross validation. Accuracy was computed for models that substituted one gene at a time. In this example, CD8A was substituted for KLRC4 in all relevant terms of the algorithm. Summary statistics for the calculations are shown in Table 15. AUC's greater than the upper bound of the confidence interval for the AUC of Diamond Forrester (DF) were considered significantly better than the DF model. See Table 16 for DF AUC. The algorithm with the substitute marker remained significantly better than the DF model indicating that the algorithm remains predictive of the likelihood of CAD even after replacement of the algorithm marker with the highly correlated substitute marker.

Example 32

Replacement of IL8RB with a Highly Correlated Substitute Marker

For each algorithm marker, a highly correlated, non-algorithm substitute marker was identified from the Phase III PCR data set described above. For each marker, a Pearson correlation value between that marker and all other markers was computed and then we picked the substitute marker with maximal correlation to the algorithm marker of interest. This substitute was the marker with the highest correlation to the algorithm marker, subject to the restriction that a substitute marker was not used more than once in the terms of the algorithm. The correlation value for this particular replacement is shown in Table 15. Two statistical methods were used for the analysis: logistic regression and ridge regression. For the analysis, the area under the ROC curve (AUC) was the primary accuracy metric. AUC was computed using cross validation. Accuracy was computed for models that substituted one gene at a time. In this example, BCL2A1 was substituted for IL8RB in all relevant terms of the algorithm. Summary statistics for the calculations are shown in Table 15. AUC's greater than the upper bound of the confidence interval for the AUC of Diamond Forrester (DF) were considered significantly better than the DF model. See Table 16 for DF AUC. The algorithm with the substitute marker remained significantly better than the DF model indicating that the algorithm remains predictive of the likelihood of CAD even after replacement of the algorithm marker with the highly correlated substitute marker.

Example 33

Replacement of TNFRSF10C with a Highly Correlated Substitute Marker

For each algorithm marker, a highly correlated, non-algorithm substitute marker was identified from the Phase III PCR data set described above. For each marker, a Pearson correlation value between that marker and all other markers was computed and then we picked the substitute marker with maximal correlation to the algorithm marker of interest. This substitute was the marker with the highest correlation to the algorithm marker, subject to the restriction that a substitute marker was not used more than once in the terms of the algorithm. The correlation value for this particular replacement is shown in Table 15. Two statistical methods were used for the analysis: logistic regression and ridge regression. For the analysis, the area under the ROC curve (AUC) was the primary accuracy metric. AUC was computed using cross validation. Accuracy was computed for models that substituted one gene at a time. In this example, PTAFR was substituted for TNFRSF10C in all relevant terms of the algorithm. Summary statistics for the calculations are shown in Table 15. AUC's greater than the upper bound of the confidence interval for the AUC of Diamond Forrester (DF) were considered significantly better than the DF model. See Table 16 for DF AUC. The algorithm with the substitute marker remained significantly better than the DF model indicating that the algorithm remains predictive of the likelihood of CAD even after replacement of the algorithm marker with the highly correlated substitute marker.

Example 34

Replacement of KCNE3 with a Highly Correlated Substitute Marker

For each algorithm marker, a highly correlated, non-algorithm substitute marker was identified from the Phase III PCR data set described above. For each marker, a Pearson correlation value between that marker and all other markers was computed and then we picked the substitute marker with maximal correlation to the algorithm marker of interest. This substitute was the marker with the highest correlation to the algorithm marker, subject to the restriction that a substitute marker was not used more than once in the terms of the algorithm. The correlation value for this particular replacement is shown in Table 15. Two statistical methods were used for the analysis: logistic regression and ridge regression. For the analysis, the area under the ROC curve (AUC) was the primary accuracy metric. AUC was computed using cross validation. Accuracy was computed for models that substituted one gene at a time. In this example, LAMP2 was substituted for KCNE3 in all relevant terms of the algorithm. Summary statistics for the calculations are shown in Table 15. AUC's greater than the upper bound of the confidence interval for the AUC of Diamond Forrester (DF) were considered significantly better than the DF model. See Table 16 for DF AUC. The algorithm with the substitute marker remained significantly better than the DF model indicating that the algorithm remains predictive of the likelihood of CAD even after replacement of the algorithm marker with the highly correlated substitute marker.

Example 35

Replacement of TLR4 with a Highly Correlated Substitute Marker

For each algorithm marker, a highly correlated, non-algorithm substitute marker was identified from the Phase III PCR data set described above. For each marker, a Pearson correlation value between that marker and all other markers was computed and then we picked the substitute marker with maximal correlation to the algorithm marker of interest. This substitute was the marker with the highest correlation to the algorithm marker, subject to the restriction that a substitute marker was not used more than once in the terms of the algorithm. The correlation value for this particular replacement is shown in Table 15. Two statistical methods were used for the analysis: logistic regression and ridge regression. For the analysis, the area under the ROC curve (AUC) was the primary accuracy metric. AUC was computed using cross validation. Accuracy was computed for models that substituted one gene at a time. In this example, TYROBP was substituted for TLR4 in all relevant terms of the algorithm. Summary statistics for the calculations are shown in Table 15. AUC's greater than the upper bound of the confidence interval for the AUC of Diamond Forrester (DF) were considered significantly better than the DF model. See Table 16 for DF AUC. The algorithm with the substitute marker remained significantly better than the DF model indicating that the algorithm remains predictive of the likelihood of CAD even after replacement of the algorithm marker with the highly correlated substitute marker.

Example 36

Random Replacement of Five Algorithm Markers with Five Distinct, Highly Correlated Substitute Markers For each algorithm marker, a highly correlated, non-algorithm substitute marker was identified from the Phase III PCR data set described above. For each marker, a Pearson correlation value between that marker and all other markers was computed and then we picked the substitute marker with maximal correlation to the algorithm marker of interest. This substitute was the marker with the highest correlation to the algorithm marker, subject to the restriction that a substitute marker was not used more than once in the terms of the algorithm. See Table 15 for the highly correlated substitute markers. Two statistical methods were used for the analysis: logistic regression and ridge regression. For the analysis, the area under the ROC curve (AUC) was the primary accuracy metric. AUC was computed using cross validation. Accuracy was computed for models that randomly substituted five highly correlated markers at a time for five distinct algorithm markers. For the random marker substitutions, 100 iterations each were run and the mean and the standard deviation were calculated. Summary statistics for the calculations are shown in Table 16. AUC's greater than the upper bound of the confidence interval for the AUC of Diamond Forrester (DF) are considered significantly better than the DF model. The algorithm with the substitute markers remained significantly better than the DF model indicating that the algorithm remains predictive of the likelihood of CAD even after replacement of five algorithm markers with five highly correlated substitute markers.

Example 37

Random Replacement of Ten Algorithm Markers with Ten Distinct, Highly Correlated Substitute Markers For each algorithm marker, a highly correlated, non-algorithm substitute marker was identified from the Phase III PCR data set described above. For each marker, a Pearson correlation value between that marker and all other markers was computed and then we picked the substitute marker with maximal correlation to the algorithm marker of interest. This substitute was the marker with the highest correlation to the algorithm marker, subject to the restriction that a substitute marker was not used more than once in the terms of the algorithm. See Table 15 for the highly correlated substitute markers. Two statistical methods were used for the analysis: logistic regression and ridge regression. For the analysis, the area under the ROC curve (AUC) was the primary accuracy metric. AUC was computed using cross validation. Accuracy was computed for models that randomly substituted ten highly correlated markers at a time for ten distinct algorithm markers. For the random marker substitutions, 100 iterations each were run and the mean and the standard deviation were calculated. Summary statistics for the calculations are shown in Table 16. AUC's greater than the upper bound of the confidence interval for the AUC of Diamond Forrester (DF) are considered significantly better than the DF model. The algorithm with the substitute markers remained significantly better than the DF model indicating that the algorithm remains predictive of the likelihood of CAD even after replacement of ten algorithm markers with ten highly correlated substitute markers.

Example 38

Random Replacement of Fifteen Algorithm Markers with Fifteen Distinct, Highly Correlated Substitute Markers For each algorithm marker, a highly correlated, non-algorithm substitute marker was identified from the Phase III PCR data set described above. For each marker, a Pearson correlation value between that marker and all other markers was computed and then we picked the substitute marker with maximal correlation to the algorithm marker of interest. This substitute was the marker with the highest correlation to the algorithm marker, subject to the restriction that a substitute marker was not used more than once in the terms of the algorithm. See Table 15 for the highly correlated substitute markers. Two statistical methods were used for the analysis: logistic regression and ridge regression. For the analysis, the area under the ROC curve (AUC) was the primary accuracy metric. AUC was computed using cross validation. Accuracy was computed for models that randomly substituted fifteen highly correlated markers at a time for fifteen distinct algorithm markers. For the random marker substitutions, 100 iterations each were run and the mean and the standard deviation were calculated. Summary statistics for the calculations are shown in Table 16. AUC's greater than the upper bound of the confidence interval for the AUC of Diamond Forrester (DF) are considered significantly better than the DF model. The algorithm with the substitute markers remained significantly better than the DF model indicating that the algorithm remains predictive of the likelihood of CAD even after replacement of fifteen algorithm markers with fifteen highly correlated substitute markers.

Example 39

Random Replacement of Twenty Algorithm Markers with Twenty Distinct, Highly Correlated Substitute Markers For each algorithm marker, a highly correlated, non-algorithm substitute marker was identified from the Phase III PCR data set described above. For each marker, a Pearson correlation value between that marker and all other markers was computed and then we picked the substitute marker with maximal correlation to the algorithm marker of interest. This substitute was the marker with the highest correlation to the algorithm marker, subject to the restriction that a substitute marker was not used more than once in the terms of the algorithm. See Table 15 for the highly correlated substitute markers. Two statistical methods were used for the analysis: logistic regression and ridge regression. For the analysis, the area under the ROC curve (AUC) was the primary accuracy metric. AUC was computed using cross validation. Accuracy was computed for models that randomly substituted twenty highly correlated markers at a time for twenty distinct algorithm markers. For the random marker substitutions, 100 iterations each were run and the mean and the standard deviation were calculated. Summary statistics for the calculations are shown in Table 16. AUC's greater than the upper bound of the confidence interval for the AUC of Diamond Forrester (DF) are considered significantly better than the DF model. The algorithm with the substitute markers remained significantly better than the DF model indicating that the algorithm remains predictive of the likelihood of CAD even after replacement of twenty algorithm markers with twenty highly correlated substitute markers.

Example 40

Random Replacement of all Algorithm Markers with Distinct, Highly Correlated Substitute Markers For each algorithm marker, a highly correlated, non-algorithm substitute marker was identified from the Phase III PCR data set described above. For each marker, a Pearson correlation value between that marker and all other markers was computed and then we picked the substitute marker with maximal correlation to the algorithm marker of interest. This substitute was the marker with the highest correlation to the algorithm marker, subject to the restriction that a substitute marker was not used more than once in the terms of the algorithm. See Table 15 for the highly correlated substitute markers. Two statistical methods were used for the analysis: logistic regression and ridge regression. For the analysis, the area under the ROC curve (AUC) was the primary accuracy metric. AUC was computed using cross validation. Accuracy was computed for models that randomly substituted highly correlated markers at a time for all algorithm markers. For the random marker substitutions, 100 iterations each were run and the mean was calculated. Summary statistics for the calculations are shown in Table 16. AUC's greater than the upper bound of the confidence interval for the AUC of Diamond Forrester (DF) are considered significantly better than the DF model. The algorithm with the substitute markers remained significantly better than the DF model indicating that the algorithm remains predictive of the likelihood of CAD even after replacement of all algorithm markers with highly correlated substitute markers.

Example 41

Removal of Markers from Term 1

Term 1 algorithm and highly correlated substitute markers were sequentially removed from the algorithm to determine whether the algorithm would remain predictive of the likelihood of CAD in their absence. All other terms and their associated markers were removed from the algorithm, thus in this analysis each term was considered on its own. Each term on the model is a delta term, with n_i markers on the left side of the delta term and m_i markers on the right side of the delta term. We examined two marker 'reduced terms' where only one of the n_i left-hand side markers and one of the possible m_i right-hand side markers was used in the term. There were thus n_i*m_i possible two marker reduced terms. We also examined 'reduced terms' produced by the sequential removal of markers from the full term for both the algorithm markers as well as the substitute markers.

For each of the reduced terms, models were fit including gender, age, and the reduced term, and cross-validated AUC's were estimated. These cross validated AUC's were compared to the AUC's from a model that included gender, age, and the full term. For each reduced term, we tested whether there was still a statistically significant predictive effect of the term, i.e., whether the decrease in AUC was sufficient to render the marker reduced set not beneficial in prediction of CAD. The same process was repeated for all reduced marker sets where correlated replacement markers were used in place of original algorithm markers.

We found that all reduced terms produced in this analysis remained predictive of CAD. See Table 17.

Example 42

Removal of Markers from Term 2

Term 2 algorithm and highly correlated substitute markers were sequentially removed from the algorithm to determine whether the algorithm would remain predictive of the likelihood of CAD in their absence. All other terms and their associated markers were removed from the algorithm, thus in this analysis each term was considered on its own. Each term on the model is a delta term, with n_i markers on the left side of the delta term and m_i markers on the right side of the delta term. We examined two marker 'reduced terms' where only one of the n_i left-hand side markers and one of the possible m_i right-hand side markers was used in the term. There were thus n_i*m_i possible two marker reduced terms. We also examined 'reduced terms' produced by the sequential removal of markers from the full term for both the algorithm markers as well as the substitute markers.

For each of the reduced terms, models were fit including gender, age, and the reduced term, and cross-validated AUC's were estimated. These cross validated AUC's were compared to the AUC's from a model that included gender, age, and the full term. For each reduced term, we tested whether there was still a statistically significant predictive effect of the term, i.e., whether the decrease in AUC was sufficient to render the marker reduced set not beneficial in prediction of CAD. The same process was repeated for all reduced marker sets where correlated replacement markers were used in place of original algorithm markers.

We found that all reduced terms produced in this analysis remained predictive of CAD. See Table 18.

Example 43

Removal of Markers from Term 3

Term 3 algorithm and highly correlated substitute markers were sequentially removed from the algorithm to determine whether the algorithm would remain predictive of the likelihood of CAD in their absence. All other terms and their associated markers were removed from the algorithm, thus in this analysis each term was considered on its own. Each term on the model is a delta term, with n_i markers on the left side of the delta term and m_i markers on the right side of the delta term. We examined two marker 'reduced terms' where only one of the n_i left-hand side markers and one of the possible m_i right-hand side markers was used in the term. There were thus n_i*m_i possible two marker reduced terms. We also examined 'reduced terms' produced by the sequential removal of markers from the full term for both the algorithm markers as well as the substitute markers.

For each of the reduced terms, models were fit including gender, age, and the reduced term, and cross-validated AUC's were estimated. These cross validated AUC's were compared to the AUC's from a model that included gender, age, and the full term. For each reduced term, we tested whether there was still a statistically significant predictive effect of the term, i.e., whether the decrease in AUC was sufficient to render the marker reduced set not beneficial in prediction of CAD. The same process was repeated for all reduced marker sets where correlated replacement markers were used in place of original algorithm markers. In addition, for the two marker reduced sets, the same process was repeated again where one correlated replacement marker was used along with one original algorithm marker.

We found that all reduced terms produced in this analysis remained predictive of CAD, except for: LCK/CCT2/CD19/BLK; LCK/CD19/BLK; CCT2/CD19/BLK; LCK/CCT2/CD19; LCK/CD19; CCT2/CD19; CD3D/CD19; LCK/CD19; and CCT2/CD19. See Table 19. TMC8/CD19 was predictive of CAD when AUC using Ridge regression was calculated, but not when AUC using Logistic Regression was calculated. See Table 19.

Example 44

Removal of Markers from Term 4

Term 4 algorithm and highly correlated substitute markers were sequentially removed from the algorithm to determine whether the algorithm would remain predictive of the likelihood of CAD in their absence. All other terms and their associated markers were removed from the algorithm, thus in this analysis each term was considered on its own. Each term on the model is a delta term, with n_i markers on the left side of the delta term and m_i markers on the right side of the delta term. We examined two marker 'reduced terms' where only one of the n_i left-hand side markers and one of the possible m_i right-hand side markers was used in the term. There were thus n_i*m_i possible two marker reduced terms. We also examined 'reduced terms' produced by the sequential removal of markers from the full term for both the algorithm markers as well as the substitute markers.

For each of the reduced terms, models were fit including gender, age, and the reduced term, and cross-validated AUC's were estimated. These cross validated AUC's were compared to the AUC's from a model that included gender, age, and the full term. For each reduced term, we tested whether there was still a statistically significant predictive effect of the term, i.e., whether the decrease in AUC was sufficient to render the marker reduced set not beneficial in prediction of CAD. The same process was repeated for all reduced marker sets where correlated replacement markers were used in place of original algorithm markers.

We found that all reduced terms produced in this analysis remained predictive of CAD. See Table 20.

Example 45

Removal of Markers from Term 5

Term 5 algorithm and highly correlated substitute markers were sequentially removed from the algorithm to determine whether the algorithm would remain predictive of the likelihood of CAD in their absence. All other terms and their associated markers were removed from the algorithm, thus in this analysis each term was considered on its own. Each term on the model is a delta term, with n_i markers on the left side of the delta term and m_i markers on the right side of the delta term. We examined two marker 'reduced terms' where only one of the n_i left-hand side markers and one of the possible m_i right-hand side markers was used in the term. There were thus n_i*m_i possible two marker reduced terms. We also examined 'reduced terms' produced by the sequential removal of markers from the full term for both the algorithm markers as well as the substitute markers.

For each of the reduced terms, models were fit including gender, age, and the reduced term, and cross-validated AUC's were estimated. These cross validated AUC's were compared to the AUC's from a model that included gender, age, and the full term. For each reduced term, we tested whether there was still a statistically significant predictive effect of the term, i.e., whether the decrease in AUC was sufficient to render the marker reduced set not beneficial in prediction of CAD. The same process was repeated for all reduced marker sets where correlated replacement markers were used in place of original algorithm markers. In addition, for the two marker reduced sets, the same process was repeated again where one correlated replacement marker was used along with one original algorithm marker.

We found that all reduced terms produced in this analysis remained predictive of CAD, except for: MMP9/ALOX5AP/GLT1D1/NCF2; MMP9/ALOX5AP/NAMPT/NCF2; MMP9/GLT1D1/NCF2; MMP9/ALOX5AP/NCF2; MMP9/NAMPT/NCF2; MMP9/GLT1D1; ALOX5AP/NCF2; MMP9/NCF2; ALOX5AP/AQP9; and ALOX5AP/NCF2. See Table 21. ALOX5AP/NCF4 was predictive of CAD when AUC using Ridge regression was calculated, but not when AUC using Logistic Regression was calculated. See Table 21.

Example 46

Removal of Markers from Term 6

Term 6 algorithm and highly correlated substitute markers were sequentially removed from the algorithm to determine whether the algorithm would remain predictive of the likelihood of CAD in their absence. All other terms and their associated markers were removed from the algorithm, thus in this analysis each term was considered on its own. Each term on the model is a delta term, with n_i markers on the left side of the delta term and m_i markers on the right side of the delta term. We examined two marker 'reduced terms' where only one of the n_i left-hand side markers and one of the possible m_i right-hand side markers was used in the term. There were thus n_i*m_i possible two marker reduced terms. We also examined 'reduced terms' produced by the sequential removal of markers from the full term for both the algorithm markers as well as the substitute markers.

For each of the reduced terms, models were fit including gender, age, and the reduced term, and cross-validated AUC's were estimated. These cross validated AUC's were compared to the AUC's from a model that included gender, age, and the full term. For each reduced term, we tested whether there was still a statistically significant predictive effect of the term, i.e., whether the decrease in AUC was sufficient to render the marker reduced set not beneficial in prediction of CAD. The same process was repeated for all reduced marker sets where correlated replacement markers were used in place of original algorithm markers. In addition, for the two marker reduced sets, the same process was repeated again where one correlated replacement marker was used along with one original algorithm marker.

We found that all reduced terms produced in this analysis remained predictive of CAD, except for: H3F3B/TXN/BCL2A1/LAMP2/TYROBP; H3F3B/TXN/BCL2A1/LAMP2; H3F3B/TXN/BCL2A1/TYROBP; TXN/PLAUR/BCL2A1/TYROBP; H3F3B/TXN/PLAUR/BCL2A1; H3F3B/BCL2A1/TYROBP; TXN/BCL2A1/TYROBP; H3F3B/TXN/BCL2A1; H3F3B/TXN/TYROBP; TXN/PLAUR/BCL2A1; TXN/PLAUR/BCL2A1; H3F3B/BCL2A1; H3F3B/TYROBP; TXN/BCL2A1; TXN/TYROBP; TXN/IL8RB; and TXN/TNFRSF10C. See Table 22.

Example 47

Removal of Markers from Term 7

Term 7 algorithm and highly correlated substitute markers were sequentially removed from the algorithm to determine whether the algorithm would remain predictive of the likelihood of CAD in their absence. All other terms and their associated markers were removed from the algorithm, thus in this analysis each term was considered on its own. Each term on the model is a delta term, with n_i markers on the left side of the delta term and m_i markers on the right side of the delta term. We examined two marker 'reduced terms' where only one of the n_i left-hand side markers and one of the possible m_i right-hand side markers was used in the term. There were thus n_i*m_i possible two marker reduced terms. We also examined 'reduced terms' produced by the sequential removal of markers from the full term for both the algorithm markers as well as the substitute markers.

For each of the reduced terms, models were fit including gender, age, and the reduced term, and cross-validated AUC's were estimated. These cross validated AUC's were compared to the AUC's from a model that included gender, age, and the full term. For each reduced term, we tested whether there was still a statistically significant predictive effect of the term, i.e., whether the decrease in AUC was sufficient to render the marker reduced set not beneficial in prediction of CAD. The same process was repeated for all reduced marker sets where correlated replacement markers were used in place of original algorithm markers. In addition, for the two marker reduced sets, the same process was repeated again where one correlated replacement marker was used along with one original algorithm marker.

We found that all reduced terms produced in this analysis remained predictive of CAD, except for: LCK/CCT2/CX3CR1/CD8A; LCK/CX3CR1/CD8A; CCT2/CX3CR1/CD8A; LCK/CCT2/CD8A; LCK/CD8A; CCT2/CD8A; TMC8/CD8A; and CD3D/CD8A. See Table 23.

Example 48

Validation of the Diagnostic Accuracy of the Algorithm for Assessment of CAD in Non-Diabetic Patients Herein we report initial prospective validation of a gene expression algorithm for the likelihood of obstructive CAD, defined as one or more coronary atherosclerotic lesions causing ≥50% luminal diameter stenosis, in non-diabetic patients with suspected CAD.

Methods

General Study Design and Study Population

Subjects were enrolled in PREDICT, a 39 center (US) prospective study, between July 2007 and April 2009. The study was approved at the institutional review board at all participating centers and all patients gave written informed consent. Subjects referred for diagnostic coronary angiography were eligible if they had a history of chest pain, suspected anginal-equivalent symptoms, or a high risk of CAD, and no known prior myocardial infarction (MI), revascularization, or obstructive CAD. Subjects were ineligible if at catheterization, they had acute MI, high risk unstable angina, severe non-coronary heart disease (congestive heart failure, cardiomyopathy or valve disease), systemic infectious or inflammatory conditions, or were taking immunosuppressive or chemotherapeutic agents.

From 2418 enrolled subjects who met inclusion criteria, 606 diabetic patients were excluded, as this initial algorithm development and validation was focused on non-diabetics. Of the remaining 1812 patients, 237 had angiographic images unsuitable for QCA and 6 had unusable blood samples. For the remaining 1569 subjects, 226 were used in gene discovery (Elashoff M R, Wingrove J A, Beineke P, et al. Development of a Blood-based Gene Expression Algorithm for Assessment of Obstructive Coronary Artery Disease in Non-Diabetic Patients, submitted. Circulation: Cardiovascular Genetics. 2010); the remaining 1343 were divided into independent algorithm development and validation cohorts (FIG. 7) sequentially based on date of enrollment.

Clinical Evaluation and Quantitative Coronary Angiography

Pre-specified clinical data, including demographics, medications, clinical history and presentation, and MPI results were obtained by research study coordinators at study sites using standardized data collection methods and data were verified by independent study monitors.

Coronary angiograms were analyzed by computer-assisted QCA. Specifically, clinically-indicated coronary angiograms performed according to site protocols were digitized, de-identified and analyzed with a validated quantitative protocol at Cardiovascular Research Foundation, New York, N.Y. (Lansky A J, Popma J J. *Qualitative and quantitative angiography* Philadelphia, Pa.: Saunders; 1998 Text Book of Interventional Cardiology)). Trained technicians, blinded to clinical and gene expression data, visually identified all lesions >10% diameter stenosis (DS) in vessels with diameter >1.5 mm Using the CMS Medis system, (Medis, version 7.1, Leiden, the Netherlands), technicians traced the vessel lumen across the lesion between the nearest proximal and distal non-diseased locations. The minimal lumen diameter (MLD), reference lumen diameter (RLD=average diameter of normal segments proximal and distal of lesion) and % DS (% DS=(1−MLD/RLD)×100) were then calculated.

The Diamond-Forrester (D-F) risk score, comprised of age, sex, and chest pain type, was prospectively chosen to evaluate the added value of the gene expression score to clinical factors (Diamond G A, Forrester J S. Analysis of probability as an aid in the clinical diagnosis of coronary-artery disease. *N Engl J Med.* 1979; 300(24):1350-8). D-F classifications of chest pain type (typical angina, atypical angina and non-anginal chest pain) were assigned based on subject interviews (Diamond G A, Forrester J S. Analysis of probability as an aid in the clinical diagnosis of coronary-artery disease. *N Engl J Med.* 1979; 300(24):1350-8), and D-F scores assigned (Chaitman B R, Bourassa M G, Davis K, et al. Angiographic prevalence of high-risk coronary artery disease in patient subsets (CASS). *Circulation.* 1981; 64(2): 360-7). Subjects without chest pain symptoms were classified as non-anginal chest pain. MPIs were performed as clinically indicated, according to local protocols, and interpreted by local readers with access to clinical data but not gene expression or catheterization data. MPIs were defined as positive if ≥1 reversible or fixed defect consistent with obstructive CAD was reported. Indeterminate or intermediate defects were considered negative.

Obstructive CAD and Disease Group Definitions

Patients with obstructive CAD (N=192) were defined prospectively as subjects with ≥1 atherosclerotic plaque in a major coronary artery (≥1.5 mm lumen diameter) causing ≥50% luminal diameter stenosis by QCA; non-obstructive CAD (N=334) had no lesions >50%.

Blood Samples

Prior to coronary angiography, venous blood samples were collected in PAXgene® RNA-preservation tubes. Samples were treated according to manufacturer's instructions, then frozen at −20° C.

RNA Purification and RT-PCR

Automated RNA purification from whole blood samples using the Agencourt RNAdvance system, cDNA synthesis, and RT-PCR were performed as described (Elashoff M R, Wingrove J A, Beineke P, et al. Development of a Blood-based Gene Expression Algorithm for Assessment of Obstructive Coronary Artery Disease in Non-Diabetic Patients, submitted. *Circulation: Cardiovascular Genetics.* 2010). All PCR reactions were run in triplicate and median values used for analysis. Genomic DNA contamination was detected by comparison of expression values for splice-junction spanning and intronic ADORA3 assays normalized to expression values of TFCP2 and HNRPF. The RPS4Y1 assay was run as confirmation of sex for all patients; patients were excluded if there was an apparent mismatch with clinical data. Sample QC metrics and pass-fail criteria were pre-defined and applied prior to evaluation of results as described (Elashoff M R, Wingrove J A, Beineke P, et al. Development of a Blood-based Gene Expression Algorithm for Assessment of Obstructive Coronary Artery Disease in Non-Diabetic Patients, submitted. *Circulation: Cardiovascular Genetics.* 2010).

Statistical Methods

Analyses for Table 24 used SAS Version 9.1 (SAS Institute Inc, Cary, N.C., USA). All other analysis was performed using R Version 2.7 (R Foundation for Statistical Computing, Vienna, Austria). Unless otherwise specified, univariate comparisons for continuous variables were done by t-test and categorical variables by Chi-square test. All reported p-values are two-sided.

Gene Expression Algorithm Score

The algorithm was locked prior to the validation study. Raw algorithm scores were computed from median expression values for the 23 algorithm genes, age and sex as described and used in all statistical analyses; scores were linearly transformed to a 0-40 scale for ease of reporting.

ROC Estimation and AUC Comparison

ROC curves were estimated for the a) gene expression algorithm score, b) the D-F risk score, c) a combined model of algorithm score and D-F risk score, d) MPI, and e) a combined model of algorithm score and MPI. Standard methods (Newson R. Confidence intervals for rank statistics: Somers' D and extensions. *Stata Journal.* 2006; 6:309-334.) were used to estimate the empirical ROC curves and associated AUCs and AUC standard errors. The Z-test was used to test AUCs versus random (AUC=0.50).

Paired AUC comparisons: i) gene expression algorithm score plus D-F risk score vs D-F risk score, and ii) gene expression algorithm score plus MPI vs MPI; were performed by bootstrap. For each comparison, 10,000 bootstrap iterations were run, and the observed AUC difference computed. The median bootstrapped AUC difference was used to estimate the AUC difference, and the p-value estimated using the empirical distribution of bootstrapped AUC differences (i.e. the observed quantile for 0 AUC difference in the empirical distribution).

Logistic Regression

A series of logistic regression models were fit with disease status as the binary dependent variable, and compared using a likelihood ratio test between nested models. Comparisons were: i) gene expression algorithm score plus D-F risk score versus D-F risk score alone; ii) gene expression algorithm score plus MPI versus MPI alone; iii) gene expression algorithm score versus the demographic component of the gene expression algorithm score.

Correlation of Algorithm Score with Maximum Percent Stenosis

The correlation between algorithm score and percent maximum stenosis as continuous variables was assessed by linear regression. Stenosis values were grouped into five increasing categories (no measurable disease, 1-24%, 25-49% in 1 vessel, 1 vessel ≥50%, and >1 vessel ≥50%) and ANOVA was used to test for a linear trend in algorithm score across categories.

Reclassification of Disease Status

Gene expression algorithm score and D-F risk scores were defined as low (0% to <20%), intermediate (≥20%,<50%), and high risk (≥50%) obstructive CAD likelihoods. MPI results were classified as negative (no defect/possible fixed or reversible defect) or positive (fixed or reversible defect). For the D-F risk score analysis, a reclassified subject was defined as i) D-F intermediate risk to low or high algorithm score, ii) D-F high risk to algorithm low risk, or iii) D-F low risk to algorithm high. For the MPI analysis, a reclassified subject included i) MPI positive to low risk based on algorithm score, or ii) MPI negative to high risk based on algorithm score. Net reclassification improvement (NRI) of the gene expression algorithm score (and associated p-value) compared to either the D-F risk score or MPI was computed as described in (Pencina MJ, D'Agostino R B, Sr., D'Agostino R B, Jr., Vasan R S. Evaluating the added predictive ability of a new marker: from area under the ROC curve to reclassification and beyond. *Stat Med.* 2008; 27(2):157-72; discussion 207-12). NRI is a measure of reclassification clinical benefit, and is sensitive to both the fraction and accuracy of reclassification.

NRI Formula

NRI considers as positive reclassifications those patients whose classification moves in the 'correct' direction (disease subjects moving to a higher risk classification and non-disease subjects moving to a lower risk classification). Similarly, NRI considers as negative reclassifications those patients whose classification moves in the incorrect direction (disease subjects moving to a lower risk classification and non-disease subjects moving to a higher risk classification). The NRI formula is then the difference between the fraction of positive reclassifications and the fraction of negative reclassifications.

NRI=(pup,events−pdown,events)−(pup,nonevents−pdown,nonevents)

where:
pup, events=# events moving up/# events
pdown, events=# events moving down# events
pup, nonevents=# nonevents moving up/# nonevents
pdown,nonevents=#nonevents moving down/# nonevents
for significance testing, $z=NRI/(v_e+v_{ne})^{1/2}$ where:
$v_e$=(pup, events+pdown, events)/# events
$v_{ne}$=(pup, nonevents+pdown, nonevents)/#nonevents
(formulas from {Pencina et al., 2008})
Logistic Regression Analyses
D-F Risk Score Model

| Model Term | Odds Ratio | 95% CI | p-value | Model AIC |
|---|---|---|---|---|
| D-F risk score | 1.018 | 1.012 to 1.023 | <.001 | 652.53 |

Gene Expression Algorithm Score+ D-F Risk Score

| Model Term | Odds Ratio | 95% CI | p-value | Model AIC |
|---|---|---|---|---|
| D-F risk score | 1.012 | 1.007 to 1.018 | <.001 | |
| Gene expression algorithm score | 1.64 | 1.37 to 1.96 | <.001 | 622.3 |

MPI Model

| Model Term | Odds Ratio | 95% CI | p-value | Model AIC |
|---|---|---|---|---|
| MPI | 1.52 | 0.88 to 2.67 | .14 | 388.53 |

Gene Expression Algorithm Score+MPI

| Model Term | Odds Ratio | 95% CI | p-value | Model AIC |
|---|---|---|---|---|
| MPI | 1.04 | 0.57 to 1.90 | .90 | |
| Gene expression algorithm score | 1.85 | 1.45 to 2.37 | <.001 | 362.15 |

Net Benefit Analysis

Figure 8:
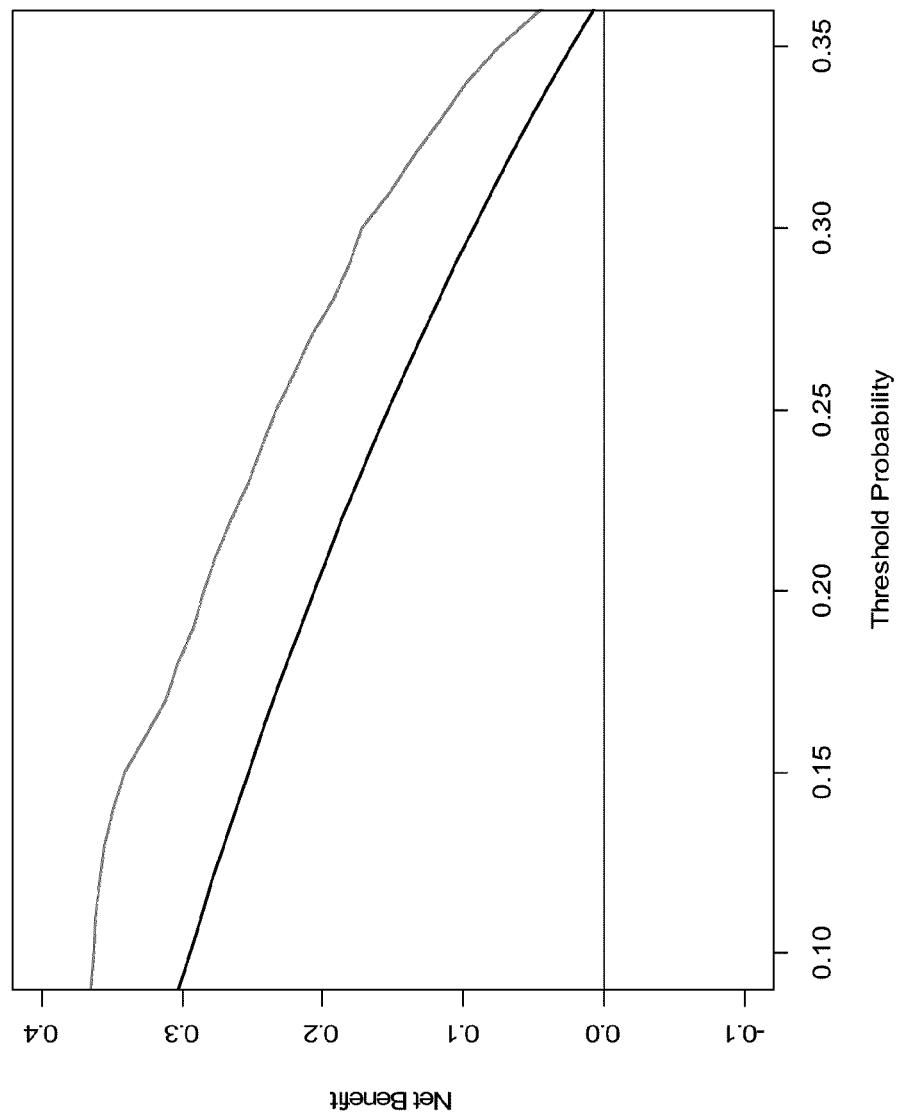
FIG. 8—The net benefit curve for a diagnostic as a function of $p_t$, a threshold probability that represents the tradeoff between false positives and false negatives. The curve quantifies the net benefit to following the decision rule of score>$p_t$=positive, over a range of possible value for $p_t$. The reference lines reflect the net benefit of a) all subjects positive (lower curve) or b) all subjects negative (line at net benefit=0). The net benefit curve for the gene expression algorithm is shown as the top curve, and is greater than either reference line over clinically relevant range for $p_t$.

Vickers {Vickers et al., 2008} defines the net benefit curve for a diagnostic as a function of $p_t$, a threshold probability that represents the tradeoff between false positives and false negatives. The curve quantifies the net benefit to following the decision rule of score>$p_t$=positive, over a range of possible value for $p_t$. The reference lines reflect the net benefit of a) all subjects positive (lower curve in FIG. 8) or b) all subjects negative (line at net benefit=0). The net benefit curve for the gene expression algorithm is the upper curve in FIG. 8, and is greater than either reference line over clinically relevant range for $p_t$.

Full Clinical Model

Methods

To further assess the added value of the gene expression algorithm a 'full' clinical factor model was developed that incorporated the 11 clinical factors that showed univariate significance (p<0.05) between obstructive disease and no obstructive disease patients in the development set. The 11 factors were:

sex
age
chest pain type
race
statin use
aspirin use
anti-platelet use
ACE inhibitor use
systolic blood pressure
hypertension
dyslipidemia A logistic regression model was then fit using disease status as the dependent variable and these 11 factors as predictor variables. A subject's 'full clinical model score' was the subject's predicted value from this model.

Results

Results are reported for the validation set. The AUC of the full clinical model was 0.732, and the AUC for the gene expression algorithm plus the full clinical model was 0.745 (p=0.09). The nested logistic regression comparison of the gene expression algorithm plus the full clinical model versus the full clinical model alone gave a p-value of 0.014.

The NRI of the gene expression algorithm plus the full clinical model versus the full clinical model alone was 10% (p=0.02).

Discussion

The full clinical model evaluated here further supports the concept that the algorithm score adds to known or apparent clinical factors in the PREDICT population. This model suffers from the lack of independent validation, as has been done for the Diamond-Forrester formulation, hence it's role as primary comparator.

Statistical Outlier Assessment

Samples were classified as gene expression outliers based on the following criterion: $\Sigma|g_i-m_i|>27$, where $g_i$ is the expression value for the i'th gene, and $m_i$ is the median expression value for the i'th gene across the development set.

Results

Figure 7:
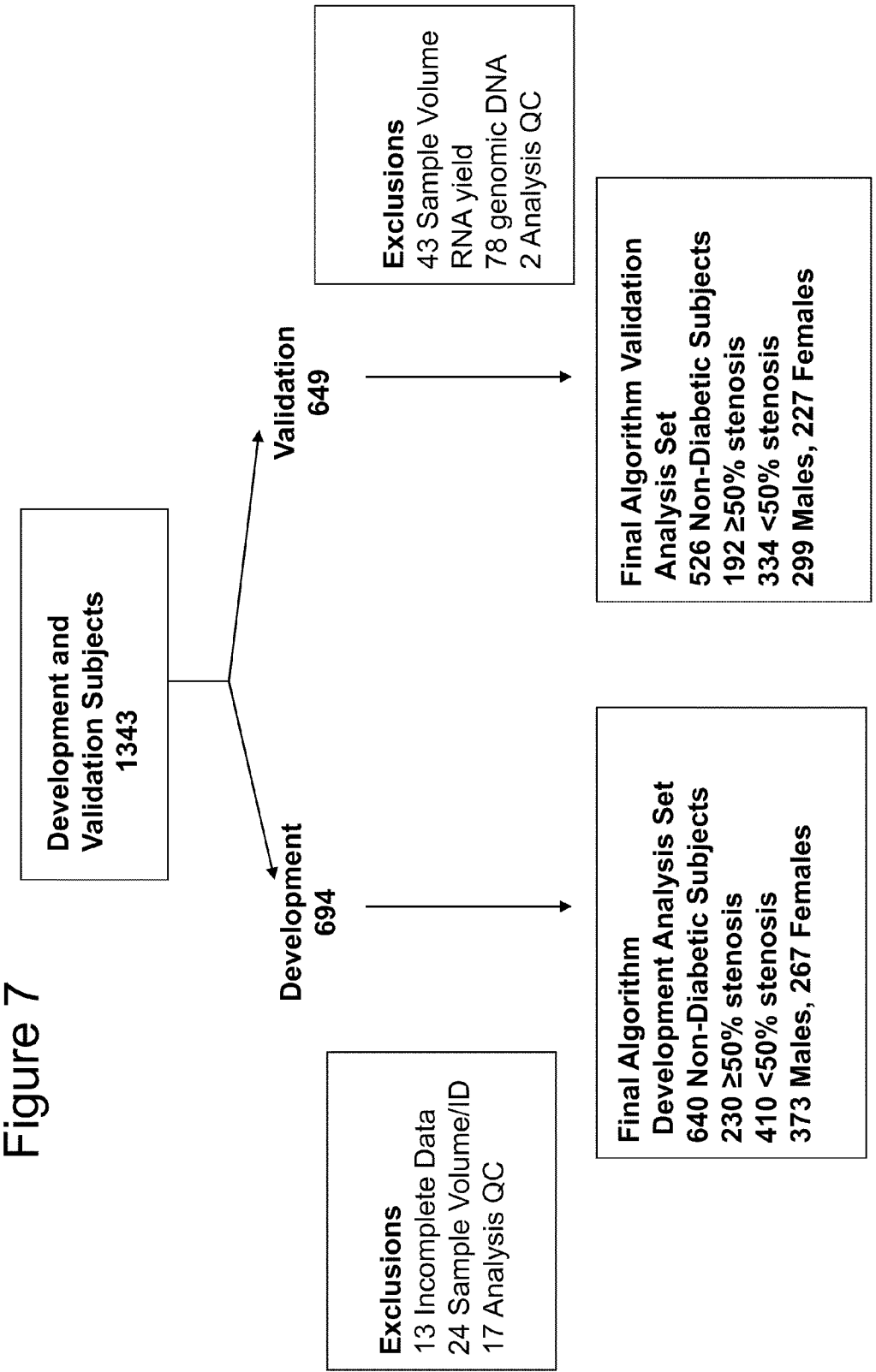
FIG. 7—Allocation of Patients from the PREDICT trial for algorithm development and validation. From a total of 1569 subjects meeting the study inclusion/exclusion criteria 226 were used for gene discovery. The remaining 1343 were divided into independent cohorts for algorithm development (694) and validation (649) as shown; 94% of patients in these cohorts came from the same centers. For algorithm development a total of 640 patient samples were used; 54 were excluded due to incomplete data (Diamond G A, Forrester J S. Analysis of probability as an aid in the clinical diagnosis of coronary-artery disease. *N Engl J Med.* 1979; 300(24):1350-8.), inadequate blood volume (Stangl V, Witzel V, Baumann G, Stangl K. Current diagnostic concepts to detect coronary artery disease in women. *Eur Heart J.* 2008; 29(6):707-17.), sex mismatch between experimental and clinical records (Gibbons R J, Abrams J, Chatterjee K, et al. ACC/AHA 2002 guideline update for the management of patients with chronic stable angina—summary article: a report of the American College of Cardiology/American Heart Association Task Force on practice guidelines (Committee on the Management of Patients With Chronic Stable Angina). *J Am Coll Cardiol.* 2003; 41(1):159-68.), or statistical outlier assessment (Cook N R, Ridker P M. Advances in measuring the effect of individual predictors of cardiovascular risk: the role of reclassification measures. *Ann Intern Med.* 2009; 150(11):795-802). For the validation cohort a total of 123 samples were excluded based on: inadequate blood volume or RNA yield (43), significant contamination with genomic DNA (78), or prespecified statistical outlier assessment (2).

A total of 1343 non-diabetic patients from the PREDICT trial, enrolled between July 2007 and April 2009, were sequentially allocated to independent development (N=694) and validation (N=649) sets. The limitation to non-diabetic patients was based on the significant differences observed in CAD classifier gene sets dependent on diabetic status (Elashoff M R, Wingrove J A, Beineke P, et al. Development of a Blood-based Gene Expression Algorithm for Assessment of Obstructive Coronary Artery Disease in Non-Diabetic Patients, submitted. *Circulation: Cardiovascular Genetics.* 2010). The patient flow, set assignment, and exclusions are shown in FIG. 7. The demographic and clinical characteristics of these sets by disease status, after exclusions, are summarized in Table 24. The clinical characteristics of the development and validation sets were similar. Overall, subjects were 57% male, 37% had obstructive CAD and 26% had no detectable CAD. Significant clinical or demographic variables that were associated with obstructive CAD in both cohorts were increased age, male sex, chest pain type, elevated systolic blood pressure (all p<0.001), hypertension (p=0.001), and white ethnicity (p=0.015).

The gene expression algorithm was developed as described above, with obstructive CAD defined by QCA as ≥50% stenosis in ≥1 major coronary artery. This corresponds approximately to 65-70% stenosis based on clinical angiographic read. The 23 algorithm genes, grouped in the 6 terms, 4 sex-independent and 2 sex-specific, are shown schematically in the figures. The subsequent analyses are for the independent validation set only.

ROC Analysis

Figure 9:
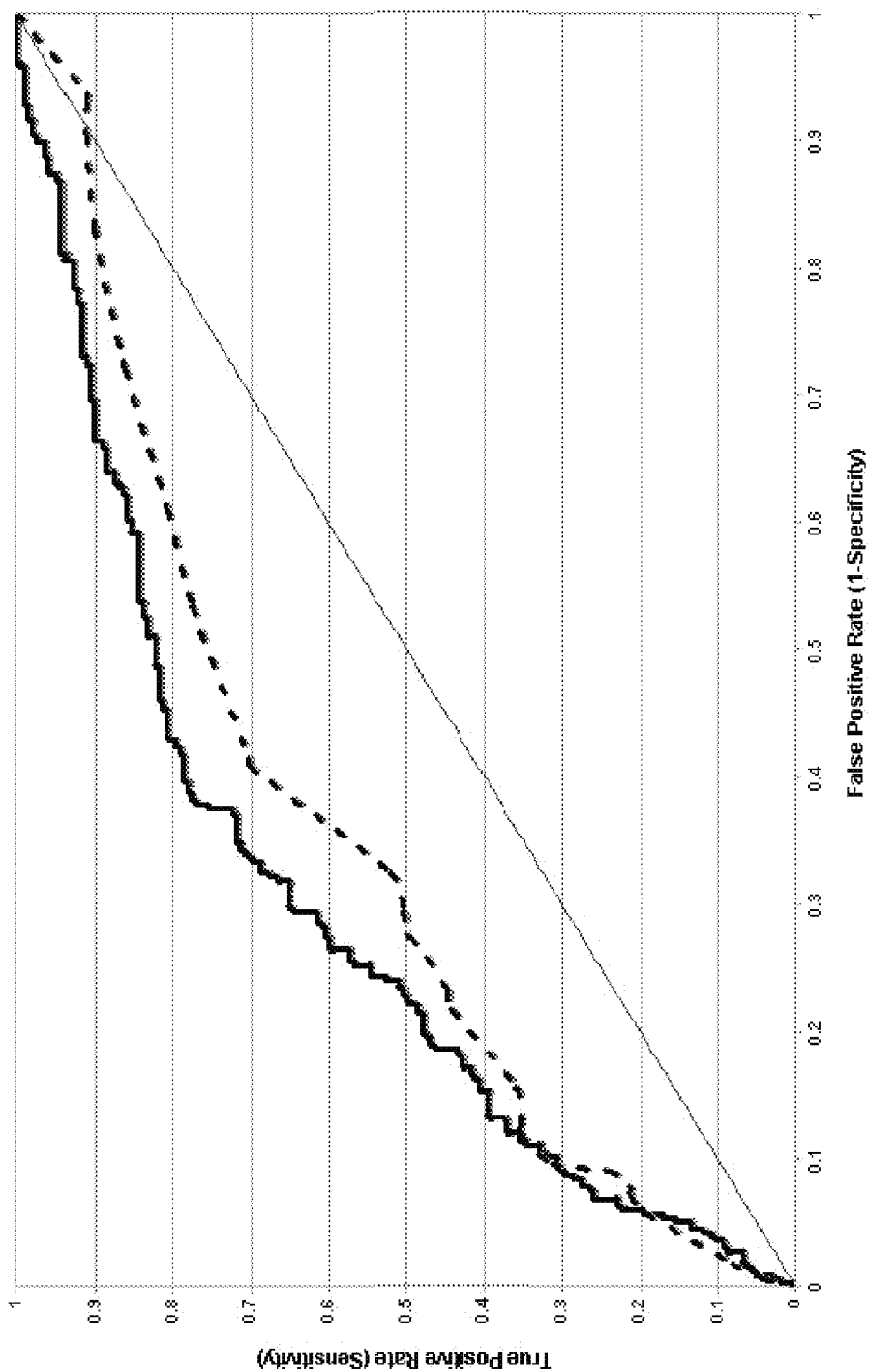
FIG. 9—ROC analysis of Validation Cohort Performance For Algorithm and Clinical Variables. Algorithm performance adds to Clinical Factors by Diamond-Forrester. Comparison of the combination of D-F score and algorithm score (heavy solid line) to D-F score alone (- - -) in ROC analysis is shown. The AUC=0.50 line (light solid line) is shown for reference. A total of 525 of the 526 validation cohort patients had information available to calculate D-F scores. The AUCs for the two ROC curves are 0.721±0.023 and 0.663±0.025, p=0.003.

The prospectively defined primary endpoint was the area under the ROC curve for algorithm score prediction of disease status. The AUC was 0.70±0.02, (p<0.001) with independently significant performance in male (0.66) and female subsets (0.65) (p<0.001 for each). As a clinical comparator, we used the Diamond-Forrester (D-F) risk score, which was developed to quantify likelihood of current CAD and validated in a large cohort (Diamond G A, Forrester J S. Analysis of probability as an aid in the clinical diagnosis of coronary-artery disease. *N Engl J Med.* 1979; 300(24):1350-8.; Chaitman B R, Bourassa M G, Davis K, et al. Angiographic prevalence of high-risk coronary artery disease in patient subsets (CASS). *Circulation.* 1981; 64(2):360-7). ROC analysis showed a higher AUC for the combination of algorithm score and D-F risk score, compared to D-F risk score alone (AUC 0.72 versus 0.66, p=0.003, FIG. 9).

The most prevalent form of non-invasive imaging in PREDICT was MPI. In the validation set 310 patients had clinically-indicated MPIs performed, of which 72% were positive. Comparative ROC analysis showed an increased AUC for the combined algorithm score and MPI versus MPI alone (AUC 0.70 versus 0.54, p<0.001).

Sensitivity, Specificity

Sensitivity and specificity were determined at an algorithm score threshold of 14.75, corresponding to a disease likelihood of 20%, with 33% of patients having scores below this value. At this threshold, the sensitivity was 85% with a specificity of 43%, corresponding to negative and positive predictive values of 83% and 46%, respectively.

Regression Analysis

A series of nested logistic regression models (see methods) were used to assess the independent contribution of the algorithm score and other predictors. Algorithm score added to the D-F risk score (p<0.001), and to MPI (p<0.001), and the algorithm gene expression terms added (p=0.003) to the algorithm demographic terms (see methods).

Association with Disease Severity

Figure 10:
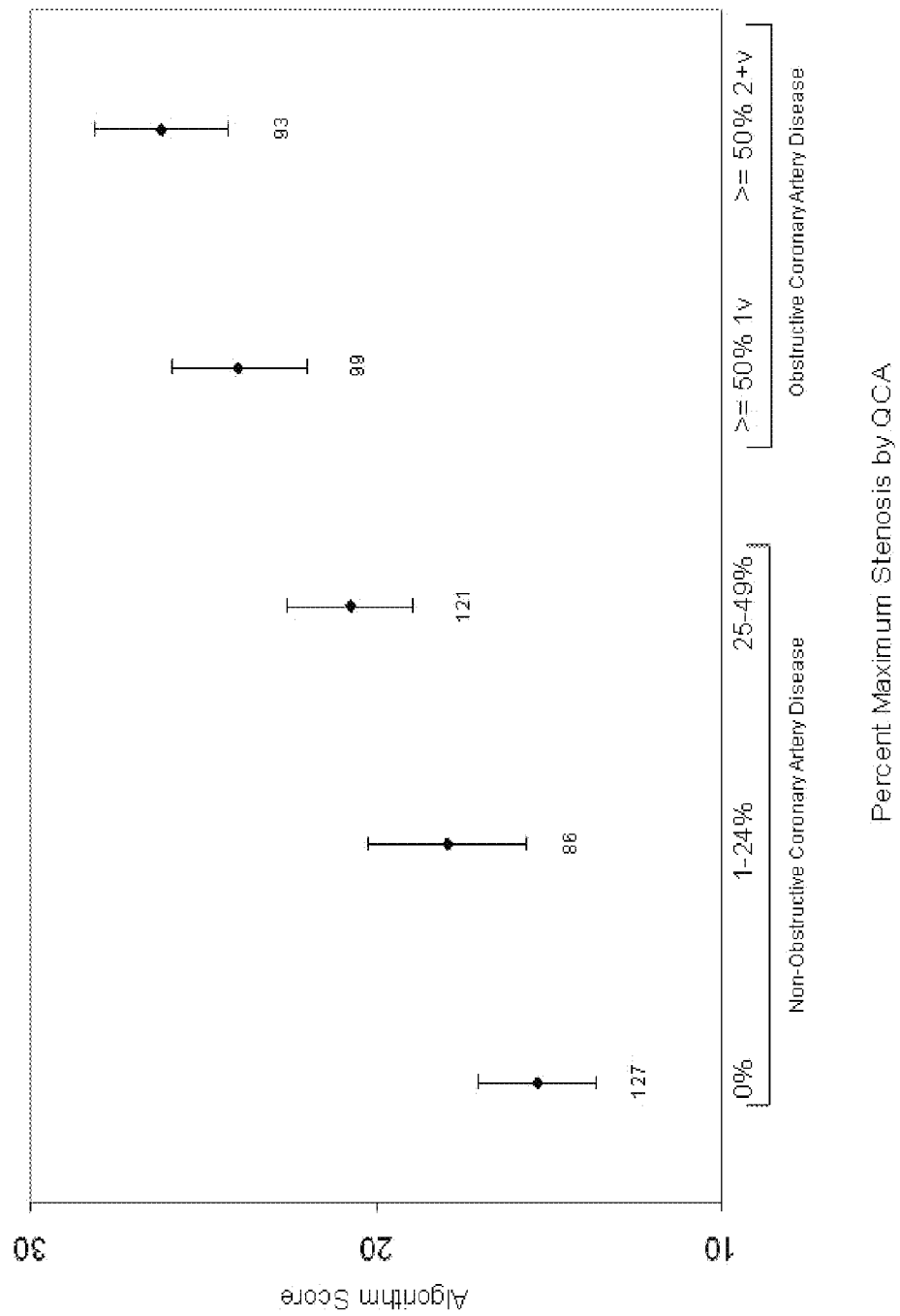
FIG. 10—Dependence of Algorithm Score on % Maximum Stenosis in the Validation Cohort. The extent of disease for each patient was quantified by QCA maximum % stenosis and grouped into 5 categories: no measurable disease, 1-24%, 25-49% in ≥1 vessel, 1 vessel ≥50%, and >1 vessel ≥50%. The average algorithm score for each group is illustrated; error bars correspond to 95% confidence intervals.

The algorithm score was correlated with maximum percent stenosis (R=0.34, p<0.001), and the average algorithm score increased monotonically with increasing percent maximum stenosis (p<0.001, FIG. 10). The average scores for patients with and without obstructive CAD were 25 and 17, respectively.

Reclassification

Reclassification may be a more clinically relevant measure of a predictor's comparative performance than standard measures such as AUC (Cook N R, Ridker P M. Advances in measuring the effect of individual predictors of cardiovascular risk: the role of reclassification measures. *Ann Intern Med.* 2009; 150(11):795-802). Tables 25A and 25B show reclassification results for the gene expression algorithm compared to D-F risk score and MPI. In this study the net reclassification improvement for the gene expression algorithm score compared to the D-F risk score was 20% (p<0.001), and to MPI was 21% (p<0.001).

In subjects with intermediate D-F risk scores, 78% (75/96) of patients were reclassified by the gene expression algorithm. Specifically, for the intermediate D-F group, 22% (21/96) were correctly and 8% (7/96) incorrectly reclassified as low risk; 27% (26/96) were correctly and 22% (21/96) incorrectly reclassified as high risk. An additional 38 D-F low risk subjects (15%) were reclassified as high risk (22 correctly, 16 incorrectly), and 28 D-F high risk subjects (16%) reclassified as low risk (22 correctly, 6 incorrectly). Overall, when reclassification errors occurred, they were to a higher risk category, consistent with the gene expression algorithm having a higher NPV than PPV.

Discussion

This study prospectively validates in non-diabetic patients a non-invasive test for obstructive CAD defined by QCA that is based on gene expression in circulating whole blood cells, age and gender. This study extends our previous work on correlation of gene expression changes in blood with CAD (Wingrove J A, Daniels S E, Sehnert A J, et al. Correlation of Peripheral-Blood Gene Expression With the Extent of Coronary Artery Stenosis. *Circulation: Cardiovascular Genetics.* 2008; 1(1):31-38.) to prospective validation of a classifier for non-diabetic patients with obstructive CAD by ROC analysis (Elashoff M R, Wingrove J A, Beineke P, et al. Development of a Blood-based Gene Expression Algorithm for Assessment of Obstructive Coronary Artery Disease in Non-Diabetic Patients, submitted. *Circulation: Cardiovascular Genetics.* 2010). The test yields a numeric score (0-40) with higher scores corresponding to higher likelihood of obstructive CAD and higher maximum percent stenosis.

It has been suggested that reclassification of patient clinical risk or status, as captured by the NRI, may be a more appropriate measure than comparative ROC analysis for evaluating potential biomarkers (Pencina M J, D'Agostino R B, Sr., D'Agostino R B, Jr., Vasan R S. Evaluating the added predictive ability of a new marker: from area under the ROC curve to reclassification and beyond. *Stat Med.* 2008; 27(2):157-72; discussion 207-12.; Cook N R, Ridker P M. Advances in measuring the effect of individual predictors of cardiovascular risk: the role of reclassification measures. *Ann Intern Med.* 2009; 150(11):795-802). The gene expression algorithm score improves the accuracy of clinical CAD assessment as shown by an NRI of 20% relative to the D-F score. For the most prevalent non-invasive test, MPI, the NRI was 21%, although these results are likely confounded by the referral bias inherent in this angiographically referred population. Overall, independent of MPI result or D-F risk category, increasing gene expression score leads to monotonically increased risk of obstructive CAD (Table 25A,B).

This gene-expression test could have clinical advantages over current non-invasive CAD diagnostic modalities since it requires only a standard venous blood draw, and no need for radiation, intravenous contrast, or physiologic and pharmacologic stressors. One potential clinical benefit of improving non-invasive assessment of CAD is to reduce invasive diagnostic coronary angiograms in patients without obstructive CAD. In the validation cohort, for example, only 37% of patients undergoing invasive angiography had obstructive CAD and the rate was particularly low in women (26%). A similar overall rate of obstructive CAD on angiography for patients without prior known CAD in a very large registry was recently reported, with little sensitivity to the exact definition of obstructive CAD (Patel M R, Peterson E D, Dai D, et al. Low diagnostic yield of elective coronary angiography. *N Engl J Med.* 2010; 362(10):886-95). The gene-expression test described here identified a low-likelihood (<20%) of obstructive CAD in 33% of patients referred for invasive angiography, although the majority of these patients were also at low risk by clinical factor analysis (Table 25A).

CONCLUSIONS

We describe the prospective multi-center validation of a peripheral blood-based gene expression test to determine the likelihood of obstructive CAD in non-diabetic patients as defined by invasive angiography. This test provides additional information to clinical factors and non-invasive imaging as measured by patient CAD status classification. Clinical use of this test may reduce further testing of patients with suspected CAD.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

REFERENCES

1. Diamond G A, Forrester J S. Analysis of probability as an aid in the clinical diagnosis of coronary-artery disease. *N Engl J Med.* 1979; 300(24):1350-1358.
2. Chaitman B R, Bourassa M G, Davis K, Rogers W J, Tyras D H, Berger R, Kennedy J W, Fisher L, Judkins M P, Mock M B, Killip T. Angiographic prevalence of high-risk coronary artery disease in patient subsets (CASS). *Circulation.* 1981; 64(2):360-367.
3. Ridker P M, Buring J E, Rifai N, Cook N R. Development and validation of improved algorithms for the assessment of global cardiovascular risk in women: the Reynolds Risk Score. *Jama.* 2007; 297(6):611-619.
4. Hansson G K, Libby P, Schonbeck U, Yan Z Q. Innate and adaptive immunity in the pathogenesis of atherosclerosis. *Circ Res.* 2002; 91(4):281-291.
5. Libby P, Ridker P M, Maseri A. Inflammation and atherosclerosis. *Circulation.* 2002; 105(9):1135-1143.
6. Sinnaeve P R, Donahue M P, Grass P, Seo D, Vonderscher J, Chibout S D, Kraus W E, Sketch M, Jr., Nelson C, Ginsburg G S, Goldschmidt-Clermont P J, Granger C B. Gene expression patterns in peripheral blood correlate with the extent of coronary artery disease. *PLoS One.* 2009; 4(9):e7037.
7. Wingrove J A, Daniels S E, Sehnert A J, Tingley W, Elashoff M R, Rosenberg S, Buellesfeld L, Grube E, Newby L K, Ginsburg G S, Kraus W E. Correlation of Peripheral-Blood Gene Expression With the Extent of Coronary Artery Stenosis. *Circulation: Cardiovascular Genetics.* 2008; 1(1):31-38.
8. Horne B D, Anderson J L, John J M, Weaver A, Bair T L, Jensen K R, Renlund D G, Muhlestein J B. Which white blood cell subtypes predict increased cardiovascular risk? *J Am Coll Cardiol.* 2005; 45(10):1638-1643.
9. Gibbons R J, Abrams J, Chatterjee K, Daley J, Deedwania P C, Douglas J S, Ferguson T B, Jr., Fihn S D, Fraker T D, Jr., Gardin J M, O'Rourke R A, Pasternak R C, Williams S V. ACC/AHA 2002 guideline update for the management of patients with chronic stable angina—summary article: a report of the American College of Cardiology/American Heart Association Task Force on practice guidelines (Committee on the Management of Patients With Chronic Stable angina). *J Am Coll Cardiol.* 2003; 41(1):159-168.
10. Patel M R, Peterson E D, Dai D, Brennan J M, Redberg R F, Anderson H V, Brindis R G, Douglas P S. Low diagnostic yield of elective coronary angiography. *N Engl J Med.* 2010; 362(10):886-895.
11. Wang L, Hauser E R, Shah S H, Pericak-Vance M A, Haynes C, Crosslin D, Harris M, Nelson S, Hale A B, Granger C B, Haines J L, Jones C J, Crossman D, Seo D, Gregory S G, Kraus W E, Goldschmidt-Clermont P J, Vance J M. Peakwide mapping on chromosome 3q13 identifies the kalirin gene as a novel candidate gene for coronary artery disease. *Am J Hum Genet.* 2007; 80(4):650-663.
12. Rosenberg S, Elashoff M R, Beineke P, Daniels S E, Wingrove J A, Tingley W G, Sager P T, Sehnert A J, Yau Y, Kraus W, Newby L, Schwartz R, Voros S, Ellis S, Tahirkheli N, Waksman R, McPherson J, Lansky A, Schork N, Winn M, Topol E. Multi-Center Validation of the Diagnostic Accuracy of a Blood-based Gene Expression Test for Assessment of Obstructive Coronary Artery Disease in Non-Diabetic Patients. *Submitted;* 2010.
13. Zheng Q, Wang X J. GOEAST: a web-based software toolkit for Gene Ontology enrichment analysis. *Nucleic Acids Res.* 2008; 36(Web Server issue):W358-363.
14. Brunet J P, Tamayo P, Golub T R, Mesirov J P. Metagenes and molecular pattern discovery using matrix factorization. *Proc Natl Acad Sci USA.* 2004; 101(12):4164-4169.
15. Tibshirani R. Regression shrinkage and selection via the lasso. *J. Royal Statistical Society B.* 1996; 58:267-288.

16. Brown P J. *Measurement, Regression, and Calibration.* Oxford, UK: Oxford University Press; 1994.
17. Hamblin M, Chang L, Fan Y, Zhang J, Chen YE. PPARs and the cardiovascular system. *Antioxid Redox Signal.* 2009; 11(6):1415-1452.
18. Ellegren H, Parsch J. The evolution of sex-biased genes and sex-biased gene expression. *Nat Rev Genet.* 2007; 8(9):689-698.
19. Hong M G, Myers A J, Magnusson P K, Prince J A. Transcriptome-wide assessment of human brain and lymphocyte senescence. *PLoS One.* 2008; 3(8):e3024.
20. Rana J S, Boekholdt S M, Ridker P M, Jukema J W, Luben R, Bingham S A, Day N E, Wareham N J, Kastelein J J, Khaw K T. Differential leucocyte count and the risk of future coronary artery disease in healthy men and women: the EPIC-Norfolk Prospective Population Study. *J Intern Med.* 2007; 262(6):678-689.
21. Su A I, Wiltshire T, Batalov S, Lapp H, Ching K A, Block D, Zhang J, Soden R, Hayakawa M, Kreiman G, Cooke M P, Walker J R, Hogenesch J B. A gene atlas of the mouse and human protein-encoding transcriptomes. *Proc Natl Acad Sci USA.* 2004; 101(16):6062-6067.
22. Hasegawa H, Yamada Y, Harasawa H, Tsuji T, Murata K, Sugahara K, Tsuruda K, Masuda M, Takasu N, Kamihira S. Restricted expression of tumor necrosis factor-related apoptosis-inducing ligand receptor 4 in human peripheral blood lymphocytes. *Cell Immunol.* 2004; 231(1-2):1-7.
23. Lim S Y, Raftery M J, Goyette J, Hsu K, Geczy C L. Oxidative modifications of S100 proteins: functional regulation by redox. *J Leukoc Biol.* 2009.
24. Yamasaki S, Ishikawa E, Sakuma M, Hara H, Ogata K, Saito T. Minele is an ITAM-coupled activating receptor that senses damaged cells. *Nat Immunol.* 2008; 9(10): 1179-1188.
25. Teixeira V H, Olaso R, Martin-Magniette M L, Lasbleiz S, Jacq L, Oliveira C R, Hilliquin P, Gut I, Cornelis F, Petit-Teixeira E. Transcriptome analysis describing new immunity and defense genes in peripheral blood mononuclear cells of rheumatoid arthritis patients. *PLoS One.* 2009; 4(8):e6803.
26. Chung C P, Oeser A, Raggi P, Gebretsadik T, Shintani A K, Sokka T, Pincus T, Avalos I, Stein C M. Increased coronary-artery atherosclerosis in rheumatoid arthritis: relationship to disease duration and cardiovascular risk factors. *Arthritis Rheum.* 2005; 52(10):3045-3053.
27. Cruz-Munoz M E, Dong Z, Shi X, Zhang S, Veillette A. Influence of CRACC, a SLAM family receptor coupled to the adaptor EAT-2, on natural killer cell function. *Nat Immunol.* 2009; 10(3):297-305.
28. Kim D K, Kabat J, Borrego F, Sanni T B, You C H, Coligan J E. Human NKG2F is expressed and can associate with DAP12. *Mol Immunol.* 2004; 41(1):53-62.
29. Whitman S C, Rateri D L, Szilvassy S J, Yokoyama W, Daugherty A. Depletion of natural killer cell function decreases atherosclerosis in low-density lipoprotein receptor null mice. *Arterioscler Thromb Vasc Biol.* 2004; 24(6): 1049-1054.
30. Major A S, Fazio S, Linton M F. B-lymphocyte deficiency increases atherosclerosis in LDL receptor-null mice. *Arterioscler Thromb Vasc Biol.* 2002; 22(11):1892-1898.
31. Robertson A K, Hansson G K. T cells in atherogenesis: for better or for worse?*Arterioscler Thromb Vasc Biol.* 2006; 26(11):2421-2432.
32. Park M Y, Hastie T, Tibshirani R. Averaged gene expressions for regression. *Biostatistics.* 2007; 8(2):212-227.

Tables

TABLE 1a

Phase 1 and 11 Microarray Cohorts

| Variable | Phase I - CATHGEN Microarray Cohort | | | Phase II - PREDICT Paired Microarray Cohort | | |
|---|---|---|---|---|---|---|
| | Controls (N = 108) | Cases (N = 87) | p. value | Controls (N = 99) | Cases (N = 99) | p. value |
| Sex (% Male) | 55 (50.9%) | 58 (66.7%) | 0.039 | 75 (75.8%) | 75 (75.8%) | 0.868 |
| Age (yrs) | 55 ± 11 | 63 ± 10 | <.001 | 55 ± 12 | 62 ± 11 | <.001 |
| Caucasian | 56 (51.9%) | 60 (69%) | 0.023 | 85 (85.9%) | 92 (92.9%) | 0.166 |
| BMI | 32 ± 7 | 30 ± 6 | 0.098 | 30 ± 7 | 30 ± 6 | 0.722 |
| Current Smoker | 41 (38%) | 45 (51.7%) | 0.075 | 14 (14.1%) | 25 (25.3%) | 0.074 |
| Systolic BP | 144 ± 22 | 153 ± 25 | 0.007 | 132 ± 17 | 138 ± 18 | 0.009 |
| Diastolic BP | 83 ± 13 | 87 ± 15 | 0.077 | 82 ± 11 | 80 ± 12 | 0.271 |
| Hypertension | 67 (62%) | 65 (74.7%) | 0.084 | 55 (55.6%) | 65 (65.7%) | 0.191 |
| Dyslipidemia | 55 (50.9%) | 58 (66.7%) | 0.039 | 50 (50.5%) | 69 (69.7%) | 0.009 |
| Neutrophil Count | 3.8 ± 1.2 | 4 ± 1.3 | 0.392 | 3.9 ± 1.2 | 4.3 ± 1.5 | 0.037 |
| Lymphocyte Count | 1.8 ± 0.7 | 1.9 ± 0.7 | 0.87 | 2 ± 0.7 | 1.9 ± 0.6 | 0.239 |

TABLE 1b

Phase III and IV Algorithm Development and Validation Cohorts

| Variable | Phase III - PREDICT Algorithm Development Cohort | | | Phase IV - PREDICT Algorithm Validation Cohort | | |
|---|---|---|---|---|---|---|
| | Controls (N = 410) | Cases (N = 230) | p. value | Controls (N = 334) | Cases (N = 192) | p. value |
| Sex (% Male) | 193 (47.1%) | 180 (78.3%) | <.001 | 165 (49.4%) | 134 (69.8%) | <.001 |
| Age (yrs) | 57 ± 12 | 64 ± 11 | <.001 | 57.7 ± 11.7 | 64.7 ± 9.8 | <.001 |
| Caucasian | 347 (84.6%) | 210 (91.3%) | 0.022 | 293 (87.7%) | 181 (94.3%) | 0.015 |
| BMI | 31 ± 8 | 30 ± 6 | 0.348 | 31.3 ± 7.0 | 29.8 ± 5.5 | 0.010 |

TABLE 1b-continued

Phase III and IV Algorithm Development and Validation Cohorts

| Variable | Phase III - PREDICT Algorithm Development Cohort | | | Phase IV - PREDICT Algorithm Validation Cohort | | |
|---|---|---|---|---|---|---|
| | Controls (N = 410) | Cases (N = 230) | p. value | Controls (N = 334) | Cases (N = 192) | p. value |
| Current Smoker | 87 (21.2%) | 45 (19.6%) | 0.693 | 68 (20.4%) | 38 (19.8%) | 0.703 |
| Systolic BP | 133 ± 18 | 138 ± 18 | <.001 | 132 (18.1) | 140 (17.7) | <.001 |
| Diastolic BP | 80 ± 12 | 80 ± 11 | 0.944 | 77.5 (10.9) | 79.2 (11.3) | 0.086 |
| Hypertension | 248 (60.5%) | 167 (72.6%) | 0.003 | 203 (60.8%) | 142 (74.0%) | 0.001 |
| Dyslipidemia | 225 (54.9%) | 170 (73.9%) | <.001 | 208 (62.3%) | 133 (69.3%) | 0.110 |
| Neutrophil Count | 4 ± 1.2 | 4.3 ± 1.4 | 0.054 | 4.0 ± 1.2 | 4.1 ± 1.3 | 0.171 |
| Lymphocyte Count | 2 ± 0.6 | 1.9 ± 0.6 | 0.007 | 1.9 ± 0.6 | 1.9 ± 0.6 | 0.411 |

Microarray cohorts omit subjects whose array data was excluded based on QC analysis (3 CATHGEN, 12 PREDICT)

TABLE 2

Markers Evaluated by RT-PCR in the Algorithm Development Cohort

| Marker Symbol | MicroArray Evidence[1] | Cell-Type[2] | Cluster | Metagene Term | Algorithm Term |
|---|---|---|---|---|---|
| DDX18 | 3 | | 1.1 | | |
| SSRP1 | 3 | | 1.2 | | |
| CCT2 | 3 | 2 | 1.3 | | |
| RPL28 | N | 2 | 1.4 | Norm | 2b |
| XIST | 2 | 1, 4, 5 | 1.5 | | |
| RASSF7 | 3 | | 1.6 | | |
| PKD1 | 3 | | 1.7 | | |
| AGPAT5 | 3 | 2, 7 | 1.8 | | |
| GLS | 3 | | 1.9 | | |
| TMC8 | 3 | | 1.10 | 1 | 3b, 4b |
| RPS4Y1 | 2 | 3 | 1.11 | | |
| KLF12 | 3 | 4 | 1.12 | | |
| LCK | 2, 3 | 3, 4, 8 | 1.13 | | |
| CD3D | 2, 3 | 3, 4, 8 | 1.14 | 1 | 3b, 4b |
| AES | 3 | | 1.15 | | |
| ZAP70 | 3 | 3, 4, 8 | 1.16 | | |
| CD81 | 3 | 7, 8 | 1.17 | | |
| QDPR | 3 | 2, 5 | 1.18 | | |
| FXN | 2 | 2 | 1.19 | | |
| CORO2A | 3 | | 1.20 | | |
| TCEA1 | 3 | 7 | 1.21 | | |
| KMO | 3 | 5, 7 | 2.1 | | |
| TLR7 | 3 | 5 | 2.2 | | |
| RHOC | 3 | | 2.3 | | |
| CX3CR1 | 3 | 6, 8 | 2.4 | | |
| IL11RA | 1, 2 | 3, 4 | 3.1 | | |
| IL7R | 1, 2, 3 | 3, 4, 8 | 3.2 | 3 | |
| FAIM3 | 2, 3 | 3, 4, 7 | 3.3 | | |
| TCF7 | 2, 3 | 3, 4, 8 | 3.4 | 3 | |
| CD79B | 2, 3 | 7 | 3.5 | 2 | 4a |
| SPIB | 2, 3 | 2, 5, 7 | 3.6 | 2 | 4a |
| CD19 | 3 | 5, 7 | 3.7 | | |
| BLK | 3 | 5, 7 | 3.8 | | |
| PI16 | 2 | | 3.9 | | |
| LRRN3 | 3 | 3, 4 | 3.10 | | |
| HNRNPF | N | | 4.1 | Norm | 5b, 6b |
| TFCP2 | N | | 4.2 | Norm | 5b, 6b |
| ACBD5 | 3 | | 4.3 | | |
| DIAPH1 | 3 | | 4.4 | | |
| CD37 | 3 | 7 | 4.5 | | |
| PLAGL2 | 3 | 1 | 4.6 | | |
| SRA1 | 3 | | 5.1 | | |
| CD300A | 2 | 8 | 5.2 | | |
| ELMO2 | 3 | 5, 8 | 5.3 | | |
| CD33 | 2 | 1, 6 | 6.1 | | |
| CSPG2 | 1, 2 | | 6.2 | | |
| CAT | 2 | 2, 5 | 6.3 | | |
| NOD2 | 1, 3 | 1, 6 | 6.4 | | |
| KCNMB1 | 2 | | 6.5 | 5 | |
| TCF7L2 | 3 | 1, 6, 8 | 6.6 | 5 | |
| PDK4 | 3 | | 6.7 | 5 | |
| TBC1D8 | 3 | 1, 5, 6 | 6.8 | | |
| NR4A1 | 3 | 5 | 7.1 | | |
| CDKN1C | 3 | 6, 8 | 7.2 | | |
| C2 | 2 | | 7.3 | | |
| CLC | 2 | 1, 2 | 8.1 | 6 | |
| OLIG2 | 2 | | 8.2 | | |
| ADORA3 | 2 | | 8.3 | 6 | |
| MMD | 1, 2, 3 | 7 | 9.1 | | |
| HIST1H2AE | 1, 3 | 4, 7 | 9.2 | 7 | |
| AMFR | 2 | | 10.1 | | |
| CD34 | N | 2 | 10.2 | | |
| A_24_P128361 (AF289562) | 3 | | 11.1 | 8 | 5a |
| CD248 | 2, 3 | 4 | 11.2 | | |
| KLRC4 | 2 | 4, 8 | 12.1 | 9 | 3a |
| TARP | 2, 3 | 4, 8 | 12.2 | | |
| CCR5 | 2 | 4, 5 | 12.3 | | |
| CD8A | 1 | 3, 4, 8 | 12.4 | | |
| SLAMF7 | 2 | 5, 8 | 12.5 | 9 | 3a |
| KLRC2 | 2 | 3, 4, 8 | 12.6 | | |
| PRSS23 | 2 | 8 | 12.7 | | |
| NCAM1 | N | 8 | 12.8 | | |
| TNFRSF10C | 3 | | 13.1 | 11 | 1b |
| IL8RB | 1, 3 | 1, 6, 8 | 13.2 | 11 | 1b |
| TLR4 | 3 | 1, 6 | 13.3 | 11 | 1b |
| NAMPT | 3 | 1, 5, 6 | 13.4 | | |
| AQP9 | 3 | 1, 6 | 13.5 | 10 | 2c |
| S100A8 | 1, 2, 3 | 1, 5, 6 | 13.6 | 12 | 2a |
| NCF4 | 2, 3 | 1, 6 | 13.7 | 10 | 2c |
| GLT1D1 | 1, 2, 3 | | 13.8 | | |
| TXN | 2, 3 | 2, 5 | 13.9 | | |
| GABARAPL1 | 3 | | 13.10 | | |
| SIRPB2 | 1, 3 | | 13.11 | | |
| TRPM6 | 3 | | 13.12 | | |
| CD93 | 1, 2, 3 | 1, 5, 6 | 13.13 | | |
| ASPRV1 | 3 | | 13.14 | | |
| ALOX5AP | 2, 3 | 5 | 13.15 | | |
| BCL2A1 | 1, 2, 3 | 1, 6, 8 | 13.16 | | |
| F11R | 3 | | 14.1 | | |
| PTAFR | 3 | 1, 6 | 14.2 | | |
| H3F3B | 3 | 7 | 14.3 | | |
| TYROBP | 2, 3 | 1, 6, 8 | 14.4 | | |
| NCF2 | 3 | 1, 5, 6 | 14.5 | | |
| KCNE3 | 2, 3 | 1, 6 | 14.6 | 11 | 1b |
| LAMP2 | 2, 3 | 1 | 14.7 | | |
| PLAUR | 3 | 1, 6 | 14.8 | | |
| CD14 | 1 | 1, 5, 6 | 14.9 | | |
| HK3 | 1, 2 | 1, 6, 8 | 14.10 | | |
| IL18 | 1 | | 14.11 | | |
| RGS18 | 1, 2 | 1, 6 | 15.1 | | |
| BMX | 2, 3 | | 16.1 | | |

TABLE 2-continued

Markers Evaluated by RT-PCR in the Algorithm Development Cohort

| Marker Symbol | MicroArray Evidence[1] | Cell-Type[2] | Cluster | Metagene Term | Algorithm Term |
|---|---|---|---|---|---|
| MMP9 | 2, 3 | | 16.2 | | |
| S100A12 | 1, 2, 3 | 1, 5, 6 | 16.3 | 12 | 2a |
| CLEC4E | 2, 3 | | 16.4 | 12 | 2a |
| CLEC4D | 2, 3 | 1, 6 | 16.5 | | |
| CASP5 | 2, 3 | | 16.6 | 13 | 1a |
| TNFAIP6 | 2, 3 | 1 | 16.7 | 13 | 1a |
| IL18RAP | 1, 3 | 3, 4, 8 | 16.8 | 13 | 1a |
| ARG1 | 2, 3 | | 17.1 | 14 | |
| HP | 1 | 1, 2 | 17.2 | | |
| CBS | 2, 3 | | 17.3 | 14 | |
| AF161365 | 3 | | 17.4 | 15 | 6a |
| ALAS2 | N | | 18.1 | | |

[1]Microarray Evidence: 1 = Wingrove et al, 2 = CATHGEN, 3 = PREDICT, N = normalization Marker
[2]Cell Type: 1 = CD33+, 2 = CD34+, 3 = CD4+, 4 = CD8+, 5 = Dendritic, 6 = CD14+, 7 = CD19+, 8 = CD56+

TABLE 3

Significance of Clinical Variables in CATHGEN Marker discovery set

| Clinical Variable | p-value |
|---|---|
| Diabetes | 0.000560741 |
| Anti Hypertensive Use | 0.012462227 |
| HDL | 0.088459908 |
| Neutrophil Count | 0.129686671 |
| Antidiabetic Use | 0.140870844 |
| LDL | 0.146873756 |
| Total Cholesterol | 0.172382024 |
| WBC Count | 0.189994635 |
| Lipid Lowering Agent Use | 0.200078333 |
| Triglycerides | 0.207728761 |
| Diastolic BP | 0.21703689 |
| Chest Pain | 0.219704278 |
| Monocyte Count | 0.23769698 |
| Platelet Count | 0.238534146 |
| Smoker | 0.257352165 |
| Lymphocyte Count | 0.261169567 |
| Anticoagulant Use | 0.321044006 |
| Anti Inflammatory Use | 0.332101624 |
| Antiplatelet Use | 0.336359859 |
| Statin Use | 0.390097042 |
| Calcium Channel Blocker Use | 0.401676568 |
| Sex | 0.409669446 |
| Postmenopausal | 0.418849343 |
| Alcohol Use | 0.495208348 |
| NSAID Use | 0.536650232 |
| ACE Inhibitor Use | 0.687539195 |
| Vasodilator Use | 0.715979777 |
| Systolic BP | 0.716766737 |
| Antiarrhythmic Use | 0.763504492 |
| Salicylates | 0.805576705 |
| Beta Blocker Use | 0.819779733 |
| Hypertension | 0.834786056 |
| Black | 0.847458733 |
| Age | 0.984504316 |

TABLE 4

RT-PCR Results on CATHGEN cohort Markers

| Marker | Non-Diabetic p | Diabetic p |
|---|---|---|
| KLRG1 | 0.933635139 | 0.000313584 |
| GZMK | 0.176629393 | 0.002075813 |
| CCR5 | 0.524551866 | 0.002796076 |
| RPS4Y1 | 0.641924002 | 0.003924492 |
| TUBB2A | 0.905726045 | 0.012164059 |
| TARP | 0.855579011 | 0.013579949 |
| IGHA1 | 0.427023322 | 0.015653596 |
| CACNA2D2 | 0.579670417 | 0.021884775 |
| ADRB2 | 0.14583996 | 0.035331896 |
| DB097529 | 0.739638806 | 0.037474362 |
| CB853344 | 0.924313185 | 0.042530621 |
| RHOH | 0.914493918 | 0.045421079 |
| GPR114 | 0.113792718 | 0.082926442 |
| RPS27A | 0.127518837 | 0.085484803 |
| CD3E | 0.114159341 | 0.090230797 |
| RELA | 0.800147639 | 0.124184492 |
| HDC | 0.611947115 | 0.124749411 |
| NR1D1 | 0.08855384 | 0.140309177 |
| RRN3 | 0.883475152 | 0.14306721 |
| MARCO | 0.000742446 | 0.162858627 |
| ARL17P1 | 0.009929764 | 0.163503477 |
| POLR2L | 0.110001621 | 0.169570816 |
| RPL10A | 0.372025559 | 0.176554229 |
| TLR5 | 5.31034E−05 | 0.187801635 |
| RPL34 | 0.047258313 | 0.194514225 |
| CARKL | 0.796426726 | 0.197876342 |
| DPM3 | 0.100527185 | 0.210155758 |
| C11orf2 | 0.279960963 | 0.21235462 |
| LIF | 0.319291 | 0.220377076 |
| DHFR | 0.005845519 | 0.227352382 |
| BU540282 | 0.855833364 | 0.253041264 |
| CDC42SE2 | 0.303933209 | 0.27279888 |
| OLIG2 | 9.8531E−05 | 0.291441723 |
| DERL3 | 0.009989003 | 0.311630921 |
| SLK | 0.022499454 | 0.315243668 |
| MBOAT2 | 7.53321E−07 | 0.32533079 |
| ST3GAL1 | 0.555439718 | 0.329090787 |
| FOLR3 | 0.293485861 | 0.330960224 |
| NDUFS7 | 0.510992855 | 0.362739986 |
| SLC29A1 | 0.000196258 | 0.370006714 |
| TCF7 | 0.139201093 | 0.384656786 |
| BQ130147 | 0.005433882 | 0.39124831 |
| SPSB2 | 0.710554126 | 0.392430072 |
| REEP3 | 0.003636115 | 0.39572088 |
| CBS | 8.54923E−05 | 0.414841711 |
| GSTO1 | 0.000439166 | 0.421164955 |
| VSIG4 | 0.03654483 | 0.436274059 |
| OLIG1 | 0.000739337 | 0.438928192 |
| RPL8 | 0.420798397 | 0.441110854 |
| CR609588 | 0.829179104 | 0.44827808 |
| ARG1 | 9.77852E−05 | 0.454989416 |
| JAK2 | 6.14999E−05 | 0.462535965 |
| CLC | 8.43913E−05 | 0.478209075 |
| PAPSS1 | 0.002660178 | 0.497255641 |
| HSPB1 | 0.011649931 | 0.503891496 |
| MPZL1 | 0.069994815 | 0.504344915 |
| BC032451 | 0.015738039 | 0.505628786 |
| BCL2A1 | 2.81815E−05 | 0.50979301 |
| CKLF | 8.76337E−06 | 0.515802792 |
| S100A9 | 1.04727E−07 | 0.5350388 |
| MAPK8IP1 | 0.000267919 | 0.558711324 |
| LOXL2 | 0.153997075 | 0.559866641 |
| GSTP1 | 0.802223179 | 0.622441442 |
| SLC22A1 | 0.000127897 | 0.626928629 |
| HGF | 0.001272015 | 0.63284641 |
| EPOR | 0.919874368 | 0.633466985 |
| ETFB | 0.143878666 | 0.645850919 |
| SSNA1 | 0.103788889 | 0.6470392 |
| IRF2 | 0.018278933 | 0.665824694 |
| ASMTL | 0.311592758 | 0.681691103 |
| ST6GALNAC3 | 0.000812432 | 0.686396961 |
| CSTA | 3.1114E−06 | 0.707081235 |
| SMN1 | 0.473451351 | 0.714837746 |
| REEP5 | 0.000215833 | 0.733733395 |
| FCGBP | 0.074075812 | 0.796385743 |
| S100A12 | 4.72256E−06 | 0.804439181 |
| CAT | 4.59232E−08 | 0.81384176 |
| LOC644246 | 2.85943E−06 | 0.820487985 |
| FRAT1 | 3.39803E−05 | 0.859050707 |
| ATP11B | 6.96563E−05 | 0.882770629 |
| LGALS1 | 0.039299421 | 0.918250705 |

TABLE 4-continued

RT-PCR Results on CATHGEN cohort Markers

| Marker | Non-Diabetic p | Diabetic p |
|---|---|---|
| YWHAZ | 0.023358903 | 0.927846666 |
| MMD | 0.153204886 | 0.941639541 |
| CD33 | 0.101691174 | 0.950753885 |
| CD248 | 0.186672242 | 0.973814259 |
| ADORA3 | 0.000150846 | 0.975200559 |
| TXN | 3.22949E−08 | 0.99228328 |
| LPGAT1 | 1.58563E−06 | 0.995574922 |

TABLE 5

| Marker Symbol |
|---|
| AA303143 |
| AA601031 |
| ABCC2 |
| ABHD2 |
| ABHD5 |
| ABLIM1 |
| ACO2 |
| ACOX1 |
| ACSL1 |
| ACTB |
| ACVR2B |
| ADA |
| ADNP |
| AF034187 |
| AF085968 |
| AF161353 |
| AF471454 |
| AI276257 |
| AIM1L |
| AK021463 |
| AK022268 |
| AK023663 |
| AK024956 |
| AK056689 |
| AK092942 |
| AK098835 |
| AK124192 |
| ALOX12 |
| ALOX5 |
| ALOX5AP |
| ALS2CR13 |
| AMBN |
| AMFR |
| AMICA1 |
| ANXA2 |
| ANXA3 |
| AOAH |
| AP1S2 |
| APBA2 |
| APBB1 |
| APEH |
| APH1A |
| APOBEC3G |
| APRT |
| AQP2 |
| AQP8 |
| ARG1 |
| ARHGAP24 |
| ARHGAP9 |
| ARHGDIA |
| ARID5B |
| ARPC1B |
| ASCL2 |
| ATG3 |
| ATP1B2 |
| ATP5D |
| ATP6V0B |
| ATP7B |
| AW076051 |
| AW579245 |
| AX721252 |

TABLE 5-continued

| Marker Symbol |
|---|
| AY003763 |
| AY062331 |
| A_23_P158868 |
| A_23_P335398 |
| A_23_P348587 |
| A_23_P44053 |
| A_24_P101960 |
| A_24_P144383 |
| A_24_P221375 |
| A_24_P238427 |
| A_24_P384604 |
| A_24_P417996 |
| A_24_P418712 |
| A_24_P745883 |
| A_24_P84408 |
| A_24_P916228 |
| A_24_P929533 |
| A_32_P28158 |
| A_32_P62137 |
| B2M |
| B4GALT5 |
| BACH2 |
| BAGE |
| BAZ1A |
| BBS2 |
| BC024289 |
| BC031973 |
| BC038432 |
| BC043173 |
| BC062739 |
| BC073935 |
| BCL2A1 |
| BCL3 |
| BCL6 |
| BCL7A |
| BG777521 |
| BI024548 |
| BI026064 |
| BM703463 |
| BMX |
| BOP1 |
| BQ365891 |
| BRF1 |
| BRI3 |
| BST1 |
| BTBD14A |
| BTNL8 |
| BU633383 |
| BX110908 |
| BYSL |
| C10orf54 |
| C11orf2 |
| C12orf35 |
| C14orf156 |
| C15orf38 |
| C16orf24 |
| C16orf57 |
| C1orf96 |
| C20orf24 |
| C20orf3 |
| C20orf77 |
| C2orf39 |
| C6orf129 |
| C6orf32 |
| C7orf34 |
| C8orf31 |
| C9orf19 |
| CALM3 |
| CAMKK2 |
| CAPNS1 |
| CASP4 |
| CASP5 |
| CBS |
| CCDC108 |
| CCDC92 |
| CCL3L3 |
| CCPG1 |
| CD200 |

TABLE 5-continued

| Marker Symbol |
|---|
| CD248 |
| CD302 |
| CD3D |
| CD3E |
| CD5 |
| CD58 |
| CD6 |
| CD7 |
| CD79B |
| CD93 |
| CD96 |
| CDKL5 |
| CDKN1A |
| CEACAM4 |
| CEBPB |
| CEBPD |
| CFLAR |
| CFP |
| CHI3L2 |
| CIB3 |
| CKLF |
| CLEC12A |
| CLEC2D |
| CLEC4D |
| CLEC4E |
| CLIC1 |
| CMTM2 |
| CNTNAP2 |
| COL14A1 |
| COMMD6 |
| COP1 |
| COX6B2 |
| COX6C |
| CPD |
| CR2 |
| CR593845 |
| CR610181 |
| CR613361 |
| CR613944 |
| CREB5 |
| CRIP1 |
| CRISPLD2 |
| CSF2RA |
| CSF2RB |
| CSTA |
| CTBP2 |
| CYB5D2 |
| CYP1A2 |
| CYP4F2 |
| CYP4F3 |
| CYP4F8 |
| DCXR |
| DDX11 |
| DDX3Y |
| DEDD2 |
| DEFA4 |
| DEK |
| DENND3 |
| DHRS3 |
| DHRS7B |
| DHRSX |
| DKFZP434B0335 |
| DKFZp434F142 |
| DKFZp547E087 |
| DOCK10 |
| DOCK8 |
| DOK3 |
| DPF3 |
| DPPA5 |
| DRAP1 |
| DUOX2 |
| DUSP13 |
| DUSP3 |
| DYNLT1 |
| ECH1 |
| ECHDC3 |
| EEF2 |
| EIF1AX |
| EIF2AK2 |
| EIF2C4 |
| EIF4B |
| EIF5A |
| EMP3 |
| EMR3 |
| ENST00000337102 |
| ENST00000360102 |
| ENTPD1 |
| ETS1 |
| EXOC6 |
| EXOSC6 |
| F5 |
| FAIM3 |
| FAM108A1 |
| FAM113B |
| FAM26B |
| FAM44A |
| FAU |
| FBXL5 |
| FCAR |
| FCER1A |
| FGD4 |
| FIBP |
| FKBP5 |
| FKBP9 |
| FLJ22662 |
| FLJ40092 |
| FNDC3B |
| FOS |
| FOXJ1 |
| FOXP1 |
| FPR1 |
| FRAT1 |
| FRAT2 |
| FRS2 |
| FRS3 |
| FTH1 |
| FXYD5 |
| FYB |
| GADD45GIP1 |
| GAMT |
| GBP2 |
| GCA |
| GLRX |
| GLT1D1 |
| GLUL |
| GMFG |
| GNB1 |
| GPA33 |
| GPBAR1 |
| GPC1 |
| GPD1 |
| GPR160 |
| GPR172A |
| GPR37L1 |
| GRB10 |
| GSTT1 |
| GTF2I |
| GYG1 |
| H2AFZ |
| H3F3A |
| HAL |
| HAP1 |
| HDAC4 |
| HDDC2 |
| HDGFL1 |
| HEBP2 |
| HIST1H2AC |
| HIST1H2AJ |
| HIST1H2AM |
| HIST1H2BC |
| HIST2H2AC |
| HLA-DRB5 |
| HLA-E |
| HLA-F |
| HMGB2 |
| HOMER3 |

TABLE 5-continued

| Marker Symbol |
|---|
| HOXB7 |
| HSBP1 |
| HSDL2 |
| HSPA1A |
| HSPB1 |
| HTATIP2 |
| ID2 |
| ID3 |
| IFITM4P |
| IGF2R |
| IGHA1 |
| IGHD |
| IGHM |
| IL13RA1 |
| IL18R1 |
| IL1R2 |
| IL23A |
| IL7R |
| IMPA2 |
| IMPDH1 |
| INCA |
| IRAK3 |
| ISG20 |
| ITM2C |
| JDP2 |
| KCNE3 |
| KCNG1 |
| KCNJ15 |
| KIAA0319L |
| KIAA1430 |
| KIAA1833 |
| KLF6 |
| KLHL3 |
| KLRC4 |
| KSR1 |
| LAG3 |
| LAMP2 |
| LAT2 |
| LCK |
| LHPP |
| LILRA2 |
| LILRB3 |
| LILRP2 |
| LIMS2 |
| LIN7A |
| LIN7B |
| LOC137886 |
| LOC149703 |
| LOC150166 |
| LOC153546 |
| LOC220433 |
| LOC389641 |
| LOC401233 |
| LOC401357 |
| LOC439949 |
| LOC440104 |
| LOC440348 |
| LOC440731 |
| LOC497190 |
| LOC644246 |
| LOXL2 |
| LPGAT1 |
| LRRK2 |
| LSM10 |
| LSM7 |
| LST1 |
| LTBP2 |
| LTBP3 |
| LY96 |
| MACF1 |
| MAGED1 |
| MAGED2 |
| MAGEH1 |
| MAK |
| MAN1C1 |
| MAN2A2 |
| MAP1LC3B |
| MAP3K2 |

TABLE 5-continued

| Marker Symbol |
|---|
| MAP3K3 |
| MAP4K4 |
| MAPK14 |
| MAPK8IP1 |
| MAX |
| MBOAT2 |
| MCL1 |
| MEA1 |
| MEGF10 |
| METTL9 |
| MGAM |
| MGC14425 |
| MLKL |
| MLSTD2 |
| MMD |
| MME |
| MMP9 |
| MNDA |
| MORC3 |
| MOSC1 |
| MOSPD2 |
| MPZL1 |
| MRLC2 |
| MRPL42P5 |
| MRPL53 |
| MSRB2 |
| MST150 |
| MUC20 |
| MUM1 |
| MXD1 |
| MYBPH |
| MYC |
| MYH14 |
| MYL6 |
| MYO15B |
| MYO1F |
| MYO1G |
| NAPSA |
| NAPSB |
| NBPF11 |
| NCF4 |
| NDRG2 |
| NDUFB3 |
| NDUFS8 |
| NFATC1 |
| NFIL3 |
| NGFRAP1 |
| NIN |
| NMI |
| NMT2 |
| NOVA1 |
| NPIP |
| NRBF2 |
| NRIP3 |
| NRP1 |
| NRSN2 |
| NUDT16 |
| OLIG1 |
| OR4C15 |
| OR52B2 |
| OSBPL2 |
| OSBPL6 |
| OSTF1 |
| OXNAD1 |
| PACSIN2 |
| PADI4 |
| PARP1 |
| PDCD7 |
| PDE9A |
| PDK2 |
| PDLIM7 |
| PELI1 |
| PFDN5 |
| PFKFB3 |
| PGD |
| PHB |
| PHC2 |
| PHF5A |

TABLE 5-continued

| Marker Symbol |
|---|
| PHGDH |
| PIK3C2B |
| PIM2 |
| PISD |
| PITPNA |
| PLA2G4A |
| PLA2G7 |
| PLAG1 |
| PLD3 |
| PLEKHA1 |
| PLEKHM1 |
| PLXNC1 |
| POLR2A |
| PPP1R12B |
| PPP4R2 |
| PRAP1 |
| PRKAR1A |
| PRKAR1B |
| PRKCA |
| PRKCD |
| PRKDC |
| PRKY |
| PRSS23 |
| PSMB9 |
| PSMD8 |
| PTEN |
| PTOV1 |
| PTPRCAP |
| PTPRK |
| PTPRM |
| PXK |
| PYCARD |
| PYGL |
| QPCT |
| QPRT |
| RAB24 |
| RAB27A |
| RAB31 |
| RAB32 |
| RABGAP1L |
| RABIF |
| RAC1 |
| RAC2 |
| RAI1 |
| RALB |
| RALGDS |
| RARA |
| RASSF2 |
| RBP7 |
| RCC2 |
| REEP5 |
| REPS2 |
| RFWD2 |
| RGS16 |
| RGS2 |
| RHOG |
| RHOH |
| RIMS4 |
| RIT1 |
| RMND5A |
| RNF130 |
| RNF182 |
| RNF24 |
| ROCK2 |
| ROPN1L |
| RPL17 |
| RPL18A |
| RPL22 |
| RPL31 |
| RPL34 |
| RPL36A |
| RPL37 |
| RPL39 |
| RPS10 |
| RPS15 |
| RPS21 |
| RPS27 |
| RPS27A |
| RPS28 |
| RPS4X |
| RPUSD2 |
| RRN3 |
| RTN3 |
| S100A11 |
| S100A12 |
| S100A8 |
| S100A9 |
| S100P |
| SAMSN1 |
| SAP30 |
| SCRN2 |
| SDCBP |
| SEC14L1 |
| SEC22B |
| SEPX1 |
| SERINC1 |
| SERPINB1 |
| SERPINB8 |
| SERPINE1 |
| SF3B14 |
| SFT2D1 |
| SGCE |
| SH2D5 |
| SLA |
| SLC16A3 |
| SLC1A7 |
| SLC22A15 |
| SLC22A4 |
| SLC25A37 |
| SLC2A10 |
| SLC2A14 |
| SLC2A8 |
| SLC35B4 |
| SLC37A3 |
| SLC40A1 |
| SLC45A2 |
| SLC8A1 |
| SLIT3 |
| SMARCD3 |
| SMC1A |
| SMUG1 |
| SOD2 |
| SP100 |
| SPIB |
| SPRR2C |
| SRM |
| SRPK1 |
| SSBP4 |
| ST6GAL1 |
| STAT5A |
| STC1 |
| STK17B |
| STMN1 |
| STX10 |
| STX3 |
| SULT1B1 |
| SYNCRIP |
| SYT15 |
| TAF9B |
| TALDO1 |
| TANK |
| TARP |
| TAX1BP1 |
| TBCD |
| TBL1XR1 |
| TCEAL1 |
| TCF3 |
| TCF7 |
| THBD |
| TLR2 |
| TLR8 |
| TM7SF2 |
| TMEM102 |
| TMEM48 |
| TMEM49 |
| TMEM68 |

TABLE 5-continued

| Marker Symbol |
| --- |
| TMEM86A |
| TNFAIP6 |
| TNFRSF10A |
| TP53I11 |
| TP53TG3 |
| TPST1 |
| TRA@ |
| TRAPPC2L |
| TREM1 |
| TRIB1 |
| TRIM7 |
| TSEN34 |
| TSPAN13 |
| TSPAN16 |
| TSPAN33 |
| TUFM |
| TXN |
| TYROBP |
| U2AF1 |
| UBC |
| UBE2D3 |
| UBE2G2 |
| UBL5 |
| UBQLN1 |
| UCP2 |
| UPF3A |
| URG4 |
| USP11 |
| USP53 |
| USP6 |
| VKORC1 |
| VWCE |
| WDFY3 |
| WDR18 |
| XKR8 |
| XPR1 |
| YOD1 |
| YPEL4 |
| ZBED1 |
| ZCCHC6 |
| ZNF135 |
| ZNF234 |
| ZNF346 |
| ZNF438 |
| ZNF550 |
| ZNF618 |

TABLE 6

| GOID | Ontology | Term | Log odds ratio | p value |
| --- | --- | --- | --- | --- |
| GO:0009987 | bp | cellular process | 0.537 | 5.55E−19 |
| GO:0002376 | bp | immune system process | 1.728 | 9.64E−16 |
| GO:0050896 | bp | response to stimulus | 1.118 | 2.63E−15 |
| GO:0006955 | bp | immune response | 1.796 | 7.62E−12 |
| GO:0008152 | bp | metabolic process | 0.537 | 1.64E−09 |
| GO:0065007 | bp | biological regulation | 0.545 | 2.34E−09 |
| GO:0006952 | bp | defense response | 1.732 | 1.02E−08 |
| GO:0050789 | bp | regulation of biological process | 0.538 | 2.16E−08 |
| GO:0043067 | bp | regulation of programmed cell death | 1.508 | 1.52E−07 |
| GO:0010941 | bp | regulation of cell death | 1.507 | 1.55E−07 |
| GO:0044238 | bp | primary metabolic process | 0.515 | 2.05E−07 |
| GO:0007165 | bp | signal transduction | 0.784 | 2.09E−07 |
| GO:0050794 | bp | regulation of cellular process | 0.520 | 2.50E−07 |
| GO:0042981 | bp | regulation of apoptosis | 1.493 | 3.04E−07 |
| GO:0006950 | bp | response to stress | 1.096 | 3.47E−07 |
| GO:0007154 | bp | cell communication | 0.727 | 5.29E−07 |
| GO:0045321 | bp | leukocyte activation | 2.190 | 6.88E−07 |
| GO:0046649 | bp | lymphocyte activation | 2.307 | 8.27E−07 |
| GO:0044237 | bp | cellular metabolic process | 0.484 | 4.42E−06 |
| GO:0006690 | bp | icosanoid metabolic process | 3.260 | 9.29E−06 |
| GO:0001775 | bp | cell activation | 1.968 | 9.96E−06 |
| GO:0043068 | bp | positive regulation of programmed cell death | 1.746 | 1.47E−05 |
| GO:0048519 | bp | negative regulation of biological process | 0.976 | 1.64E−05 |
| GO:0010942 | bp | positive regulation of cell death | 1.737 | 1.64E−05 |
| GO:0002684 | bp | positive regulation of immune system process | 2.153 | 2.09E−05 |
| GO:0033559 | bp | unsaturated fatty acid metabolic process | 3.120 | 2.23E−05 |
| GO:0019538 | bp | protein metabolic process | 0.702 | 2.24E−05 |
| GO:0002521 | bp | leukocyte differentiation | 2.473 | 3.07E−05 |
| GO:0006414 | bp | translational elongation | 2.100 | 3.49E−05 |
| GO:0043065 | bp | positive regulation of apoptosis | 1.706 | 4.03E−05 |
| GO:0009611 | bp | response to wounding | 1.522 | 4.38E−05 |
| GO:0009605 | bp | response to external stimulus | 1.260 | 4.61E−05 |
| GO:0006954 | bp | inflammatory response | 1.781 | 4.61E−05 |
| GO:0007242 | bp | intracellular signaling cascade | 1.009 | 6.55E−05 |
| GO:0006917 | bp | induction of apoptosis | 1.843 | 7.07E−05 |
| GO:0006691 | bp | leukotriene metabolic process | 3.699 | 7.33E−05 |
| GO:0012502 | bp | induction of programmed cell death | 1.831 | 7.99E−05 |
| GO:0030098 | bp | lymphocyte differentiation | 2.586 | 8.30E−05 |
| GO:0002682 | bp | regulation of immune system process | 1.761 | 9.77E−05 |
| GO:0043449 | bp | cellular alkene metabolic process | 3.603 | 0.00012 |
| GO:0044267 | bp | cellular protein metabolic process | 0.697 | 0.00024 |
| GO:0048523 | bp | negative regulation of cellular process | 0.899 | 0.00046 |
| GO:0042110 | bp | T cell activation | 2.334 | 0.00051 |
| GO:0050776 | bp | regulation of immune response | 2.018 | 0.00057 |
| GO:0055114 | bp | oxidation reduction | 1.237 | 0.00057 |
| GO:0042221 | bp | response to chemical stimulus | 1.082 | 0.00068 |

TABLE 6-continued

| GOID | Ontology | Term | Log odds ratio | p value |
|---|---|---|---|---|
| GO:0043066 | bp | negative regulation of apoptosis | 1.625 | 0.00069 |
| GO:0030097 | bp | hemopoiesis | 1.833 | 0.00078 |
| GO:0043069 | bp | negative regulation of programmed cell death | 1.608 | 0.00082 |
| GO:0060548 | bp | negative regulation of cell death | 1.608 | 0.00082 |
| GO:0002694 | bp | regulation of leukocyte activation | 2.148 | 0.00083 |
| GO:0043170 | bp | macromolecule metabolic process | 0.431 | 0.00101 |
| GO:0050865 | bp | regulation of cell activation | 2.114 | 0.00102 |
| GO:0043412 | bp | macromolecule modification | 0.804 | 0.00130 |
| GO:0051249 | bp | regulation of lymphocyte activation | 2.174 | 0.00139 |
| GO:0048583 | bp | regulation of response to stimulus | 1.526 | 0.00177 |
| GO:0045619 | bp | regulation of lymphocyte differentiation | 2.692 | 0.00245 |
| GO:0051707 | bp | response to other organism | 1.750 | 0.00252 |
| GO:0048534 | bp | hemopoietic or lymphoid organ development | 1.673 | 0.00284 |
| GO:0048518 | bp | positive regulation of biological process | 0.786 | 0.00285 |
| GO:0002696 | bp | positive regulation of leukocyte activation | 2.297 | 0.00301 |
| GO:0050867 | bp | positive regulation of cell activation | 2.297 | 0.00301 |
| GO:0006793 | bp | phosphorus metabolic process | 0.928 | 0.00377 |
| GO:0006796 | bp | phosphate metabolic process | 0.928 | 0.00377 |
| GO:0019221 | bp | cytokine-mediated signaling pathway | 2.387 | 0.00426 |
| GO:0006464 | bp | protein modification process | 0.767 | 0.00461 |
| GO:0045621 | bp | positive regulation of lymphocyte differentiation | 3.046 | 0.00499 |
| GO:0002820 | bp | negative regulation of adaptive immune response | 3.972 | 0.00499 |
| GO:0002823 | bp | negative regulation of adaptive immune response based on somatic recombination of immune receptors built from immunoglobulin superfamily domains | 3.972 | 0.00499 |
| GO:0044260 | bp | cellular macromolecule metabolic process | 0.413 | 0.00561 |
| GO:0045580 | bp | regulation of T cell differentiation | 2.724 | 0.00561 |
| GO:0019370 | bp | leukotriene biosynthetic process | 3.387 | 0.00561 |
| GO:0043450 | bp | alkene biosynthetic process | 3.387 | 0.00561 |
| GO:0002520 | bp | immune system development | 1.580 | 0.00565 |
| GO:0009607 | bp | response to biotic stimulus | 1.477 | 0.00577 |
| GO:0031347 | bp | regulation of defense response | 2.154 | 0.00638 |
| GO:0043101 | bp | purine salvage | 4.650 | 0.00644 |
| GO:0008285 | bp | negative regulation of cell proliferation | 1.413 | 0.00689 |
| GO:0001817 | bp | regulation of cytokine production | 1.908 | 0.00710 |
| GO:0016310 | bp | phosphorylation | 0.971 | 0.00713 |
| GO:0043687 | bp | post-translational protein modification | 0.840 | 0.00713 |
| GO:0042113 | bp | B cell activation | 2.272 | 0.00713 |
| GO:0051251 | bp | positive regulation of lymphocyte activation | 2.258 | 0.00764 |
| GO:0006928 | bp | cellular component movement | 1.253 | 0.00800 |
| GO:0043433 | bp | negative regulation of transcription factor activity | 2.902 | 0.00800 |
| GO:0090048 | bp | negative regulation of transcription regulator activity | 2.902 | 0.00800 |
| GO:0030183 | bp | B cell differentiation | 2.627 | 0.00807 |
| GO:0002252 | bp | immune effector process | 1.981 | 0.00816 |
| GO:0050863 | bp | regulation of T cell activation | 2.098 | 0.00821 |
| GO:0070887 | bp | cellular response to chemical stimulus | 1.562 | 0.00962 |
| GO:0048522 | bp | positive regulation of cellular process | 0.757 | 0.00972 |
| GO:0006412 | bp | translation | 1.220 | 0.01068 |
| GO:0043299 | bp | leukocyte degranulation | 3.650 | 0.01102 |
| GO:0030091 | bp | protein repair | 4.387 | 0.01112 |
| GO:0006916 | bp | anti-apoptosis | 1.656 | 0.01149 |
| GO:0007264 | bp | small GTPase mediated signal transduction | 1.344 | 0.01149 |
| GO:0042127 | bp | regulation of cell proliferation | 1.035 | 0.01275 |
| GO:0007243 | bp | protein kinase cascade | 1.332 | 0.01275 |
| GO:0030217 | bp | T cell differentiation | 2.491 | 0.01322 |
| GO:0031349 | bp | positive regulation of defense response | 2.491 | 0.01322 |
| GO:0006468 | bp | protein amino acid phosphorylation | 0.992 | 0.01363 |
| GO:0002698 | bp | negative regulation of immune effector process | 3.557 | 0.01363 |
| GO:0043392 | bp | negative regulation of DNA binding | 2.709 | 0.01508 |
| GO:0043603 | bp | cellular amide metabolic process | 2.449 | 0.01564 |
| GO:0007166 | bp | cell surface receptor linked signal transduction | 0.727 | 0.01692 |
| GO:0008625 | bp | induction of apoptosis via death domain receptors | 3.470 | 0.01716 |
| GO:0009163 | bp | nucleoside biosynthetic process | 4.165 | 0.01730 |
| GO:0042451 | bp | purine nucleoside biosynthetic process | 4.165 | 0.01730 |
| GO:0042455 | bp | ribonucleoside biosynthetic process | 4.165 | 0.01730 |
| GO:0046129 | bp | purine ribonucleoside biosynthetic process | 4.165 | 0.01730 |
| GO:0033152 | bp | immunoglobulin V(D)J recombination | 4.165 | 0.01730 |
| GO:0051100 | bp | negative regulation of binding | 2.650 | 0.01793 |
| GO:0045582 | bp | positive regulation of T cell differentiation | 2.972 | 0.01808 |

TABLE 6-continued

| GOID | Ontology | Term | Log odds ratio | p value |
|---|---|---|---|---|
| GO:0006959 | bp | humoral immune response | 2.210 | 0.01808 |
| GO:0042035 | bp | regulation of cytokine biosynthetic process | 2.210 | 0.01808 |
| GO:0007162 | bp | negative regulation of cell adhesion | 2.539 | 0.02085 |
| GO:0051591 | bp | response to cAMP | 3.235 | 0.02085 |
| GO:0042036 | bp | negative regulation of cytokine biosynthetic process | 3.235 | 0.02085 |
| GO:0045727 | bp | positive regulation of translation | 3.235 | 0.02085 |
| GO:0051098 | bp | regulation of binding | 1.839 | 0.02085 |
| GO:0051101 | bp | regulation of DNA binding | 1.984 | 0.02085 |
| GO:0032944 | bp | regulation of mononuclear cell proliferation | 2.309 | 0.02085 |
| GO:0050670 | bp | regulation of lymphocyte proliferation | 2.309 | 0.02085 |
| GO:0070663 | bp | regulation of leukocyte proliferation | 2.309 | 0.02085 |
| GO:0045581 | bp | negative regulation of T cell differentiation | 3.972 | 0.02085 |
| GO:0002703 | bp | regulation of leukocyte mediated immunity | 2.513 | 0.02085 |
| GO:0002706 | bp | regulation of lymphocyte mediated immunity | 2.594 | 0.02085 |
| GO:0018193 | bp | peptidyl-amino acid modification | 1.779 | 0.02085 |
| GO:0019321 | bp | pentose metabolic process | 3.972 | 0.02085 |
| GO:0045055 | bp | regulated secretory pathway | 3.235 | 0.02085 |
| GO:0010310 | bp | regulation of hydrogen peroxide metabolic process | 3.972 | 0.02085 |
| GO:0002822 | bp | regulation of adaptive immune response based on somatic recombination of immune receptors built from immunoglobulin superfamily domains | 2.487 | 0.02155 |
| GO:0019748 | bp | secondary metabolic process | 2.079 | 0.02180 |
| GO:0006631 | bp | fatty acid metabolic process | 1.541 | 0.02416 |
| GO:0046688 | bp | response to copper ion | 3.802 | 0.02497 |
| GO:0045628 | bp | regulation of T-helper 2 cell differentiation | 3.802 | 0.02497 |
| GO:0002704 | bp | negative regulation of leukocyte mediated immunity | 3.802 | 0.02497 |
| GO:0002707 | bp | negative regulation of lymphocyte mediated immunity | 3.802 | 0.02497 |
| GO:0046456 | bp | icosanoid biosynthetic process | 2.724 | 0.02597 |
| GO:0010033 | bp | response to organic substance | 1.157 | 0.02601 |
| GO:0080134 | bp | regulation of response to stress | 1.524 | 0.02611 |
| GO:0042180 | bp | cellular ketone metabolic process | 1.016 | 0.02815 |
| GO:0002712 | bp | regulation of B cell mediated immunity | 3.098 | 0.02864 |
| GO:0002889 | bp | regulation of immunoglobulin mediated immune response | 3.098 | 0.02864 |
| GO:0002819 | bp | regulation of adaptive immune response | 2.387 | 0.02920 |
| GO:0008624 | bp | induction of apoptosis by extracellular signals | 2.387 | 0.02920 |
| GO:0050778 | bp | positive regulation of immune response | 1.864 | 0.02930 |
| GO:0030031 | bp | cell projection assembly | 1.998 | 0.02943 |
| GO:0002443 | bp | leukocyte mediated immunity | 1.998 | 0.02943 |
| GO:0051250 | bp | negative regulation of lymphocyte activation | 2.650 | 0.03116 |
| GO:0000122 | bp | negative regulation of transcription from RNA polymerase II promoter | 1.843 | 0.03194 |
| GO:0043094 | bp | cellular metabolic compound salvage | 3.650 | 0.03249 |
| GO:0045749 | bp | negative regulation of S phase of mitotic cell cycle | 3.650 | 0.03249 |
| GO:0050777 | bp | negative regulation of immune response | 3.034 | 0.03249 |
| GO:0080010 | bp | regulation of oxygen and reactive oxygen species metabolic process | 3.650 | 0.03249 |
| GO:0006968 | bp | cellular defense response | 2.131 | 0.03328 |
| GO:0045087 | bp | innate immune response | 1.716 | 0.03404 |
| GO:0006739 | bp | NADP metabolic process | 2.972 | 0.03786 |
| GO:0045088 | bp | regulation of innate immune response | 2.580 | 0.03789 |
| GO:0002697 | bp | regulation of immune effector process | 2.082 | 0.04021 |
| GO:0009617 | bp | response to bacterium | 1.783 | 0.04172 |
| GO:0006636 | bp | unsaturated fatty acid biosynthetic process | 2.546 | 0.04198 |
| GO:0006101 | bp | citrate metabolic process | 3.513 | 0.04231 |
| GO:0002828 | bp | regulation of T-helper 2 type immune response | 3.513 | 0.04231 |
| GO:0046777 | bp | protein amino acid autophosphorylation | 2.066 | 0.04231 |
| GO:0060263 | bp | regulation of respiratory burst | 3.513 | 0.04231 |
| GO:0006082 | bp | organic acid metabolic process | 0.971 | 0.04277 |
| GO:0019752 | bp | carboxylic acid metabolic process | 0.980 | 0.04277 |
| GO:0043436 | bp | oxoacid metabolic process | 0.980 | 0.04277 |
| GO:0009058 | bp | biosynthetic process | 0.423 | 0.04277 |
| GO:0030155 | bp | regulation of cell adhesion | 1.763 | 0.04277 |
| GO:0050870 | bp | positive regulation of T cell activation | 2.034 | 0.04277 |
| GO:0050727 | bp | regulation of inflammatory response | 2.228 | 0.04277 |
| GO:0007265 | bp | Ras protein signal transduction | 1.659 | 0.04277 |
| GO:0010629 | bp | negative regulation of Marker expression | 1.186 | 0.04277 |
| GO:0042742 | bp | defense response to bacterium | 2.018 | 0.04277 |
| GO:0002695 | bp | negative regulation of leukocyte activation | 2.481 | 0.04277 |

TABLE 6-continued

| GOID | Ontology | Term | Log odds ratio | p value |
| --- | --- | --- | --- | --- |
| GO:0009146 | bp | purine nucleoside triphosphate catabolic process | 3.387 | 0.04455 |
| GO:0045620 | bp | negative regulation of lymphocyte differentiation | 3.387 | 0.04455 |
| GO:0050869 | bp | negative regulation of B cell activation | 3.387 | 0.04455 |
| GO:0050853 | bp | B cell receptor signaling pathway | 3.387 | 0.04455 |
| GO:0050864 | bp | regulation of B cell activation | 2.449 | 0.04504 |
| GO:0018212 | bp | peptidyl-tyrosine modification | 2.449 | 0.04504 |
| GO:0048584 | bp | positive regulation of response to stimulus | 1.526 | 0.04534 |
| GO:0019079 | bp | viral genome replication | 2.802 | 0.04639 |
| GO:0009892 | bp | negative regulation of metabolic process | 0.997 | 0.04764 |
| GO:0006357 | bp | regulation of transcription from RNA polymerase II promoter | 0.950 | 0.04827 |
| GO:0010605 | bp | negative regulation of macromolecule metabolic process | 1.020 | 0.04827 |
| GO:0010558 | bp | negative regulation of macromolecule biosynthetic process | 1.106 | 0.04890 |
| GO:0005623 | cc | cell | 0.465 | 2.15E−24 |
| GO:0044464 | cc | cell part | 0.465 | 2.15E−24 |
| GO:0005622 | cc | intracellular | 0.434 | 1.13E−11 |
| GO:0044424 | cc | intracellular part | 0.430 | 1.26E−10 |
| GO:0005737 | cc | cytoplasm | 0.537 | 7.50E−10 |
| GO:0016020 | cc | membrane | 0.551 | 1.18E−08 |
| GO:0005829 | cc | cytosol | 1.207 | 2.30E−07 |
| GO:0005886 | cc | plasma membrane | 0.744 | 7.43E−07 |
| GO:0043229 | cc | intracellular organelle | 0.400 | 1.46E−06 |
| GO:0043226 | cc | organelle | 0.399 | 1.54E−06 |
| GO:0016021 | cc | integral to membrane | 0.583 | 4.13E−06 |
| GO:0044444 | cc | cytoplasmic part | 0.583 | 5.65E−06 |
| GO:0031224 | cc | intrinsic to membrane | 0.559 | 1.09E−05 |
| GO:0044425 | cc | membrane part | 0.516 | 1.44E−05 |
| GO:0022626 | cc | cytosolic ribosome | 2.173 | 0.00034 |
| GO:0044445 | cc | cytosolic part | 1.912 | 0.00040 |
| GO:0043231 | cc | intracellular membrane-bounded organelle | 0.339 | 0.00111 |
| GO:0043227 | cc | membrane-bounded organelle | 0.339 | 0.00116 |
| GO:0033279 | cc | ribosomal subunit | 1.837 | 0.00223 |
| GO:0022627 | cc | cytosolic small ribosomal subunit | 2.532 | 0.00501 |
| GO:0044459 | cc | plasma membrane part | 0.659 | 0.00975 |
| GO:0043228 | cc | non-membrane-bounded organelle | 0.588 | 0.00986 |
| GO:0043232 | cc | intracellular non-membrane-bounded organelle | 0.588 | 0.00986 |
| GO:0044422 | cc | organelle part | 0.435 | 0.01029 |
| GO:0044446 | cc | intracellular organelle part | 0.433 | 0.01149 |
| GO:0005887 | cc | integral to plasma membrane | 0.777 | 0.01842 |
| GO:0031226 | cc | intrinsic to plasma membrane | 0.751 | 0.02085 |
| GO:0032991 | cc | macromolecular complex | 0.516 | 0.02085 |
| GO:0005840 | cc | ribosome | 1.329 | 0.02085 |
| GO:0005634 | cc | nucleus | 0.348 | 0.02601 |
| GO:0016461 | cc | unconventional myosin complex | 3.650 | 0.03249 |
| GO:0015935 | cc | small ribosomal subunit | 1.960 | 0.03404 |
| GO:0005488 | mf | binding | 0.469 | 0.00000 |
| GO:0005515 | mf | protein binding | 0.601 | 0.00000 |
| GO:0003824 | mf | catalytic activity | 0.554 | 0.00000 |
| GO:0003823 | mf | antigen binding | 3.025 | 0.00051 |
| GO:0046983 | mf | protein dimerization activity | 1.350 | 0.00085 |
| GO:0004871 | mf | signal transducer activity | 0.738 | 0.00223 |
| GO:0060089 | mf | molecular transducer activity | 0.738 | 0.00223 |
| GO:0004197 | mf | cysteine-type endopeptidase activity | 2.223 | 0.00456 |
| GO:0016491 | mf | oxidoreductase activity | 1.060 | 0.00553 |
| GO:0004872 | mf | receptor activity | 0.763 | 0.00990 |
| GO:0017070 | mf | U6 snRNA binding | 4.387 | 0.01112 |
| GO:0005536 | mf | glucose binding | 4.387 | 0.01112 |
| GO:0016208 | mf | AMP binding | 3.018 | 0.01639 |
| GO:0030234 | mf | enzyme regulator activity | 0.895 | 0.01730 |
| GO:0008113 | mf | peptide-methionine-(S)-S-oxide reductase activity | 4.165 | 0.01730 |
| GO:0043169 | mf | cation binding | 0.420 | 0.01977 |
| GO:0043167 | mf | ion binding | 0.408 | 0.02085 |
| GO:0046872 | mf | metal ion binding | 0.419 | 0.02085 |
| GO:0005529 | mf | sugar binding | 1.586 | 0.02085 |
| GO:0016165 | mf | lipoxygenase activity | 3.972 | 0.02085 |
| GO:0047485 | mf | protein N-terminus binding | 2.291 | 0.02085 |
| GO:0005509 | mf | calcium ion binding | 0.845 | 0.02138 |
| GO:0030528 | mf | transcription regulator activity | 0.733 | 0.02364 |
| GO:0001848 | mf | complement binding | 3.802 | 0.02497 |

TABLE 6-continued

| GOID | Ontology | Term | Log odds ratio | p value |
|---|---|---|---|---|
| GO:0005527 | mf | macrolide binding | 3.802 | 0.02497 |
| GO:0005528 | mf | FK506 binding | 3.802 | 0.02497 |
| GO:0019838 | mf | growth factor binding | 1.776 | 0.02637 |
| GO:0003735 | mf | structural constituent of ribosome | 1.348 | 0.02664 |
| GO:0019210 | mf | kinase inhibitor activity | 2.412 | 0.02732 |
| GO:0005198 | mf | structural molecule activity | 0.901 | 0.02868 |
| GO:0019899 | mf | enzyme binding | 1.176 | 0.02868 |
| GO:0005351 | mf | sugar:hydrogen symporter activity | 2.387 | 0.02920 |
| GO:0005402 | mf | cation:sugar symporter activity | 2.387 | 0.02920 |
| GO:0004672 | mf | protein kinase activity | 0.930 | 0.02979 |
| GO:0004888 | mf | transmembrane receptor activity | 0.813 | 0.02981 |
| GO:0019207 | mf | kinase regulator activity | 1.853 | 0.03047 |
| GO:0015144 | mf | carbohydrate transmembrane transporter activity | 2.317 | 0.03624 |
| GO:0051119 | mf | sugar transmembrane transporter activity | 2.317 | 0.03624 |
| GO:0003700 | mf | transcription factor activity | 0.928 | 0.04231 |
| GO:0004859 | mf | phospholipase inhibitor activity | 3.513 | 0.04231 |
| GO:0019887 | mf | protein kinase regulator activity | 1.885 | 0.04277 |
| GO:0004896 | mf | cytokine receptor activity | 2.050 | 0.04277 |
| GO:0008603 | mf | cAMP-dependent protein kinase regulator activity | 2.857 | 0.04277 |
| GO:0015295 | mf | solute:hydrogen symporter activity | 2.250 | 0.04277 |
| GO:0055102 | mf | lipase inhibitor activity | 3.387 | 0.04455 |
| GO:0016840 | mf | carbon-nitrogen lyase activity | 3.387 | 0.04455 |
| GO:0016671 | mf | oxidoreductase activity, acting on sulfur group of donors, disulfide as acceptor | 3.387 | 0.04455 |
| GO:0000166 | mf | nucleotide binding | 0.514 | 0.04639 |
| GO:0016787 | mf | hydrolase activity | 0.502 | 0.04653 |

TABLE 7

| Term 1 | Term 2 | Term 3 | Term 4 | Term 5 | Term 6 | Term 7 | Number of Terms | AUC Ridge Regression | AUC Logistic Regression | | AUC Ridge Regression | AUC Logistic Regression |
|---|---|---|---|---|---|---|---|---|---|---|---|---|
| TRUE | TRUE | TRUE | TRUE | TRUE | TRUE | TRUE | 7 | 0.781188 | 0.785011 | | 0.781188 | 0.785011 |
| TRUE | TRUE | TRUE | TRUE | TRUE | TRUE | FALSE | 6 | 0.775592 | 0.779372 | Mean | 0.775346 | 0.778701 |
| TRUE | TRUE | TRUE | TRUE | TRUE | FALSE | TRUE | 6 | 0.764453 | 0.768001 | SD | 0.00497 | 0.004876 |
| TRUE | TRUE | TRUE | TRUE | FALSE | TRUE | TRUE | 6 | 0.778834 | 0.781621 | | | |
| TRUE | TRUE | TRUE | FALSE | TRUE | TRUE | TRUE | 6 | 0.777071 | 0.781157 | | | |
| TRUE | TRUE | FALSE | TRUE | TRUE | TRUE | TRUE | 6 | 0.778887 | 0.782202 | | | |
| TRUE | FALSE | TRUE | TRUE | TRUE | TRUE | TRUE | 6 | 0.776268 | 0.779626 | | | |
| FALSE | TRUE | TRUE | TRUE | TRUE | TRUE | TRUE | 6 | 0.776321 | 0.778929 | | | |

TABLE 8

| Term | AUC Ridge Regression | AUC Logistic Regression |
|---|---|---|
| 7 | 0.781188 | 0.785011 |
| 6 | 0.775346 | 0.778701 |
| 5 | 0.769504 | 0.772411 |
| 4 | 0.763641 | 0.766090 |
| 3 | 0.757567 | 0.759481 |
| 2 | 0.751191 | 0.752634 |
| 1 | 0.744420 | 0.745125 |
| 0 | 0.736732 | 0.736732 |
| DF Model | 0.677495 ± .042437 | |

TABLE 9

| Term 1 | Term 2 | Term 3 | Term 4 | Term 5 | Term 6 | Term 7 | Number of Terms | AUC Ridge Regression | AUC Logistic Regression | | AUC Ridge Regression | AUC Logistic Regression |
|---|---|---|---|---|---|---|---|---|---|---|---|---|
| TRUE | TRUE | TRUE | TRUE | TRUE | FALSE | FALSE | 5 | 0.756671 | 0.761212 | Mean | 0.769504 | 0.772411 |
| TRUE | TRUE | TRUE | TRUE | FALSE | TRUE | FALSE | 5 | 0.772815 | 0.774463 | SD | 0.006329 | 0.006033 |
| TRUE | TRUE | TRUE | FALSE | TRUE | TRUE | FALSE | 5 | 0.771306 | 0.775846 | | | |
| TRUE | TRUE | FALSE | TRUE | TRUE | TRUE | FALSE | 5 | 0.774389 | 0.777155 | | | |
| TRUE | FALSE | TRUE | TRUE | TRUE | TRUE | FALSE | 5 | 0.772889 | 0.775508 | | | |
| FALSE | TRUE | TRUE | TRUE | TRUE | TRUE | FALSE | 5 | 0.770334 | 0.772668 | | | |
| TRUE | TRUE | TRUE | TRUE | FALSE | FALSE | TRUE | 5 | 0.761507 | 0.763841 | | | |
| TRUE | TRUE | TRUE | FALSE | TRUE | FALSE | TRUE | 5 | 0.759744 | 0.764443 | | | |

TABLE 9-continued

| Term 1 | Term 2 | Term 3 | Term 4 | Term 5 | Term 6 | Term 7 | Number of Terms | AUC Ridge Regression | AUC Logistic Regression | | AUC Ridge Regression | AUC Logistic Regression |
|---|---|---|---|---|---|---|---|---|---|---|---|---|
| TRUE | TRUE | FALSE | TRUE | TRUE | FALSE | TRUE | 5 | 0.762542 | 0.765424 | | | |
| TRUE | FALSE | TRUE | TRUE | TRUE | FALSE | TRUE | 5 | 0.760124 | 0.76345 | | | |
| FALSE | TRUE | TRUE | TRUE | TRUE | FALSE | TRUE | 5 | 0.760684 | 0.763249 | | | |
| TRUE | TRUE | TRUE | FALSE | FALSE | TRUE | TRUE | 5 | 0.7748 | 0.77819 | | | |
| TRUE | TRUE | FALSE | TRUE | FALSE | TRUE | TRUE | 5 | 0.776659 | 0.779921 | | | |
| TRUE | FALSE | TRUE | TRUE | FALSE | TRUE | TRUE | 5 | 0.773523 | 0.775466 | | | |
| FALSE | TRUE | TRUE | TRUE | FALSE | TRUE | TRUE | 5 | 0.773766 | 0.775529 | | | |
| TRUE | TRUE | FALSE | FALSE | TRUE | TRUE | TRUE | 5 | 0.775835 | 0.779731 | | | |
| TRUE | FALSE | TRUE | FALSE | TRUE | TRUE | TRUE | 5 | 0.771633 | 0.775613 | | | |
| FALSE | TRUE | TRUE | FALSE | TRUE | TRUE | TRUE | 5 | 0.771084 | 0.773702 | | | |
| TRUE | FALSE | FALSE | TRUE | TRUE | TRUE | TRUE | 5 | 0.775191 | 0.776279 | | | |
| FALSE | TRUE | FALSE | TRUE | TRUE | TRUE | TRUE | 5 | 0.773914 | 0.776289 | | | |
| FALSE | FALSE | TRUE | TRUE | TRUE | TRUE | TRUE | 5 | 0.770165 | 0.772657 | | | |

TABLE 10

| Term 1 | Term 2 | Term 3 | Term 4 | Term 5 | Term 6 | Term 7 | Number of Terms | AUC Ridge Regression | AUC Logistic Regression | | AUC Ridge Regression | AUC Logistic Regression |
|---|---|---|---|---|---|---|---|---|---|---|---|---|
| TRUE | TRUE | TRUE | TRUE | FALSE | FALSE | FALSE | 4 | 0.753409 | 0.755542 | Mean | 0.763641 | 0.76609 |
| TRUE | TRUE | TRUE | FALSE | TRUE | FALSE | FALSE | 4 | 0.752269 | 0.757854 | SD | 0.007095 | 0.00666 |
| TRUE | TRUE | FALSE | TRUE | TRUE | FALSE | FALSE | 4 | 0.75475 | 0.759132 | | | |
| TRUE | FALSE | TRUE | TRUE | TRUE | FALSE | FALSE | 4 | 0.754644 | 0.758973 | | | |
| FALSE | TRUE | TRUE | TRUE | TRUE | FALSE | FALSE | 4 | 0.752923 | 0.755964 | | | |
| TRUE | TRUE | TRUE | FALSE | FALSE | TRUE | FALSE | 4 | 0.769014 | 0.771379 | | | |
| TRUE | TRUE | FALSE | TRUE | FALSE | TRUE | FALSE | 4 | 0.772245 | 0.772932 | | | |
| TRUE | FALSE | TRUE | TRUE | FALSE | TRUE | FALSE | 4 | 0.769289 | 0.770514 | | | |
| FALSE | TRUE | TRUE | TRUE | FALSE | TRUE | FALSE | 4 | 0.76742 | 0.768296 | | | |
| TRUE | TRUE | FALSE | FALSE | TRUE | TRUE | FALSE | 4 | 0.770746 | 0.7748 | | | |
| TRUE | FALSE | TRUE | FALSE | TRUE | TRUE | FALSE | 4 | 0.768423 | 0.771601 | | | |
| FALSE | TRUE | TRUE | FALSE | TRUE | TRUE | FALSE | 4 | 0.765129 | 0.768434 | | | |
| TRUE | FALSE | FALSE | TRUE | TRUE | TRUE | FALSE | 4 | 0.771042 | 0.773185 | | | |
| FALSE | TRUE | FALSE | TRUE | TRUE | TRUE | FALSE | 4 | 0.769152 | 0.771116 | | | |
| FALSE | FALSE | TRUE | TRUE | TRUE | TRUE | FALSE | 4 | 0.767262 | 0.768592 | | | |
| TRUE | TRUE | TRUE | FALSE | FALSE | FALSE | TRUE | 4 | 0.75684 | 0.759332 | | | |
| TRUE | TRUE | FALSE | TRUE | FALSE | FALSE | TRUE | 4 | 0.759744 | 0.762014 | | | |
| TRUE | FALSE | TRUE | TRUE | FALSE | FALSE | TRUE | 4 | 0.75722 | 0.75872 | | | |
| FALSE | TRUE | TRUE | TRUE | FALSE | FALSE | TRUE | 4 | 0.757622 | 0.759311 | | | |
| TRUE | TRUE | FALSE | FALSE | TRUE | FALSE | TRUE | 4 | 0.758392 | 0.76194 | | | |
| TRUE | FALSE | TRUE | FALSE | TRUE | FALSE | TRUE | 4 | 0.754232 | 0.757463 | | | |
| FALSE | TRUE | TRUE | FALSE | TRUE | FALSE | TRUE | 4 | 0.754739 | 0.758625 | | | |
| TRUE | FALSE | FALSE | TRUE | TRUE | FALSE | TRUE | 4 | 0.757696 | 0.76081 | | | |
| FALSE | TRUE | FALSE | TRUE | TRUE | FALSE | TRUE | 4 | 0.759448 | 0.760821 | | | |
| FALSE | FALSE | TRUE | TRUE | TRUE | FALSE | TRUE | 4 | 0.756228 | 0.757865 | | | |
| TRUE | TRUE | FALSE | FALSE | FALSE | TRUE | TRUE | 4 | 0.773956 | 0.777345 | | | |
| TRUE | FALSE | TRUE | FALSE | FALSE | TRUE | TRUE | 4 | 0.768824 | 0.771253 | | | |
| FALSE | TRUE | TRUE | FALSE | FALSE | TRUE | TRUE | 4 | 0.768391 | 0.770482 | | | |
| TRUE | FALSE | FALSE | TRUE | FALSE | TRUE | TRUE | 4 | 0.77252 | 0.773998 | | | |
| FALSE | TRUE | FALSE | TRUE | FALSE | TRUE | TRUE | 4 | 0.772277 | 0.77365 | | | |
| FALSE | FALSE | TRUE | TRUE | FALSE | TRUE | TRUE | 4 | 0.767536 | 0.769299 | | | |
| TRUE | FALSE | FALSE | FALSE | TRUE | TRUE | TRUE | 4 | 0.770376 | 0.77328 | | | |
| FALSE | TRUE | FALSE | FALSE | TRUE | TRUE | TRUE | 4 | 0.769743 | 0.77196 | | | |
| FALSE | FALSE | TRUE | FALSE | TRUE | TRUE | TRUE | 4 | 0.764875 | 0.767167 | | | |
| FALSE | FALSE | FALSE | TRUE | TRUE | TRUE | TRUE | 4 | 0.769057 | 0.769489 | | | |

TABLE 11

| Term 1 | Term 2 | Term 3 | Term 4 | Term 5 | Term 6 | Term 7 | Number of Terms | AUC Ridge Regression | AUC Logistic Regression | | AUC Ridge Regression | AUC Logistic Regression |
|---|---|---|---|---|---|---|---|---|---|---|---|---|
| TRUE | TRUE | TRUE | FALSE | FALSE | FALSE | FALSE | 3 | 0.749217 | 0.752026 | Mean | 0.757567 | 0.759481 |
| TRUE | TRUE | FALSE | TRUE | FALSE | FALSE | FALSE | 3 | 0.751783 | 0.754158 | SD | 0.007376 | 0.006937 |
| TRUE | FALSE | TRUE | TRUE | FALSE | FALSE | FALSE | 3 | 0.750474 | 0.752448 | | | |
| FALSE | TRUE | TRUE | TRUE | FALSE | FALSE | FALSE | 3 | 0.749492 | 0.749734 | | | |
| TRUE | TRUE | FALSE | FALSE | TRUE | FALSE | FALSE | 3 | 0.751223 | 0.755732 | | | |
| TRUE | FALSE | TRUE | FALSE | TRUE | FALSE | FALSE | 3 | 0.748985 | 0.752913 | | | |

TABLE 11-continued

| Term 1 | Term 2 | Term 3 | Term 4 | Term 5 | Term 6 | Term 7 | Number of Terms | AUC Ridge Regression | AUC Logistic Regression | | AUC Ridge Regression | AUC Logistic Regression |
|---|---|---|---|---|---|---|---|---|---|---|---|---|
| FALSE | TRUE | TRUE | FALSE | TRUE | FALSE | FALSE | 3 | 0.746725 | 0.750442 | | | |
| TRUE | FALSE | FALSE | TRUE | TRUE | FALSE | FALSE | 3 | 0.751804 | 0.755362 | | | |
| FALSE | TRUE | FALSE | TRUE | TRUE | FALSE | FALSE | 3 | 0.750864 | 0.753388 | | | |
| FALSE | FALSE | TRUE | TRUE | TRUE | FALSE | FALSE | 3 | 0.74946 | 0.752047 | | | |
| TRUE | TRUE | FALSE | FALSE | FALSE | TRUE | FALSE | 3 | 0.76856 | 0.770535 | | | |
| TRUE | FALSE | TRUE | FALSE | FALSE | TRUE | FALSE | 3 | 0.765245 | 0.766628 | | | |
| FALSE | TRUE | TRUE | FALSE | FALSE | TRUE | FALSE | 3 | 0.762711 | 0.764052 | | | |
| TRUE | FALSE | FALSE | TRUE | FALSE | TRUE | FALSE | 3 | 0.767916 | 0.768687 | | | |
| FALSE | TRUE | FALSE | TRUE | FALSE | TRUE | FALSE | 3 | 0.766618 | 0.766702 | | | |
| FALSE | FALSE | TRUE | TRUE | FALSE | TRUE | FALSE | 3 | 0.763767 | 0.764432 | | | |
| TRUE | FALSE | FALSE | FALSE | TRUE | TRUE | FALSE | 3 | 0.767388 | 0.770134 | | | |
| FALSE | TRUE | FALSE | FALSE | TRUE | TRUE | FALSE | 3 | 0.76458 | 0.766734 | | | |
| FALSE | FALSE | TRUE | FALSE | TRUE | TRUE | FALSE | 3 | 0.760884 | 0.762669 | | | |
| FALSE | FALSE | FALSE | TRUE | TRUE | TRUE | FALSE | 3 | 0.766005 | 0.766618 | | | |
| TRUE | TRUE | FALSE | FALSE | FALSE | FALSE | TRUE | 3 | 0.756133 | 0.758456 | | | |
| TRUE | FALSE | TRUE | FALSE | FALSE | FALSE | TRUE | 3 | 0.751213 | 0.752891 | | | |
| FALSE | TRUE | TRUE | FALSE | FALSE | FALSE | TRUE | 3 | 0.751899 | 0.753747 | | | |
| TRUE | FALSE | FALSE | TRUE | FALSE | FALSE | TRUE | 3 | 0.755404 | 0.75702 | | | |
| FALSE | TRUE | FALSE | TRUE | FALSE | FALSE | TRUE | 3 | 0.756904 | 0.758213 | | | |
| FALSE | FALSE | TRUE | TRUE | FALSE | FALSE | TRUE | 3 | 0.753166 | 0.753082 | | | |
| TRUE | FALSE | FALSE | FALSE | TRUE | FALSE | TRUE | 3 | 0.75268 | 0.756143 | | | |
| FALSE | TRUE | FALSE | FALSE | TRUE | FALSE | TRUE | 3 | 0.753155 | 0.755996 | | | |
| FALSE | FALSE | TRUE | FALSE | TRUE | FALSE | TRUE | 3 | 0.748932 | 0.750484 | | | |
| FALSE | FALSE | FALSE | TRUE | TRUE | FALSE | TRUE | 3 | 0.753103 | 0.755119 | | | |
| TRUE | FALSE | FALSE | FALSE | FALSE | TRUE | TRUE | 3 | 0.767969 | 0.77063 | | | |
| FALSE | TRUE | FALSE | FALSE | FALSE | TRUE | TRUE | 3 | 0.767832 | 0.76969 | | | |
| FALSE | FALSE | TRUE | FALSE | FALSE | TRUE | TRUE | 3 | 0.762099 | 0.763112 | | | |
| FALSE | FALSE | FALSE | TRUE | FALSE | TRUE | TRUE | 3 | 0.766544 | 0.76723 | | | |
| FALSE | FALSE | FALSE | FALSE | TRUE | TRUE | TRUE | 3 | 0.764105 | 0.76458 | | | |

TABLE 12

| Term 1 | Term 2 | Term 3 | Term 4 | Term 5 | Term 6 | Term 7 | Number of Terms | AUC Ridge Regression | AUC Logistic Regression | | AUC Ridge Regression | AUC Logistic Regression |
|---|---|---|---|---|---|---|---|---|---|---|---|---|
| TRUE | TRUE | FALSE | FALSE | FALSE | FALSE | FALSE | 2 | 0.748341 | 0.750526 | Mean | 0.751191 | 0.752634 |
| TRUE | FALSE | TRUE | FALSE | FALSE | FALSE | FALSE | 2 | 0.745247 | 0.747485 | SD | 0.007213 | 0.006971 |
| FALSE | TRUE | TRUE | FALSE | FALSE | FALSE | FALSE | 2 | 0.743589 | 0.744508 | | | |
| TRUE | FALSE | FALSE | TRUE | FALSE | FALSE | FALSE | 2 | 0.747945 | 0.749254 | | | |
| FALSE | TRUE | FALSE | TRUE | FALSE | FALSE | FALSE | 2 | 0.748203 | 0.748151 | | | |
| FALSE | FALSE | TRUE | TRUE | FALSE | FALSE | FALSE | 2 | 0.745722 | 0.745268 | | | |
| TRUE | FALSE | FALSE | FALSE | TRUE | FALSE | FALSE | 2 | 0.74682 | 0.75117 | | | |
| FALSE | TRUE | FALSE | FALSE | TRUE | FALSE | FALSE | 2 | 0.745522 | 0.748225 | | | |
| FALSE | FALSE | TRUE | FALSE | TRUE | FALSE | FALSE | 2 | 0.742333 | 0.74455 | | | |
| FALSE | FALSE | FALSE | TRUE | TRUE | FALSE | FALSE | 2 | 0.746968 | 0.749618 | | | |
| TRUE | FALSE | FALSE | FALSE | FALSE | TRUE | FALSE | 2 | 0.764516 | 0.765794 | | | |
| FALSE | TRUE | FALSE | FALSE | FALSE | TRUE | FALSE | 2 | 0.762225 | 0.762563 | | | |
| FALSE | FALSE | TRUE | FALSE | FALSE | TRUE | FALSE | 2 | 0.75759 | 0.758561 | | | |
| FALSE | FALSE | FALSE | TRUE | FALSE | TRUE | FALSE | 2 | 0.762415 | 0.762985 | | | |
| FALSE | FALSE | FALSE | FALSE | TRUE | TRUE | FALSE | 2 | 0.760145 | 0.761486 | | | |
| TRUE | FALSE | FALSE | FALSE | FALSE | FALSE | TRUE | 2 | 0.750526 | 0.752057 | | | |
| FALSE | TRUE | FALSE | FALSE | FALSE | FALSE | TRUE | 2 | 0.751012 | 0.752701 | | | |
| FALSE | FALSE | TRUE | FALSE | FALSE | FALSE | TRUE | 2 | 0.74568 | 0.746092 | | | |
| FALSE | FALSE | FALSE | TRUE | FALSE | FALSE | TRUE | 2 | 0.750811 | 0.751888 | | | |
| FALSE | FALSE | FALSE | FALSE | TRUE | FALSE | TRUE | 2 | 0.747739 | 0.749608 | | | |
| FALSE | FALSE | FALSE | FALSE | FALSE | TRUE | TRUE | 2 | 0.761655 | 0.762827 | | | |

TABLE 13

| Term 1 | Term 2 | Term 3 | Term 4 | Term 5 | Term 6 | Term 7 | Number of Terms | AUC Ridge Regression | AUC Logistic Regression | | AUC Ridge Regression | AUC Logistic Regression |
|---|---|---|---|---|---|---|---|---|---|---|---|---|
| TRUE | FALSE | FALSE | FALSE | FALSE | FALSE | FALSE | 1 | 0.742993 | 0.744978 | Mean | 0.74442 | 0.745125 |
| FALSE | TRUE | FALSE | FALSE | FALSE | FALSE | FALSE | 1 | 0.742555 | 0.743273 | SD | 0.006498 | 0.006455 |
| FALSE | FALSE | TRUE | FALSE | FALSE | FALSE | FALSE | 1 | 0.738732 | 0.738437 | | | |
| FALSE | FALSE | FALSE | TRUE | FALSE | FALSE | FALSE | 1 | 0.743288 | 0.743288 | | | |

TABLE 13-continued

| Term 1 | Term 2 | Term 3 | Term 4 | Term 5 | Term 6 | Term 7 | Number of Terms | AUC Ridge Regression | AUC Logistic Regression | AUC Ridge Regression | AUC Logistic Regression |
|---|---|---|---|---|---|---|---|---|---|---|---|
| FALSE | FALSE | FALSE | FALSE | TRUE | FALSE | FALSE | 1 | 0.740939 | 0.742903 | | |
| FALSE | FALSE | FALSE | FALSE | FALSE | TRUE | FALSE | 1 | 0.757125 | 0.757442 | | |
| FALSE | FALSE | FALSE | FALSE | FALSE | FALSE | TRUE | 1 | 0.74531 | 0.745553 | | |

TABLE 14

| Term 1 | Term 2 | Term 3 | Term 4 | Term 5 | Term 6 | Term 7 | Number of Terms | AUC Ridge Regression | AUC Logistic Regression | AUC Ridge Regression | AUC Logistic Regression |
|---|---|---|---|---|---|---|---|---|---|---|---|
| FALSE | FALSE | FALSE | FALSE | FALSE | FALSE | FALSE | 0 | 0.736732 | 0.736732 | 0.736732 | 0.736732 |

TABLE 15

| Algorithm Marker | Substitute Marker | Correlation | AUC Ridge Regression | AUC Logistic egression | RefSeq Algorithm Marker | RefSeq Substitute Marker |
|---|---|---|---|---|---|---|
| S100A12 | MMP9 | 0.77 | 0.781 | 0.784 | NM_005621 | NM_004994 |
| CLEC4E | ALOX5AP | 0.74 | 0.780 | 0.783 | NM_014358 | NM_001629 |
| S100A8 | NAMPT | 0.90 | 0.781 | 0.786 | NM_002964 | NM_005746 |
| CASP5 | H3F3B | 0.63 | 0.783 | 0.787 | NM_001136112 | NM_005324 |
| IL18RAP | TXN | 0.52 | 0.774 | 0.778 | NM_003853 | NM_003329 |
| TNFAIP6 | PLAUR | 0.66 | 0.779 | 0.783 | NM_007115 | NM_001005376 |
| AQP9 | GLT1D1 | 0.93 | 0.781 | 0.785 | NM_020980 | NM_144669 |
| NCF4 | NCF2 | 0.91 | 0.780 | 0.784 | NM_000631 | NM_000433 |
| CD3D | LCK | 0.95 | 0.779 | 0.784 | NM_000732 | NM_001042771 |
| TMC8 | CCT2 | 0.85 | 0.781 | 0.785 | NM_152468 | NM_006431 |
| CD79B | CD19 | 0.95 | 0.796 | 0.809 | NM_000626 | NM_001770 |
| SPIB | BLK | 0.89 | 0.780 | 0.784 | NM_003121 | NM_001715 |
| HNRPF | ACBD5 | 0.88 | 0.779 | 0.783 | NM_001098204 | NM_001042473 |
| TFCP2 | DDX18 | 0.88 | 0.781 | 0.786 | NM_005653 | NM_006773 |
| RPL28 | SSRP1 | 0.91 | 0.782 | 0.786 | NM_000991 | NM_003146 |
| AF161365 | AF161365 | 1.00 | 0.781 | 0.785 | AF161365 | AF161365 |
| AF289562 | CD248 | 0.53 | 0.779 | 0.783 | AF289562 | NM_020404 |
| SLAMF7 | CX3CR1 | 0.83 | 0.778 | 0.783 | NM_021181 | NM_001171171 |
| KLRC4 | CD8A | 0.79 | 0.794 | 0.805 | NM_013431 | NM_001145873 |
| IL8RB | BCL2A1 | 0.82 | 0.780 | 0.785 | NM_001557 | NM_001114735 |
| TNFRSF10C | PTAFR | 0.84 | 0.781 | 0.785 | NM_003841 | NM_000952 |
| KCNE3 | LAMP2 | 0.90 | 0.781 | 0.784 | NM_005472 | NM_001122606 |
| TLR4 | TYROBP | 0.84 | 0.780 | 0.783 | NM_138554 | NM_003332 |
| | Mean | 0.82 | 0.781 | 0.786 | | |
| | SD | 0.13 | 0.005 | 0.007 | | |

Markers are replaced with the most highly correlated non-algorithm marker in the PCR data set, while ensuring that the set of Substitute Markers has no duplicates.

TABLE 16

| Genomic Terms | AUC Ridge Regression | AUC Logistic Regression |
|---|---|---|
| Full Model | 0.781 | 0.785 |
| 1 Marker Replaced | 0.781 ± .009 | 0.786 ± .014 |
| 5 Markers Replaced | 0.781 ± .014 | 0.788 ± .021 |
| 10 Markers Replaced | 0.778 ± .015 | 0.785 ± .020 |
| 15 Markers Replaced | 0.779 ± .014 | 0.787 ± .020 |

TABLE 16-continued

| Genomic Terms | AUC Ridge Regression | AUC Logistic Regression |
|---|---|---|
| 20 Markers Replaced | 0.771 ± .010 | 0.779 ± .013 |
| All Markers Replaced | 0.770 | 0.775 |
| DF Model | 0.677 ± .042 | |

For the 5, 10, 15, 20 Markers replaced analyses, markers were selected at random 100 times for each of the analyses.

TABLE 17

| Markers | Delta AUC Ridge Regression | Delta AUC Logistic Regression | Markers | Term | Type | Predictive |
|---|---|---|---|---|---|---|
| AF161365.HNRPF.TFCP2 | 0 | 0 | 3 | 1 | Original | Yes |
| AF161365.TFCP2 | 0.003495 | 0.004097 | 2 | 1 | Original | Yes |
| AF161365.HNRPF | −0.00327 | −0.00391 | 2 | 1 | Original | Yes |
| AF161365.ACBD5.DDX18 | 0.00473 | 0.004762 | 3 | 1 | Substitute | Yes |
| AF161365.DDX18 | 4.22E−05 | 0.000243 | 2 | 1 | Substitute | Yes |
| AF161365.ACBD5 | −0.00278 | −0.0031 | 2 | 1 | Substitute | Yes |

TABLE 18

| Markers | Delta AUC Ridge Regression | Delta AUC Logistic Regression | Markers | Term | Type | Predictive |
|---|---|---|---|---|---|---|
| AF289562.HNRPF.TFCP2 | 0 | 0 | 3 | 2 | Original | Yes |
| AF289562.TFCP2 | −6.34E−05 | −0.00073 | 2 | 2 | Original | Yes |
| AF289562.HNRPF | 0.000549 | 0.000306 | 2 | 2 | Original | Yes |
| CD248.ACBD5.DDX18 | −0.00505 | −0.00625 | 3 | 2 | Substitute | Yes |
| CD248.DDX18 | −0.00535 | −0.00654 | 2 | 2 | Substitute | Yes |
| CD248.ACBD5 | −0.00506 | −0.00588 | 2 | 2 | Substitute | Yes |

TABLE 19

| Markers | Delta AUC Ridge Regression | Delta AUC Logistic Regression | Markers | Term | Predictive |
|---|---|---|---|---|---|
| CD3D.TMC8.CD79B.SPIB | 0 | 0 | 4 | 3 | Yes |
| CD3D.CD79B.SPIB | −0.00039 | −0.00056 | 3 | 3 | Yes |
| TMC8.CD79B.SPIB | 0 | 9.50E−05 | 3 | 3 | Yes |
| CD3D.TMC8.CD79B | 0.000612 | 0.000697 | 3 | 3 | Yes |
| CD3D.TMC8.SPIB | −0.00053 | −0.00041 | 3 | 3 | Yes |
| CD3D.CD79B | −0.00016 | 8.45E−05 | 2 | 3 | Yes |
| CD3D.SPIB | −0.00058 | −0.0008 | 2 | 3 | Yes |
| TMC8.CD79B | 0.00038 | 0.000676 | 2 | 3 | Yes |
| TMC8.SPIB | −0.00048 | −0.00023 | 2 | 3 | Yes |
| LCK.CCT2.CD19.BLK | −0.00846 | −0.00441 | 4 | 3 | No |
| LCK.CD19.BLK | −0.00838 | −0.00536 | 3 | 3 | No |
| CCT2.CD19.BLK | −0.00729 | −0.00463 | 3 | 3 | No |
| LCK.CCT2.CD19 | −0.00619 | −0.00338 | 3 | 3 | No |
| LCK.CCT2.BLK | −0.00043 | −0.00016 | 3 | 3 | Yes |
| LCK.CD19 | −0.00692 | −0.00316 | 2 | 3 | No |
| LCK.BLK | −0.00027 | −8.45E−05 | 2 | 3 | Yes |
| CCT2.CD19 | −0.00605 | −0.0017 | 2 | 3 | No |
| CCT2.BLK | −0.00036 | −0.00012 | 2 | 3 | Yes |
| CD3D.CD79B | −0.00016 | 8.45E−05 | 2 | 3 | Yes |
| CD3D.SPIB | −0.00058 | −0.0008 | 2 | 3 | Yes |
| CD3D.CD19 | −0.00729 | −0.00222 | 2 | 3 | No |
| CD3D.BLK | −0.00058 | −0.00034 | 2 | 3 | Yes |
| TMC8.CD79B | 0.00038 | 0.000676 | 2 | 3 | Yes |
| TMC8.SPIB | −0.00048 | −0.00023 | 2 | 3 | Yes |
| TMC8.CD19 | −0.00561 | −0.00134 | 2 | 3 | Mixed |
| TMC8.BLK | −0.00042 | −0.0007 | 2 | 3 | Yes |
| LCK.CD79B | −0.00073 | −0.00045 | 2 | 3 | Yes |
| LCK.SPIB | −0.00109 | −0.00118 | 2 | 3 | Yes |
| LCK.CD19 | −0.00692 | −0.00316 | 2 | 3 | No |
| LCK.BLK | −0.00027 | −8.45E−05 | 2 | 3 | Yes |
| CCT2.CD79B | 0.000106 | 0.000116 | 2 | 3 | Yes |
| CCT2.SPIB | −0.00057 | −0.0007 | 2 | 3 | Yes |
| CCT2.CD19 | −0.00605 | −0.0017 | 2 | 3 | No |
| CCT2.BLK | −0.00036 | −0.00012 | 2 | 3 | Yes |

TABLE 20

| Markers | Delta AUC Ridge Regression | Delta AUC Logistic Regression | Markers | Term | Type | Predictive |
|---|---|---|---|---|---|---|
| S100A12.CLEC4E.S100A8.RPL28 | 0 | 0 | 4 | 4 | Original | Yes |
| S100A12.CLEC4E.RPL28 | −0.00079 | −0.00079 | 3 | 4 | Original | Yes |
| S100A12.S100A8.RPL28 | −0.00068 | −0.00068 | 3 | 4 | Original | Yes |
| CLEC4E.S100A8.RPL28 | 0.000528 | 0.000528 | 3 | 4 | Original | Yes |
| S100A12.RPL28 | −0.00166 | −0.00166 | 2 | 4 | Original | Yes |
| CLEC4E.RPL28 | −0.00183 | −0.00183 | 2 | 4 | Original | Yes |
| S100A8.RPL28 | 0.000538 | 0.000538 | 2 | 4 | Original | Yes |
| MMP9.ALOX5AP.NAMPT.SSRP1 | −0.0003 | −0.0003 | 4 | 4 | Substitute | Yes |
| MMP9.ALOX5AP.SSRP1 | −0.00082 | −0.00082 | 3 | 4 | Substitute | Yes |
| MMP9.NAMPT.SSRP1 | −0.00052 | −0.00052 | 3 | 4 | Substitute | Yes |
| ALOX5AP.NAMPT.SSRP1 | 0.000169 | 0.000169 | 3 | 4 | Substitute | Yes |
| MMP9.SSRP1 | −0.00186 | −0.00186 | 2 | 4 | Substitute | Yes |
| ALOX5AP.SSRP1 | −3.17E−05 | −3.17E−05 | 2 | 4 | Substitute | Yes |
| NAMPT.SSRP1 | −0.0002 | −0.0002 | 2 | 4 | Substitute | Yes |

TABLE 21

| Markers | Delta AUC Ridge Regression | Delta AUC Logistic Regression | Markers | Term | Predictive |
|---|---|---|---|---|---|
| S100A12.CLEC4E.S100A8.AQP9.NCF4 | 0 | 0 | 5 | 5 | Yes |
| S100A12.CLEC4E.AQP9.NCF4 | −0.00021 | 0.000317 | 4 | 5 | Yes |
| S100A12.S100A8.AQP9.NCF4 | −0.00173 | −0.00269 | 4 | 5 | Yes |
| CLEC4E.S100A8.AQP9.NCF4 | 0.001014 | 0.001499 | 4 | 5 | Yes |
| S100A12.CLEC4E.S100A8.AQP9 | −0.00091 | −0.00105 | 4 | 5 | Yes |
| S100A12.CLEC4E.S100A8.NCF4 | 0.000348 | −0.00013 | 4 | 5 | Yes |
| S100A12.AQP9.NCF4 | −0.00249 | −0.00298 | 3 | 5 | Yes |
| CLEC4E.AQP9.NCF4 | −0.00016 | −0.00042 | 3 | 5 | Yes |
| S100A12.CLEC4E.AQP9 | −0.00103 | −0.00073 | 3 | 5 | Yes |
| S100A12.CLEC4E.NCF4 | 0.000243 | 9.50E−05 | 3 | 5 | Yes |
| S100A8.AQP9.NCF4 | −0.00108 | −0.00207 | 3 | 5 | Yes |
| S100A12.S100A8.AQP9 | −0.00226 | −0.00336 | 3 | 5 | Yes |
| S100A12.S100A8.NCF4 | −0.00141 | −0.00262 | 3 | 5 | Yes |
| CLEC4E.S100A8.AQP9 | 3.17E−05 | 0.000338 | 3 | 5 | Yes |
| CLEC4E.S100A8.NCF4 | 0.000771 | 0.000813 | 3 | 5 | Yes |
| S100A12.AQP9 | −0.0026 | −0.00363 | 2 | 5 | Yes |
| S100A12.NCF4 | −0.00227 | −0.00284 | 2 | 5 | Yes |
| CLEC4E.AQP9 | −0.00053 | −0.0009 | 2 | 5 | Yes |
| CLEC4E.NCF4 | −0.00024 | −0.00076 | 2 | 5 | Yes |
| S100A8.AQP9 | −0.00246 | −0.00325 | 2 | 5 | Yes |
| S100A8.NCF4 | −0.00091 | −0.00302 | 2 | 5 | Yes |
| MMP9.ALOX5AP.NAMPT.GLT1D1.NCF2 | −0.00325 | −0.00535 | 5 | 5 | Yes |
| MMP9.ALOX5AP.GLT1D1.NCF2 | −0.00498 | −0.00693 | 4 | 5 | No |
| MMP9.NAMPT.GLT1D1.NCF2 | −0.00311 | −0.00518 | 4 | 5 | Yes |
| ALOX5AP.NAMPT.GLT1D1.NCF2 | −0.00376 | −0.0057 | 4 | 5 | Yes |
| MMP9.ALOX5AP.NAMPT.GLT1D1 | −0.00339 | −0.0054 | 4 | 5 | Yes |
| MMP9.ALOX5AP.NAMPT.NCF2 | −0.00509 | −0.00703 | 4 | 5 | No |
| MMP9.GLT1D1.NCF2 | −0.00523 | −0.0071 | 3 | 5 | No |
| ALOX5AP.GLT1D1.NCF2 | −0.00402 | −0.00594 | 3 | 5 | Yes |
| MMP9.ALOX5AP.GLT1D1 | −0.00344 | −0.00538 | 3 | 5 | Yes |
| MMP9.ALOX5AP.NCF2 | −0.00488 | −0.00691 | 3 | 5 | No |
| NAMPT.GLT1D1.NCF2 | −0.00296 | −0.00516 | 3 | 5 | Yes |
| MMP9.NAMPT.GLT1D1 | −0.0033 | −0.00529 | 3 | 5 | Yes |
| MMP9.NAMPT.NCF2 | −0.00537 | −0.00736 | 3 | 5 | No |
| ALOX5AP.NAMPT.GLT1D1 | −0.00362 | −0.00534 | 3 | 5 | Yes |
| ALOX5AP.NAMPT.NCF2 | −0.0036 | −0.0056 | 3 | 5 | Yes |
| MMP9.GLT1D1 | −0.00518 | −0.00711 | 2 | 5 | No |
| MMP9.NCF2 | −0.00516 | −0.00706 | 2 | 5 | No |
| ALOX5AP.GLT1D1 | −0.00404 | −0.00613 | 2 | 5 | Yes |
| ALOX5AP.NCF2 | −0.00433 | −0.00623 | 2 | 5 | No |
| NAMPT.GLT1D1 | −0.00266 | −0.00437 | 2 | 5 | Yes |
| NAMPT.NCF2 | −0.00303 | −0.00566 | 2 | 5 | Yes |
| S100A12.AQP9 | −0.0026 | −0.00363 | 2 | 5 | Yes |
| S100A12.NCF4 | −0.00227 | −0.00284 | 2 | 5 | Yes |
| S100A12.GLT1D1 | −0.00245 | −0.00356 | 2 | 5 | Yes |
| S100A12.NCF2 | −0.00359 | −0.00476 | 2 | 5 | Yes |
| CLEC4E.AQP9 | −0.00053 | −0.0009 | 2 | 5 | Yes |
| CLEC4E.NCF4 | −0.00024 | −0.00076 | 2 | 5 | Yes |
| CLEC4E.GLT1D1 | −0.00023 | −0.001 | 2 | 5 | Yes |
| CLEC4E.NCF2 | −0.00113 | −0.00249 | 2 | 5 | Yes |
| S100A8.AQP9 | −0.00246 | −0.00325 | 2 | 5 | Yes |
| S100A8.NCF4 | −0.00091 | −0.00302 | 2 | 5 | Yes |
| S100A8.GLT1D1 | −0.00209 | −0.00289 | 2 | 5 | Yes |
| S100A8.NCF2 | −0.00297 | −0.00497 | 2 | 5 | Yes |
| MMP9.AQP9 | −0.00341 | −0.00537 | 2 | 5 | Yes |
| MMP9.NCF4 | −0.00317 | −0.00544 | 2 | 5 | Yes |
| MMP9.GLT1D1 | −0.00518 | −0.00711 | 2 | 5 | No |
| MMP9.NCF2 | −0.00516 | −0.00706 | 2 | 5 | No |
| ALOX5AP.AQP9 | −0.00481 | −0.00669 | 2 | 5 | No |
| ALOX5AP.NCF4 | −0.00386 | −0.00645 | 2 | 5 | Mixed |
| ALOX5AP.GLT1D1 | −0.00404 | −0.00613 | 2 | 5 | Yes |
| ALOX5AP.NCF2 | −0.00433 | −0.00623 | 2 | 5 | No |
| NAMPT.AQP9 | −0.00221 | −0.00344 | 2 | 5 | Yes |
| NAMPT.NCF4 | −0.00186 | −0.00385 | 2 | 5 | Yes |
| NAMPT.GLT1D1 | −0.00266 | −0.00437 | 2 | 5 | Yes |
| NAMPT.NCF2 | −0.00303 | −0.00566 | 2 | 5 | Yes |

TABLE 22

| Markers | Delta AUC Ridge Regression | Delta AUC Logistic Regression | Markers | Term | Predictive |
|---|---|---|---|---|---|
| CASP5.IL18RAP.TNFAIP6.IL8RB.TNFRSF10C.KCNE3.TLR4 | 0 | 0 | 7 | 6 | Yes |
| CASP5.IL18RAP.IL8RB.TNFRSF10C.KCNE3.TLR4 | −0.00726 | −0.00732 | 6 | 6 | Yes |
| CASP5.TNFAIP6.IL8RB.TNFRSF10C.KCNE3.TLR4 | −0.00772 | −0.00773 | 6 | 6 | Yes |
| IL18RAP.TNFAIP6.IL8RB.TNFRSF10C.KCNE3.TLR4 | 0.00226 | 0.002999 | 6 | 6 | Yes |
| CASP5.IL18RAP.TNFAIP6.IL8RB.TNFRSF10C.KCNE3 | −0.00147 | −0.00101 | 6 | 6 | Yes |
| CASP5.IL18RAP.TNFAIP6.IL8RB.TNFRSF10C.TLR4 | 0.001077 | 0.001045 | 6 | 6 | Yes |
| CASP5.IL18RAP.TNFAIP6.IL8RB.KCNE3.TLR4 | 0.000644 | 0.000296 | 6 | 6 | Yes |
| CASP5.IL18RAP.TNFAIP6.TNFRSF10C.KCNE3.TLR4 | −0.0012 | −0.00038 | 6 | 6 | Yes |
| CASP5.IL8RB.TNFRSF10C.KCNE3.TLR4 | −0.01475 | −0.01514 | 5 | 6 | Yes |
| IL18RAP.IL8RB.TNFRSF10C.KCNE3.TLR4 | −0.00966 | −0.00894 | 5 | 6 | Yes |
| CASP5.IL18RAP.IL8RB.TNFRSF10C.KCNE3 | −0.00788 | −0.008 | 5 | 6 | Yes |
| CASP5.IL18RAP.IL8RB.TNFRSF10C.TLR4 | −0.00707 | −0.00668 | 5 | 6 | Yes |
| CASP5.IL18RAP.IL8RB.KCNE3.TLR4 | −0.00706 | −0.00693 | 5 | 6 | Yes |
| CASP5.IL18RAP.TNFRSF10C.KCNE3.TLR4 | −0.00785 | −0.00776 | 5 | 6 | Yes |
| TNFAIP6.IL8RB.TNFRSF10C.KCNE3.TLR4 | −0.00696 | −0.00669 | 5 | 6 | Yes |
| CASP5.TNFAIP6.IL8RB.TNFRSF10C.KCNE3 | −0.00842 | −0.0081 | 5 | 6 | Yes |
| CASP5.TNFAIP6.IL8RB.TNFRSF10C.TLR4 | −0.00771 | −0.00776 | 5 | 6 | Yes |
| CASP5.TNFAIP6.IL8RB.KCNE3.TLR4 | −0.00722 | −0.00741 | 5 | 6 | Yes |
| CASP5.TNFAIP6.TNFRSF10C.KCNE3.TLR4 | −0.00815 | −0.00809 | 5 | 6 | Yes |
| IL18RAP.TNFAIP6.IL8RB.TNFRSF10C.KCNE3 | 0.001066 | 0.00151 | 5 | 6 | Yes |
| IL18RAP.TNFAIP6.IL8RB.TNFRSF10C.TLR4 | 0.001795 | 0.003252 | 5 | 6 | Yes |
| IL18RAP.TNFAIP6.IL8RB.KCNE3.TLR4 | 0.002745 | 0.003822 | 5 | 6 | Yes |
| IL18RAP.TNFAIP6.TNFRSF10C.KCNE3.TLR4 | 0.001626 | 0.003305 | 5 | 6 | Yes |
| CASP5.IL18RAP.TNFAIP6.IL8RB.TNFRSF10C | −0.00061 | −0.00029 | 5 | 6 | Yes |
| CASP5.IL18RAP.TNFAIP6.IL8RB.KCNE3 | −0.00103 | 1.06E−05 | 5 | 6 | Yes |
| CASP5.IL18RAP.TNFAIP6.TNFRSF10C.KCNE3 | −0.00291 | −0.00322 | 5 | 6 | Yes |
| CASP5.IL18RAP.TNFAIP6.IL8RB.TLR4 | 0.002492 | 0.002714 | 5 | 6 | Yes |
| CASP5.IL18RAP.TNFAIP6.TNFRSF10C.TLR4 | −0.0005 | −0.00052 | 5 | 6 | Yes |
| CASP5.IL18RAP.TNFAIP6.KCNE3.TLR4 | −0.00096 | −0.0004 | 5 | 6 | Yes |
| CASP5.IL18RAP.TNFRSF10C.KCNE3 | −0.01477 | −0.01564 | 4 | 6 | Yes |
| CASP5.IL8RB.TNFRSF10C.TLR4 | −0.01456 | −0.01506 | 4 | 6 | Yes |
| CASP5.IL8RB.KCNE3.TLR4 | −0.01438 | −0.01466 | 4 | 6 | Yes |
| CASP5.TNFRSF10C.KCNE3.TLR4 | −0.01449 | −0.01482 | 4 | 6 | Yes |
| IL18RAP.IL8RB.TNFRSF10C.KCNE3 | −0.00979 | −0.00959 | 4 | 6 | Yes |
| IL18RAP.IL8RB.TNFRSF10C.TLR4 | −0.00982 | −0.00881 | 4 | 6 | Yes |
| IL18RAP.IL8RB.KCNE3.TLR4 | −0.00926 | −0.00856 | 4 | 6 | Yes |
| IL18RAP.TNFRSF10C.KCNE3.TLR4 | −0.00952 | −0.00899 | 4 | 6 | Yes |
| CASP5.IL18RAP.IL8RB.TNFRSF10C | −0.00777 | −0.00745 | 4 | 6 | Yes |
| CASP5.IL18RAP.IL8RB.KCNE3 | −0.00763 | −0.00746 | 4 | 6 | Yes |
| CASP5.IL18RAP.TNFRSF10C.KCNE3 | −0.00871 | −0.00871 | 4 | 6 | Yes |
| CASP5.IL18RAP.IL8RB.TLR4 | −0.00598 | −0.00571 | 4 | 6 | Yes |
| CASP5.IL18RAP.TNFRSF10C.TLR4 | −0.00733 | −0.00724 | 4 | 6 | Yes |
| CASP5.IL18RAP.KCNE3.TLR4 | −0.00755 | −0.00775 | 4 | 6 | Yes |
| TNFAIP6.IL8RB.TNFRSF10C.KCNE3 | −0.00715 | −0.00729 | 4 | 6 | Yes |
| TNFAIP6.IL8RB.TNFRSF10C.TLR4 | −0.00744 | −0.00638 | 4 | 6 | Yes |
| TNFAIP6.IL8RB.KCNE3.TLR4 | −0.00641 | −0.00627 | 4 | 6 | Yes |
| TNFAIP6.TNFRSF10C.KCNE3.TLR4 | −0.00668 | −0.00641 | 4 | 6 | Yes |
| CASP5.TNFAIP6.IL8RB.TNFRSF10C | −0.00867 | −0.0087 | 4 | 6 | Yes |
| CASP5.TNFAIP6.IL8RB.KCNE3 | −0.00781 | −0.00814 | 4 | 6 | Yes |
| CASP5.TNFAIP6.TNFRSF10C.KCNE3 | −0.00926 | −0.00908 | 4 | 6 | Yes |
| CASP5.TNFAIP6.IL8RB.TLR4 | −0.0068 | −0.00666 | 4 | 6 | Yes |
| CASP5.TNFAIP6.TNFRSF10C.TLR4 | −0.00852 | −0.00834 | 4 | 6 | Yes |
| CASP5.TNFAIP6.KCNE3.TLR4 | −0.00793 | −0.00791 | 4 | 6 | Yes |
| IL18RAP.TNFAIP6.IL8RB.TNFRSF10C | −6.34E−05 | 0.000813 | 4 | 6 | Yes |
| IL18RAP.TNFAIP6.IL8RB.KCNE3 | 0.001542 | 0.002175 | 4 | 6 | Yes |
| IL18RAP.TNFAIP6.TNFRSF10C.KCNE3 | 0.000285 | 0.00057 | 4 | 6 | Yes |
| IL18RAP.TNFAIP6.IL8RB.TLR4 | 0.003347 | 0.004878 | 4 | 6 | Yes |
| IL18RAP.TNFAIP6.TNFRSF10C.TLR4 | 0.001594 | 0.002502 | 4 | 6 | Yes |
| IL18RAP.TNFAIP6.KCNE3.TLR4 | 0.001795 | 0.002566 | 4 | 6 | Yes |
| CASP5.IL18RAP.TNFAIP6.IL8RB | −0.00015 | 0.001193 | 4 | 6 | Yes |
| CASP5.IL18RAP.TNFAIP6.TNFRSF10C | −0.00385 | −0.00361 | 4 | 6 | Yes |
| CASP5.IL18RAP.TNFAIP6.KCNE3 | −0.00364 | −0.0031 | 4 | 6 | Yes |
| CASP5.IL18RAP.TNFAIP6.TLR4 | −0.00058 | −0.00041 | 4 | 6 | Yes |
| CASP5.IL8RB.TNFRSF10C | −0.01523 | −0.01583 | 3 | 6 | Yes |
| CASP5.IL8RB.KCNE3 | −0.01468 | −0.01507 | 3 | 6 | Yes |
| CASP5.TNFRSF10C.KCNE3 | −0.01494 | −0.01568 | 3 | 6 | Yes |
| CASP5.IL8RB.TLR4 | −0.01426 | −0.01487 | 3 | 6 | Yes |
| CASP5.TNFRSF10C.TLR4 | −0.01482 | −0.0152 | 3 | 6 | Yes |
| CASP5.KCNE3.TLR4 | −0.01459 | −0.01474 | 3 | 6 | Yes |
| IL18RAP.IL8RB.TNFRSF10C | −0.01037 | −0.00964 | 3 | 6 | Yes |
| IL18RAP.IL8RB.KCNE3 | −0.01 | −0.00946 | 3 | 6 | Yes |
| IL18RAP.TNFRSF10C.KCNE3 | −0.01029 | −0.00963 | 3 | 6 | Yes |
| IL18RAP.IL8RB.TLR4 | −0.00926 | −0.00805 | 3 | 6 | Yes |
| IL18RAP.TNFRSF10C.TLR4 | −0.00991 | −0.0089 | 3 | 6 | Yes |
| IL18RAP.KCNE3.TLR4 | −0.0091 | −0.00833 | 3 | 6 | Yes |
| CASP5.IL18RAP.IL8RB | −0.00718 | −0.00648 | 3 | 6 | Yes |

TABLE 22-continued

| Markers | Delta AUC Ridge Regression | Delta AUC Logistic Regression | Markers | Term | Predictive |
|---|---|---|---|---|---|
| CASP5.IL18RAP.TNFRSF10C | −0.00915 | −0.00916 | 3 | 6 | Yes |
| CASP5.IL18RAP.KCNE3 | −0.00891 | −0.00872 | 3 | 6 | Yes |
| CASP5.IL18RAP.TLR4 | −0.00688 | −0.00775 | 3 | 6 | Yes |
| TNFAIP6.IL8RB.TNFRSF10C | −0.00786 | −0.00752 | 3 | 6 | Yes |
| TNFAIP6.IL8RB.KCNE3 | −0.00686 | −0.00644 | 3 | 6 | Yes |
| TNFAIP6.TNFRSF10C.KCNE3 | −0.00771 | −0.00749 | 3 | 6 | Yes |
| TNFAIP6.IL8RB.TLR4 | −0.00668 | −0.0056 | 3 | 6 | Yes |
| TNFAIP6.TNFRSF10C.TLR4 | −0.00765 | −0.0068 | 3 | 6 | Yes |
| TNFAIP6.KCNE3.TLR4 | −0.00623 | −0.00608 | 3 | 6 | Yes |
| CASP5.TNFAIP6.IL8RB | −0.0079 | −0.00708 | 3 | 6 | Yes |
| CASP5.TNFAIP6.TNFRSF10C | −0.00996 | −0.00988 | 3 | 6 | Yes |
| CASP5.TNFAIP6.KCNE3 | −0.00935 | −0.00929 | 3 | 6 | Yes |
| CASP5.TNFAIP6.TLR4 | −0.00745 | −0.00787 | 3 | 6 | Yes |
| IL18RAP.TNFAIP6.IL8RB | 0.000549 | 0.00189 | 3 | 6 | Yes |
| IL18RAP.TNFAIP6.INFRSF10C | −0.00174 | −0.00122 | 3 | 6 | Yes |
| IL18RAP.TNFAIP6.KCNE3 | −0.00038 | 0.00037 | 3 | 6 | Yes |
| IL18RAP.TNFAIP6.TLR4 | 0.001552 | 0.002249 | 3 | 6 | Yes |
| CASP5.IL8RB | −0.01498 | −0.01537 | 2 | 6 | Yes |
| CASP5.TNFRSF10C | −0.01527 | −0.01602 | 2 | 6 | Yes |
| CASP5.KCNE3 | −0.01471 | −0.0152 | 2 | 6 | Yes |
| CASP5.TLR4 | −0.01426 | −0.01449 | 2 | 6 | Yes |
| IL18RAP.IL8RB | −0.00983 | −0.00922 | 2 | 6 | Yes |
| IL18RAP.TNFRSF10C | −0.01126 | −0.01029 | 2 | 6 | Yes |
| IL18RAP.KCNE3 | −0.0097 | −0.01001 | 2 | 6 | Yes |
| IL18RAP.TLR4 | −0.00878 | −0.00829 | 2 | 6 | Yes |
| TNFAIP6.IL8RB | −0.00724 | −0.00667 | 2 | 6 | Yes |
| TNFAIP6.TNFRSF10C | −0.00924 | −0.00868 | 2 | 6 | Yes |
| TNFAIP6.KCNE3 | −0.00752 | −0.00694 | 2 | 6 | Yes |
| TNFAIP6.TLR4 | −0.00663 | −0.00632 | 2 | 6 | Yes |
| H3F3B.TXN.PLAUR.BCL2A1.PTAFR.LAMP2.TYROBP | −0.01883 | −0.01929 | 7 | 6 | Yes |
| H3F3B.TXN.BCL2A1.PTAFR.LAMP2.TYROBP | −0.01979 | −0.02006 | 6 | 6 | Yes |
| H3F3B.PLAUR.BCL2A1.PTAFR.LAMP2.TYROBP | −0.01852 | −0.01892 | 6 | 6 | Yes |
| TXN.PLAUR.BCL2A1.PTAFR.LAMP2.TYROBP | −0.01845 | −0.01856 | 6 | 6 | Yes |
| H3F3B.TXN.PLAUR.BCL2A1.PTAFR.LAMP2 | −0.01891 | −0.01913 | 6 | 6 | Yes |
| H3F3B.TXN.PLAUR.BCL2A1.PTAFR.TYROBP | −0.01909 | −0.01945 | 6 | 6 | Yes |
| H3F3B.TXN.PLAUR.BCL2A1.LAMP2.TYROBP | −0.01989 | −0.02008 | 6 | 6 | Yes |
| H3F3B.TXN.PLAUR.PTAFR.LAMP2.TYROBP | −0.01823 | −0.01798 | 6 | 6 | Yes |
| H3F3B.BCL2A1.PTAFR.LAMP2.TYROBP | −0.01985 | −0.01997 | 5 | 6 | Yes |
| TXN.BCL2A1.PTAFR.LAMP2.TYROBP | −0.01978 | −0.0199 | 5 | 6 | Yes |
| H3F3B.TXN.BCL2A1.PTAFR.LAMP2 | −0.0195 | −0.01968 | 5 | 6 | Yes |
| H3F3B.TXN.BCL2A1.PTAFR.TYROBP | −0.02001 | −0.02022 | 5 | 6 | Yes |
| H3F3B.TXN.BCL2A1.LAMP2.TYROBP | −0.02077 | −0.02088 | 5 | 6 | No |
| H3F3B.TXN.PTAFR.LAMP2.TYROBP | −0.01929 | −0.01949 | 5 | 6 | Yes |
| PLAUR.BCL2A1.PTAFR.LAMP2.TYROBP | −0.0192 | −0.0192 | 5 | 6 | Yes |
| H3F3B.PLAUR.BCL2A1.PTAFR.LAMP2 | −0.01879 | −0.01932 | 5 | 6 | Yes |
| H3F3B.PLAUR.BCL2A1.PTAFR.TYROBP | −0.01904 | −0.0194 | 5 | 6 | Yes |
| H3F3B.PLAUR.BCL2A1.LAMP2.TYROBP | −0.01934 | −0.01953 | 5 | 6 | Yes |
| H3F3B.PLAUR.PTAFR.LAMP2.TYROBP | −0.01801 | −0.01798 | 5 | 6 | Yes |
| TXN.PLAUR.BCL2A1.PTAFR.LAMP2 | −0.01863 | −0.01884 | 5 | 6 | Yes |
| TXN.PLAUR.BCL2A1.PTAFR.TYROBP | −0.01971 | −0.01955 | 5 | 6 | Yes |
| TXN.PLAUR.BCL2A1.LAMP2.TYROBP | −0.01923 | −0.01932 | 5 | 6 | Yes |
| TXN.PLAUR.PTAFR.LAMP2.TYROBP | −0.01834 | −0.01792 | 5 | 6 | Yes |
| H3F3B.TXN.PLAUR.BCL2A1.PTAFR | −0.01945 | −0.01958 | 5 | 6 | Yes |
| H3F3B.TXN.PLAUR.BCL2A1.LAMP2 | −0.01999 | −0.02012 | 5 | 6 | Yes |
| H3F3B.TXN.PLAUR.PTAFR.LAMP2 | −0.01816 | −0.01784 | 5 | 6 | Yes |
| H3F3B.TXN.PLAUR.BCL2A1.TYROBP | −0.02038 | −0.02064 | 5 | 6 | Yes |
| H3F3B.TXN.PLAUR.PTAFR.TYROBP | −0.01949 | −0.0195 | 5 | 6 | Yes |
| H3F3B.TXN.PLAUR.LAMP2.TYROBP | −0.01904 | −0.01909 | 5 | 6 | Yes |
| H3F3B.BCL2A1.PTAFR.LAMP2 | −0.01974 | −0.02007 | 4 | 6 | Yes |
| H3F3B.BCL2A1.PTAFR.TYROBP | −0.01984 | −0.02014 | 4 | 6 | Yes |
| H3F3B.BCL2A1.LAMP2.TYROBP | −0.01983 | −0.02014 | 4 | 6 | Yes |
| H3F3B.PTAFR.LAMP2.TYROBP | −0.01896 | −0.01932 | 4 | 6 | Yes |
| TXN.BCL2A1.PTAFR.LAMP2 | −0.01948 | −0.01943 | 4 | 6 | Yes |
| TXN.BCL2A1.PTAFR.TYROBP | −0.02009 | −0.02005 | 4 | 6 | Yes |
| TXN.BCL2A1.LAMP2.TYROBP | −0.02014 | −0.02012 | 4 | 6 | Yes |
| TXN.PTAFR.LAMP2.TYROBP | −0.01931 | −0.01992 | 4 | 6 | Yes |
| H3F3B.TXN.BCL2A1.PTAFR | −0.02017 | −0.02014 | 4 | 6 | Yes |
| H3F3B.TXN.BCL2A1.LAMP2 | −0.02053 | −0.02056 | 4 | 6 | No |
| H3F3B.TXN.PTAFR.LAMP2 | −0.01819 | −0.01867 | 4 | 6 | Yes |
| H3F3B.TXN.BCL2A1.TYROBP | −0.02078 | −0.02122 | 4 | 6 | No |
| H3F3B.TXN.PTAFR.TYROBP | −0.02018 | −0.02033 | 4 | 6 | Yes |
| H3F3B.TXN.LAMP2.TYROBP | −0.01999 | −0.02022 | 4 | 6 | Yes |
| PLAUR.BCL2A1.PTAFR.LAMP2 | −0.0192 | −0.01915 | 4 | 6 | Yes |
| PLAUR.BCL2A1.PTAFR.TYROBP | −0.01966 | −0.02001 | 4 | 6 | Yes |
| PLAUR.BCL2A1.LAMP2.TYROBP | −0.01947 | −0.01983 | 4 | 6 | Yes |
| PLAUR.PTAFR.LAMP2.TYROBP | −0.01847 | −0.01839 | 4 | 6 | Yes |

TABLE 22-continued

| Markers | Delta AUC Ridge Regression | Delta AUC Logistic Regression | Markers | Term | Predictive |
|---|---|---|---|---|---|
| H3F3B.PLAUR.BCL2A1.PTAFR | −0.01925 | −0.01924 | 4 | 6 | Yes |
| H3F3B.PLAUR.BCL2A1.LAMP2 | −0.01962 | −0.01999 | 4 | 6 | Yes |
| H3F3B.PLAUR.PTAFR.LAMP2 | −0.01779 | −0.01779 | 4 | 6 | Yes |
| H3F3B.PLAUR.BCL2A1.TYROBP | −0.01978 | −0.02003 | 4 | 6 | Yes |
| H3F3B.PLAUR.PTAFR.TYROBP | −0.01903 | −0.01932 | 4 | 6 | Yes |
| H3F3B.PLAUR.LAMP2.TYROBP | −0.01835 | −0.01842 | 4 | 6 | Yes |
| TXN.PLAUR.BCL2A1.PTAFR | −0.01895 | −0.0189 | 4 | 6 | Yes |
| TXN.PLAUR.BCL2A1.LAMP2 | −0.01947 | −0.01941 | 4 | 6 | Yes |
| TXN.PLAUR.PTAFR.LAMP2 | −0.01748 | −0.01746 | 4 | 6 | Yes |
| TXN.PLAUR.BCL2A1.TYROBP | −0.02086 | −0.02136 | 4 | 6 | No |
| TXN.PLAUR.PTAFR.TYROBP | −0.01936 | −0.01917 | 4 | 6 | Yes |
| TXN.PLAUR.LAMP2.TYROBP | −0.01876 | −0.01874 | 4 | 6 | Yes |
| H3F3B.TXN.PLAUR.BCL2A1 | −0.02057 | −0.02098 | 4 | 6 | No |
| H3F3B.TXN.PLAUR.PTAFR | −0.0182 | −0.01799 | 4 | 6 | Yes |
| H3F3B.TXN.PLAUR.LAMP2 | −0.0185 | −0.0186 | 4 | 6 | Yes |
| H3F3B.TXN.PLAUR.TYROBP | −0.02026 | −0.02086 | 4 | 6 | Yes |
| H3F3B.BCL2A1.PTAFR | −0.0199 | −0.02011 | 3 | 6 | Yes |
| H3F3B.BCL2A1.LAMP2 | −0.02034 | −0.02054 | 3 | 6 | Yes |
| H3F3B.PTAFR.LAMP2 | −0.01899 | −0.01887 | 3 | 6 | Yes |
| H3F3B.BCL2A1.TYROBP | −0.02078 | −0.02105 | 3 | 6 | No |
| H3F3B.PTAFR.TYROBP | −0.02001 | −0.02029 | 3 | 6 | Yes |
| H3F3B.LAMP2.TYROBP | −0.01974 | −0.02007 | 3 | 6 | Yes |
| TXN.BCL2A1.PTAFR | −0.01986 | −0.01992 | 3 | 6 | Yes |
| TXN.BCL2A1.LAMP2 | −0.01978 | −0.02016 | 3 | 6 | Yes |
| TXN.PTAFR.LAMP2 | −0.01891 | −0.01887 | 3 | 6 | Yes |
| TXN.BCL2A1.TYROBP | −0.02107 | −0.02132 | 3 | 6 | No |
| TXN.PTAFR.TYROBP | −0.02 | −0.02024 | 3 | 6 | Yes |
| TXN.LAMP2.TYROBP | −0.01962 | −0.02003 | 3 | 6 | Yes |
| H3F3B.TXN.BCL2A1 | −0.0211 | −0.02123 | 3 | 6 | No |
| H3F3B.TXN.PTAFR | −0.01906 | −0.01911 | 3 | 6 | Yes |
| H3F3B.TXN.LAMP2 | −0.0193 | −0.01958 | 3 | 6 | Yes |
| H3F3B.TXN.TYROBP | −0.0212 | −0.02144 | 3 | 6 | No |
| PLAUR.BCL2A1.PTAFR | −0.01948 | −0.01956 | 3 | 6 | Yes |
| PLAUR.BCL2A1.LAMP2 | −0.01952 | −0.0198 | 3 | 6 | Yes |
| PLAUR.PTAFR.LAMP2 | −0.01797 | −0.01784 | 3 | 6 | Yes |
| PLAUR.BCL2A1.TYROBP | −0.02012 | −0.02041 | 3 | 6 | Yes |
| PLAUR.PTAFR.TYROBP | −0.01907 | −0.01933 | 3 | 6 | Yes |
| PLAUR.LAMP2.TYROBP | −0.01889 | −0.01879 | 3 | 6 | Yes |
| H3F3B.PLAUR.BCL2A1 | −0.02017 | −0.02029 | 3 | 6 | Yes |
| H3F3B.PLAUR.PTAFR | −0.01819 | −0.01819 | 3 | 6 | Yes |
| H3F3B.PLAUR.LAMP2 | −0.01851 | −0.01851 | 3 | 6 | Yes |
| H3F3B.PLAUR.TYROBP | −0.01981 | −0.01982 | 3 | 6 | Yes |
| TXN.PLAUR.BCL2A1 | −0.02091 | −0.02139 | 3 | 6 | No |
| TXN.PLAUR.PTAFR | −0.01811 | −0.01817 | 3 | 6 | Yes |
| TXN.PLAUR.LAMP2 | −0.01777 | −0.01807 | 3 | 6 | Yes |
| TXN.PLAUR.TYROBP | −0.02058 | −0.02118 | 3 | 6 | No |
| H3F3B.BCL2A1 | −0.02045 | −0.02078 | 2 | 6 | No |
| H3F3B.PTAFR | −0.01928 | −0.0197 | 2 | 6 | Yes |
| H3F3B.LAMP2 | −0.01952 | −0.01982 | 2 | 6 | Yes |
| H3F3B.TYROBP | −0.02049 | −0.02082 | 2 | 6 | No |
| TXN.BCL2A1 | −0.02134 | −0.02159 | 2 | 6 | No |
| TXN.PTAFR | −0.01891 | −0.01933 | 2 | 6 | Yes |
| TXN.LAMP2 | −0.01943 | −0.0199 | 2 | 6 | Yes |
| TXN.TYROBP | −0.02144 | −0.02172 | 2 | 6 | No |
| PLAUR.BCL2A1 | −0.0202 | −0.02062 | 2 | 6 | Yes |
| PLAUR.PTAFR | −0.01811 | −0.01813 | 2 | 6 | Yes |
| PLAUR.LAMP2 | −0.01833 | −0.01797 | 2 | 6 | Yes |
| PLAUR.TYROBP | −0.01995 | −0.02038 | 2 | 6 | Yes |
| CASP5.IL8RB1 | −0.01498 | −0.01537 | 2 | 6 | Yes |
| CASP5.TNFRSF10C1 | −0.01527 | −0.01602 | 2 | 6 | Yes |
| CASP5.KCNE31 | −0.01471 | −0.0152 | 2 | 6 | Yes |
| CASP5.TLR41 | −0.01426 | −0.01449 | 2 | 6 | Yes |
| CASP5.BCL2A1 | −0.01551 | −0.016 | 2 | 6 | Yes |
| CASP5.PTAFR | −0.01515 | −0.01538 | 2 | 6 | Yes |
| CASP5.LAMP2 | −0.0153 | −0.01552 | 2 | 6 | Yes |
| CASP5.TYROBP | −0.01642 | −0.01626 | 2 | 6 | Yes |
| IL18RAP.IL8RB1 | −0.00983 | −0.00922 | 2 | 6 | Yes |
| IL18RAP.TNFRSF10C1 | −0.01126 | −0.01029 | 2 | 6 | Yes |
| IL18RAP.KCNE31 | −0.0097 | −0.01001 | 2 | 6 | Yes |
| IL18RAP.TLR41 | −0.00878 | −0.00829 | 2 | 6 | Yes |
| IL18RAP.BCL2A1 | −0.01217 | −0.01143 | 2 | 6 | Yes |
| IL18RAP.PTAFR | −0.01153 | −0.01101 | 2 | 6 | Yes |
| IL18RAP.LAMP2 | −0.01012 | −0.00998 | 2 | 6 | Yes |
| IL18RAP.TYROBP | −0.01198 | −0.01196 | 2 | 6 | Yes |
| TNFAIP6.IL8RB1 | −0.00724 | −0.00667 | 2 | 6 | Yes |
| TNFAIP6.TNFRSF10C1 | −0.00924 | −0.00868 | 2 | 6 | Yes |

TABLE 22-continued

| Markers | Delta AUC Ridge Regression | Delta AUC Logistic Regression | Markers | Term | Predictive |
| --- | --- | --- | --- | --- | --- |
| TNFAIP6.KCNE31 | −0.00752 | −0.00694 | 2 | 6 | Yes |
| TNFAIP6.TLR41 | −0.00663 | −0.00632 | 2 | 6 | Yes |
| TNFAIP6.BCL2A1 | −0.0102 | −0.0097 | 2 | 6 | Yes |
| TNFAIP6.PTAFR | −0.00952 | −0.00906 | 2 | 6 | Yes |
| TNFAIP6.LAMP2 | −0.00845 | −0.00774 | 2 | 6 | Yes |
| TNFAIP6.TYROBP | −0.01093 | −0.0105 | 2 | 6 | Yes |
| H3F3B.IL8RB | −0.0199 | −0.02009 | 2 | 6 | Yes |
| H3F3B.TNFRSF10C | −0.01956 | −0.01973 | 2 | 6 | Yes |
| H3F3B.KCNE3 | −0.01699 | −0.0169 | 2 | 6 | Yes |
| H3F3B.TLR4 | −0.01707 | −0.01722 | 2 | 6 | Yes |
| H3F3B.BCL2A1 | −0.02045 | −0.02078 | 2 | 6 | No |
| H3F3B.PTAFR | −0.01928 | −0.0197 | 2 | 6 | Yes |
| H3F3B.LAMP2 | −0.01952 | −0.01982 | 2 | 6 | Yes |
| H3F3B.TYROBP | −0.02049 | −0.02082 | 2 | 6 | No |
| TXN.IL8RB | −0.02074 | −0.02073 | 2 | 6 | No |
| TXN.TNFRSF10C | −0.02084 | −0.02143 | 2 | 6 | No |
| TXN.KCNE3 | −0.01775 | −0.01731 | 2 | 6 | Yes |
| TXN.TLR4 | −0.01782 | −0.01819 | 2 | 6 | Yes |
| TXN.BCL2A1 | −0.02134 | −0.02159 | 2 | 6 | No |
| TXN.PTAFR | −0.01891 | −0.01933 | 2 | 6 | Yes |
| TXN.LAMP2 | −0.01943 | −0.0199 | 2 | 6 | Yes |
| TXN.TYROBP | −0.02144 | −0.02172 | 2 | 6 | No |
| PLAUR.IL8RB | −0.01926 | −0.0191 | 2 | 6 | Yes |
| PLAUR.TNFRSF10C | −0.01955 | −0.01981 | 2 | 6 | Yes |
| PLAUR.KCNE3 | −0.01482 | −0.01437 | 2 | 6 | Yes |
| PLAUR.TLR4 | −0.0171 | −0.01682 | 2 | 6 | Yes |
| PLAUR.BCL2A1 | −0.0202 | −0.02062 | 2 | 6 | Yes |
| PLAUR.PTAFR | −0.01811 | −0.01813 | 2 | 6 | Yes |
| PLAUR.LAMP2 | −0.01833 | −0.01797 | 2 | 6 | Yes |
| PLAUR.TYROBP | −0.01995 | −0.02038 | 2 | 6 | Yes |

TABLE 23

| Markers | Delta AUC Ridge Regression | Delta AUC Logistic Regression | Markers | Term | Predictive |
| --- | --- | --- | --- | --- | --- |
| CD3D.TMC8.SLAMF7.KLRC4 | 0 | 0 | 4 | 7 | Yes |
| CD3D.SLAMF7.KLRC4 | −6.34E−05 | 1.06E−05 | 3 | 7 | Yes |
| TMC8.SLAMF7.KLRC4 | −0.00094 | −0.00103 | 3 | 7 | Yes |
| CD3D.TMC8.SLAMF7 | 0.003432 | 0.004065 | 3 | 7 | Yes |
| CD3D.TMC8.KLRC4 | −0.00269 | −0.00335 | 3 | 7 | Yes |
| CD3D.SLAMF7 | 0.00226 | 0.002766 | 2 | 7 | Yes |
| CD3D.KLRC4 | −0.0027 | −0.00332 | 2 | 7 | Yes |
| TMC8.SLAMF7 | 0.001594 | 0.001827 | 2 | 7 | Yes |
| TMC8.KLRC4 | −0.00351 | −0.00365 | 2 | 7 | Yes |
| LCK.CCT2.CX3CR1.CD8A | −0.01192 | −0.01099 | 4 | 7 | No |
| LCK.CX3CR1.CD8A | −0.01192 | −0.01143 | 3 | 7 | No |
| CCT2.CX3CR1.CD8A | −0.01192 | −0.01216 | 3 | 7 | No |
| LCK.CCT2.CX3CR1 | −0.00644 | −0.00646 | 3 | 7 | Yes |
| LCK.CCT2.CD8A | −0.01323 | −0.01304 | 3 | 7 | No |
| LCK.CX3CR1 | −0.00687 | −0.00729 | 2 | 7 | Yes |
| LCK.CD8A | −0.01382 | −0.01289 | 2 | 7 | No |
| CCT2.CX3CR1 | −0.00646 | −0.0061 | 2 | 7 | Yes |
| CCT2.CD8A | −0.01287 | −0.01253 | 2 | 7 | No |
| CD3D.SLAMF7 | 0.00226 | 0.002766 | 2 | 7 | Yes |
| CD3D.KLRC4 | −0.0027 | −0.00332 | 2 | 7 | Yes |
| CD3D.CX3CR1 | −0.00589 | −0.00615 | 2 | 7 | Yes |
| CD3D.CD8A | −0.01374 | −0.01231 | 2 | 7 | No |
| TMC8.SLAMF7 | 0.001594 | 0.001827 | 2 | 7 | Yes |
| TMC8.KLRC4 | −0.00351 | −0.00365 | 2 | 7 | Yes |
| TMC8.CX3CR1 | −0.00572 | −0.00602 | 2 | 7 | Yes |
| TMC8.CD8A | −0.01199 | −0.01121 | 2 | 7 | No |
| LCK.SLAMF7 | 0.000116 | 0.000285 | 2 | 7 | Yes |
| LCK.KLRC4 | −0.00436 | −0.0045 | 2 | 7 | Yes |
| LCK.CX3CR1 | −0.00687 | −0.00729 | 2 | 7 | Yes |
| LCK.CD8A | −0.01382 | −0.01289 | 2 | 7 | No |
| CCT2.SLAMF7 | 0.001795 | 0.002154 | 2 | 7 | Yes |
| CCT2.KLRC4 | −0.00403 | −0.00408 | 2 | 7 | Yes |
| CCT2.CX3CR1 | −0.00646 | −0.0061 | 2 | 7 | Yes |
| CCT2.CD8A | −0.01287 | −0.01253 | 2 | 7 | No |

TABLE 24

Clinical and Demographic Characteristics of the Final Development and Validation Patient Sets[1]

| Characteristic | Development | | | Validation | | |
|---|---|---|---|---|---|---|
| | Obstructive CAD[2] (N = 230) | No Obstructive CAD (N = 410) | P-value | Obstructive CAD (N = 192) | No Obstructive CAD (N = 334) | P-value |
| Age, mean (SD), y | 63.7 (11.1) | 57.2 (11.8) | <0.001 | 64.7 (9.8) | 57.7 (11.7) | <0.001 |
| Men, No. (%) | 180 (78.3%) | 193 (47.1%) | <0.001 | 134 (69.8%) | 165 (49.4%) | <0.001 |
| Chest pain type | | | <0.001 | | | <0.001 |
| Typical | 61 (26.5%) | 66 (16.1%) | | 42 (21.9%) | 41 (12.3%) | |
| Atypical | 28 (12.2%) | 56 (13.7%) | | 42 (21.9%) | 49 (14.7%) | |
| Non-cardiac | 47 (20.4%) | 137 (33.4%) | | 50 (26.0%) | 134 (40.1%) | |
| None | 91 (39.6%) | 143 (34.9%) | | 58 (30.2%) | 109 (32.6%) | |
| Blood pressure, mean (SD), mmHg | | | | | | |
| Systolic | 138 (17.7) | 133 (18.3) | <0.001 | 140 (17.7) | 132 (18.1) | <0.001 |
| Diastolic | 79.7 (11.0) | 79.6 (11.7) | 0.94 | 79.2 (11.3) | 77.5 (10.9) | 0.09 |
| Hypertension | 163 (70.9%) | 237 (57.8%) | 0.002 | 142 (74.0%) | 203 (60.8%) | 0.001 |
| Dyslipidemia | 170 (73.9%) | 225 (54.9%) | <0.001 | 133 (69.3%) | 208 (62.3%) | 0.11 |
| Curent smoking | 53 (23.2%) | 99 (24.3%) | 0.75 | 38 (19.8%) | 68 (20.4%) | 0.70 |
| BMI, mean (SD), kg/m2 | 30.5 (6.0) | 31.0 (7.5) | 0.35 | 29.8 (5.5) | 31.3 (7.0) | 0.01 |
| Ethnicity, White not Hispanic | 210 (91.3%) | 347 (84.6%) | 0.016 | 181 (94.3%) | 293 (87.7%) | 0.02 |
| Clinical syndrome | | | | | | |
| Stable angina | 123 (53.5%) | 214 (52.2%) | 0.78 | 107 (55.7%) | 176 (52.7%) | 0.46 |
| Unstable angina | 35 (15.2%) | 81 (19.8%) | 0.15 | 31 (16.1%) | 58 (17.4%) | 0.74 |
| Asymptomatic, high risk | 72 (31.3%) | 113 (27.6%) | 0.32 | 53 (27.6%) | 100 (29.9%) | 0.60 |
| Medications | | | | | | |
| Aspirin and salicylates | 153 (66.5%) | 232 (56.6%) | 0.03 | 139 (72.4%) | 205 (61.4%) | 0.01 |
| Statins | 109 (47.4%) | 142 (34.6%) | 0.003 | 93 (48.4%) | 127 (38.0%) | 0.02 |
| Beta blockers | 82 (35.7%) | 133 (32.4%) | 0.52 | 85 (44.3%) | 124 (37.1%) | 0.11 |
| ACE inhibitors | 57 (24.8%) | 67 (16.3%) | 0.01 | 47 (24.5%) | 64 (19.2%) | 0.16 |
| Angiotensin receptor blockers | 29 (12.6%) | 39 (9.5%) | 0.26 | 18 (9.4%) | 34 (10.2%) | 0.76 |
| Calcium channel blockers | 33 (14.3%) | 46 (11.2%) | 0.29 | 26 (13.5%) | 34 (10.2%) | 0.25 |
| Antiplatelet agents | 27 (11.7%) | 21 (5.1%) | 0.003 | 16 (8.3%) | 17 (5.1%) | 0.14 |
| Steroids, not systemic | 23 (10.0%) | 33 (8.0%) | 0.45 | 19 (9.9%) | 38 (11.4%) | 0.59 |
| NSAIDS | 47 (20.4%) | 78 (19.0%) | 0.76 | 30 (15.6%) | 58 (17.4%) | 0.60 |

[1]Characteristics of the 640 subjects in the Algorithm Development and 526 subjects in the Validation sets. P values were calculated by t-tests for continuous variables and using chi-square tests for discrete variables. Significant p values in both sets are bolded and underlined and are bolded if significant in single sets.
[2]Obstructive CAD is defined as >50% luminal stenosis in ≥1 major vessel by QCA.

TABLE 25A

Reclassification analysis of Gene Expression Algorithm with Diamond-Forrester Clinical Model

| | With Gene Expression Algorithm | | | | Reclassified % | | |
|---|---|---|---|---|---|---|---|
| | Low | Int. | High | Total | Lower | Higher | Total |
| D-F Low Risk | | | | | | | |
| Patients included | 118 | 96 | 38 | 252 | 0.0 | 15.1 | 15.1 |
| Disease pts | 16 | 19 | 22 | 57 | 0.0 | 38.6 | 38.6 |
| Non disease pts | 102 | 77 | 16 | 195 | 0.0 | 8.2 | 8.2 |
| Observed risk | 14% | 20% | 58% | 23% | — | | — |
| D-F Int Risk | | | | | | | |
| Patients included | 28 | 21 | 47 | 96 | 29.2 | 49.0 | 78.1 |
| Disease pts | 7 | 11 | 26 | 44 | 15.9 | 59.1 | 75.0 |
| Non disease pts | 21 | 10 | 21 | 52 | 40.4 | 40.4 | 80.8 |
| Observed risk | 25% | 52% | 55% | 46% | — | | — |
| D-F High Risk | | | | | | | |
| Patients included | 28 | 60 | 89 | 177 | 15.8 | 0.0 | 15.8 |
| Disease pts | 6 | 29 | 56 | 91 | 6.6 | 0.0 | 6.6 |
| Non disease pts | 22 | 31 | 33 | 86 | 38.4 | 0.0 | 38.4 |
| Observed risk | 21% | 48% | 63% | 51% | — | | — |
| Total Patients included | 174 | 77 | 174 | 525 | | | |
| Disease pts | 29 | 59 | 104 | 192 | | | |

TABLE 25A-continued

Reclassification analysis of Gene Expression Algorithm with Diamond-Forrester Clinical Model

| | With Gene Expression Algorithm | | | | Reclassified % | | |
|---|---|---|---|---|---|---|---|
| | Low | Int. | High | Total | Lower | Higher | Total |
| Non disease pts | 145 | 118 | 70 | 333 | | | |
| Observed risk | 17% | 33% | 60% | 37% | | | |

Risk categories: : Low = 0-<20%, Intermediate = ≥20-50%, High = ≥50%.
Classification improved in 18.2% of disease patients and improved in 1.8% of non disease patients for a net reclassification improvement of 20.0% ($p < .001$)

TABLE 25B

Reclassification analysis of Gene Expression Algorithm with MPI Results

| | With Gene Expression Algorithm | | | | Reclassified % | | |
|---|---|---|---|---|---|---|---|
| | Low | Int. | High | Total | Lower | Higher | Total |
| MPI Negative | | | | | | | |
| Patients included | 41 | 31 | 15 | 87 | 0.0 | 17.4 | 17.4 |
| Disease pts | 7 | 8 | 7 | 22 | 0.0 | 31.8 | 31.8 |
| Non disease pts | 34 | 23 | 8 | 65 | 0.0 | 12.3 | 12.3 |
| Observed risk | 17% | 26% | 47% | 25% | — | | — |
| MPI Positive | | | | | | | |
| Patients included | 57 | 78 | 88 | 223 | 25.6 | 0.0 | 25.6 |
| Disease pts | 6 | 21 | 49 | 76 | 7.9 | 0.0 | 7.9 |
| Non disease pts | 51 | 57 | 39 | 147 | 34.7 | 0.0 | 34.7 |
| Observed risk | 11% | 27% | 56% | 34% | — | | — |
| Total | | | | | | | |
| Patients included | 98 | 109 | 103 | 310 | | | |
| Disease pts | 13 | 29 | 56 | 98 | | | |
| Non disease pts | 85 | 80 | 47 | 212 | | | |
| Observed risk | 13% | 27% | 54% | 32% | | | |

Risk categories: : Low = 0-<20%, Intermediate = ≥20-50%, High = ≥50%.
Classification improved in 1.0% of disease patients and improved in 20.3% of non disease patients for a net reclassification improvement of 21.3% ($p < .001$)

Sequence Listing

Primers and Probes

| Assay ID | Symbol | Forward Primer | Reverse Primer | Probe |
|---|---|---|---|---|
| CDXR0728-SP1 | AF289562 | ACAGGAGGGAGGGATGCA (SEQ. ID NO. 1) | GCCAATCACCTGCCTAATGC (SEQ. ID NO. 2) | TCAGGCAGCCCCCCAGAG (SEQ. ID NO. 3) |
| CDXR0868-SP1 | AQP9 | ACCTGAGTCCCAGACTTTTCACT (SEQ. ID NO. 4) | CCACTACAGGAATCCACCAGAAG (SEQ. ID NO. 5) | CTTCAGAGCTGGAAACAA (SEQ. ID NO. 6) |
| CDXR0830-SP1 | CASP5 | CGAGCAACCTTGACAAGAGATTTC (SEQ. ID NO. 7) | GGTAAATGTGCTCTTTGATGTTGACA (SEQ. ID NO. 8) | CCTGTGGTTTCATTTTC (SEQ. ID NO. 9) |
| CDXR0884-SP2 | CD79B | CAGACGCTGCTGATCATCCT (SEQ. ID NO. 10) | TCGTAGGTGTGATCTTCCTCCAT (SEQ. ID NO. 11) | CCTTGCTGTCATCCTTGTC (SEQ. ID NO. 12) |
| CDXR0863-SP1 | CLEC4E | GGACGGCACACCTTTGACA (SEQ. ID NO. 13) | CCTCCAGGGTAGCTATGTTGTTG (SEQ. ID NO. 14) | CCCAGAAGCTCAGAGACT (SEQ. ID NO. 15) |
| CDXR0080-SP1 | IL18RAP | AGCCTGTGTTTGCTTGAAAGAGAT (SEQ. ID NO. 16) | TCTTCTGCTTCTCTTAATAATGCTCACAA (SEQ. ID NO. 17) | TCTTCTGCATACACTCCTCC (SEQ. ID NO. 18) |

-continued

| Primers and Probes | | | | |
|---|---|---|---|---|
| Assay ID | Symbol | Forward Primer | Reverse Primer | Probe |
| CDXR0832-SP1 | IL8RB | CCCCATTGTGGTCACAGGAA (SEQ. ID NO. 19) | CCAGGGCAAGCTTTCTAAACCAT (SEQ. ID NO. 20) | ACGTTCTTACTAGTTTCCC (SEQ. ID NO. 21) |
| CDXR0888-SP0 | KCNE3 | TCTCTAAGGCTCTATCAGTTCTGACAT (SEQ. ID NO. 22) | GCTGGAACCATATATGAAACTACGATACT (SEQ. ID NO. 23) | CCTACAAACACAGTGATTACA (SEQ. ID NO. 24) |
| CDXR0861-SP1 | KLRC4 | TGTATTGGAGTACTGGAGCAGAACA (SEQ. ID NO. 25) | CTGTTGGAATATGTAATCCACTCCTCA (SEQ. ID NO. 26) | CAATGACGTGCTTTCTG (SEQ. ID NO. 27) |
| CDXR0826-SP1 | NCF4 | CTCCCAGAAGCGCCTCTT (SEQ. ID NO. 28) | GGGACACCGTCAGCTCATG (SEQ. ID NO. 29) | CACGCAGAAGGACAACT (SEQ. ID NO. 30) |
| CDXR0056P1-SP1 | S100A12 | TCTCTAAGGGTGAGCTGAAGCA (SEQ. ID NO. 31) | CCAGGCCTTGGAATATTTCATCAATG (SEQ. ID NO. 32) | CAAACACCATCAAGAATAT (SEQ. ID NO. 33) |
| CDXR0069P1-SP1 | S100A8 | GAAGAAATTGCTAGAGACCGAGTGT (SEQ. ID NO. 34) | GCACCATCAGTGTTGATATCCAACT (SEQ. ID NO. 35) | CACCCTTTTTCCTGATATACT (SEQ. ID NO. 36) |
| CDXR0663-SP1 | SLAMF7 | AGCAAATACGGTTTACTCCACTGT (SEQ. ID NO. 37) | GGCATCGTGAGCAGTGAGT (SEQ. ID NO. 38) | TTTTCCATCTTTTTCGGTATTTC (SEQ. ID NO. 39) |
| CDXR0840-SP1 | SPIB | GAGGCCCTCGTGGCT (SEQ. ID NO. 40) | TGGTACAGGCGCAGCTT (SEQ. ID NO. 41) | CTTGCGAGTCCCTGCCTC (SEQ. ID NO. 42) |
| CDXR0672-SP1 | TFCP2 | ACAGAACTTTCAGGAAGAAGCATGT (SEQ. ID NO. 43) | CCGCACTCCTACTTCAGTATGAT (SEQ. ID NO. 44) | ACAATGAAAGCAGAAACC (SEQ. ID NO. 45) |
| CDXR0891-SP0 | TLR4 | GGGAAGAGTGGATGTTATCATTGAGAA (SEQ. ID NO. 46) | GGATGAACATTCTTTTCTGGGAACCT (SEQ. ID NO. 47) | ATGTGTCTGGAATTAATG (SEQ. ID NO. 48) |
| CDXR0876-SP1 | TMC8 | CACAGGCTCCGGAAGCA (SEQ. ID NO. 49) | CGCGACAGGTCCTCCAC (SEQ. ID NO. 50) | CTGGTGTGGCAGGTTC (SEQ. ID NO. 51) |
| CDXR0857-SP1 | TNFAIP6 | GGAGATGAGCTTCCAGATGACAT (SEQ. ID NO. 52) | AGCTGTCACTGAAGCATCACTTAG (SEQ. ID NO. 53) | CATCAGTACAGGAAATGTC (SEQ. ID NO. 54) |
| CDXR0844-SP1 | TNFRSF10C | GGAATGAAAACTCCCCAGAGATGTG (SEQ. ID NO. 55) | CAGGACGTACAATTACTGACTTGGA (SEQ. ID NO. 56) | CTAGGGCACCTGCTACAC (SEQ. ID NO. 57) |
| CDXR0121-SP1 | AF161365 | GCCTTGGAACACACCTTCGT (SEQ. ID NO. 58) | CAGGACACACTTCCGATGGATTTA (SEQ. ID NO. 59) | CCCCAGGAGTTGCTG (SEQ. ID NO. 60) |
| CDXR0703-SP1 | HNRPF | CCAGAAGTGTCTCCCACTGAAG (SEQ. ID NO. 61) | GGTGATCTTGGGTGTGGCTTT (SEQ. ID NO. 62) | TTTGTGGCTTAAAAACAACC (SEQ. ID NO. 63) |
| A23P208358-188 | RPL28 | CGGACCACCATCAACAAGAATG (SEQ. ID NO. 64) | TTCTTGCGGATCATGTGTCTGA (SEQ. ID NO. 65) | CTCGCGCCACGCTCA (SEQ. ID NO. 66) |

We claim:

1. A method for determining coronary artery disease risk in a subject, comprising:
performing a reverse transcriptase polymerase chain reaction (RT-PCR) assay on a sample from the subject by using a plurality of distinct primer and probe sets that specifically hybridize to mRNA corresponding to each gene in at least one term selected from the group consisting of term 1, term 2, term 3, term 4, term 5, term 6, and term 7;
wherein term 1 comprises gene 1, gene 2, and gene 3, wherein gene 1 is AF161365, wherein gene 2 is HNRPF or ACBD5, and wherein gene 3 is TFCP2 or DDX18;
wherein term 2 comprises gene 4, gene 5, and gene 6, wherein gene 4 is AF289562 or CD248, wherein gene 5 is HNRPF or ACBD5, and wherein gene 6 is TFCP2 or DDX18;
wherein term 3 comprises gene 7, gene 8, gene 9, and gene 10 wherein gene 7 is CD79B or CD19, wherein gene 8 is SPIB or BLK, wherein gene 9 is CD3D or LCK, and wherein gene 10 is TMC8 or CCT2;
wherein term 4 comprises gene 11, gene 12, gene 13, and gene 14, wherein gene 11 is S100A12 or MMP9, wherein gene 12 is CLEC4E or ALOX5AP, wherein gene 13 is S100A8 or NAMPT, and wherein gene 14 is RPL28 or SSRP1;
wherein term 5 comprises gene 15, gene 16, gene 17, gene 18, and gene 19, wherein gene 15 is S100A12 or MMP9, wherein gene 16 is CLEC4E or ALOX5AP, wherein gene 17 is S100A8 or NAMPT, wherein gene 18 is AQP9 or GLT1D1, and wherein gene 19 is NCF4 or NCF2;
wherein term 6 comprises gene 20, gene 21, gene 22, gene 23, gene 24, gene 25, and gene 26, wherein gene 20 is CASP5 or H3F3B, wherein gene 21 is IL18RAP or TXN, wherein gene 22 is TNFAIP6 or PLAUR, wherein gene 23 is IL8RB or BCL2A1, wherein gene 24 is TNFRSF10C or PTAFR, wherein gene 25 is KCNE3 or LAMP2, and wherein gene 26 is TLR4 or TYROBP; and
wherein term 7 comprises gene 27, gene 28, gene 29, and gene 30, wherein gene 27 is SLAMF7 or CX3CR1, wherein gene 28 is KLRC4 or CD8A, wherein gene 29 is CD3D or LCK, and wherein gene 30 is TMC8 or CCT2;
generating, based on the assay, a dataset comprising data representing mRNA expression levels corresponding to each of the genes;
obtaining data representing age of the subject and data representing gender of the subject; and
generating, by a computer processor, a score indicative of coronary artery disease (CAD) risk by mathematically combining the data representing the mRNA expression levels, the data representing the age of the subject, and the data representing the gender of the subject, wherein a higher score relative to a control subject having less than 50% stenosis in all major vessels indicates an increased likelihood that the subject has CAD or a lower score relative to a control subject having greater than or equal to 50% stenosis in at least one major coronary vessel indicates a decreased likelihood that the subject has CAD.

2. The method of claim 1, wherein the dataset comprises data representing mRNA expression levels corresponding to each gene in term 1, term 2, term 3, term 4, term 5, term 6, and term 7.

3. The method of claim 1, further comprising classifying the first sample according to the score.

4. The method of claim 1, further comprising rating CAD risk using the score.

5. The method of claim 1, wherein the first sample comprises RNA extracted from peripheral blood cells.

6. A method for determining coronary artery disease risk in a subject, comprising:
performing RT-PCR on a sample from the subject by using a plurality of distinct primer and probe sets that specifically hybridize to mRNA corresponding to at least two genes comprising AF161365, HNRPF, ACBD5, TFCP2, DDX18, AF289562, CD248, CD79B, CD19, SPIB, BLK, CD3D, LCK, TMC8, CCT2, S100A12, MMP9, CLEC4E, ALOX5AP, S100A8, NAMPT, RPL28, SSRP1, AQP9, GLT1D1, NCF4, NCF2, CASP5, H3F3B, IL18RAP, TXN, TNFAIP6, PLAUR, IL8RB, BCL2A1, TNFRSF10C, PTAFR, KCNE3, LAMP2, TLR4, TYROBP, SLAMF7, CX3CR1, KLRC4, and CD8A;
generating, based on the RT-PCR, a dataset comprising data representing mRNA expression levels corresponding to each of the genes;
obtaining data representing age of the subject and data representing gender of the subject; and
generating, by a computer processor, a score indicative of CAD risk by mathematically combining the data representing the mRNA expression levels, the data representing the age of the subject, and the data representing the gender of the subject, wherein a higher score relative to a control subject having less than 50% stenosis in all major vessels indicates an increased likelihood that the subject has CAD or a lower score relative to a control subject having greater than or equal to 50% stenosis in at least one major coronary vessel indicates a decreased likelihood that the subject has CAD.

7. The method of claim 6, further comprising classifying the first sample according to the score.

8. The method of claim 6, further comprising rating CAD risk using the score.

9. The method of claim 1, wherein the method performance is characterized by an area under the curve (AUC) ranging from 0.68 to 0.70.

10. The method of claim 6, wherein the method performance is characterized by an AUC ranging from 0.68 to 0.70.

11. The method of claim 1, wherein the method performance is characterized by an AUC ranging from 0.70 to 0.79.

12. The method of claim 6, wherein the method performance is characterized by an AUC ranging from 0.70 to 0.79.

13. The method of claim 1, wherein the method performance is characterized by an AUC ranging from 0.80 to 0.89.

14. The method of claim 6, wherein the method performance is characterized by an AUC ranging from 0.80 to 0.89.

15. The method of claim 1, wherein the method performance is characterized by an AUC ranging from 0.90 to 0.99.

16. The method of claim 6, wherein the method performance is characterized by an AUC ranging from 0.90 to 0.99.

17. The method of claim 1, wherein the subject has stable chest pain, the subject has typical angina or atypical angina or an anginal equivalent, the subject has no previous diagnosis of myocardial infarction (MI), the subject has not had a revascularization procedure, the subject does not have diabetes, the subject does not have a systemic autoimmune or infectious condition, and/or the subject is not currently taking a steroid, an immunosuppressive agent, or a chemotherapeutic agent.

18. The method of claim 6, wherein the subject has stable chest pain, the subject has typical angina or atypical angina or an anginal equivalent, the subject has no previous diagnosis of MI, the subject has not had a revascularization procedure, the subject does not have diabetes, the subject does not have a systemic autoimmune or infectious condition, and/or the subject is not currently taking a steroid, an immunosuppressive agent, or a chemotherapeutic agent.

19. The method of claim 1, wherein CAD is obstructive CAD.

20. The method of claim 6, wherein CAD is obstructive CAD.

* * * * *